(12) United States Patent
Ahmadi et al.

(10) Patent No.: US 11,021,543 B2
(45) Date of Patent: Jun. 1, 2021

(54) IMMUNE MODULATION AND TREATMENT OF SOLID TUMORS WITH ANTIBODIES THAT SPECIFICALLY BIND CD38

(71) Applicant: Janssen Biotech, Inc., Horsham, PA (US)

(72) Inventors: Tahamtan Ahmadi, Spring House, PA (US); Tineke Casneuf, Beerse (BE); Henk Lokhorst, De Boelelaan (NL); Tuna Mutis, De Boelelaan (NL); Amy Sasser, Doylestown, PA (US); Niels van de Donk, De Boelelaan (NL)

(73) Assignee: Janssen Biotech, Inc., Horsham, PA (US)

( * ) Notice: Subject to any disclaimer, the term of this patent is extended or adjusted under 35 U.S.C. 154(b) by 65 days.

(21) Appl. No.: 16/162,355

(22) Filed: Oct. 16, 2018

(65) Prior Publication Data

US 2019/0144557 A1 May 16, 2019

Related U.S. Application Data

(63) Continuation of application No. 15/340,214, filed on Nov. 1, 2016, now abandoned, which is a continuation-in-part of application No. 15/191,808, filed on Jun. 24, 2016, now abandoned.

(60) Provisional application No. 62/331,489, filed on May 4, 2016, provisional application No. 62/263,307, filed on Dec. 4, 2015, provisional application No. 62/250,566, filed on Nov. 4, 2015, provisional application No. 62/249,546, filed on Nov. 2, 2015, provisional application No. 62/184,018, filed on Jun. 24, 2015.

(51) Int. Cl.

| | | |
|---|---|---|
| *C07K 16/28* | (2006.01) | |
| *A61K 39/395* | (2006.01) | |
| *C07K 16/40* | (2006.01) | |
| *A61K 38/47* | (2006.01) | |
| *A61K 45/06* | (2006.01) | |
| *A61K 31/454* | (2006.01) | |
| *A61K 31/573* | (2006.01) | |
| *A61K 39/00* | (2006.01) | |

(52) U.S. Cl.
CPC ........ *C07K 16/2896* (2013.01); *A61K 31/454* (2013.01); *A61K 31/573* (2013.01); *A61K 38/47* (2013.01); *A61K 39/39558* (2013.01); *A61K 45/06* (2013.01); *C07K 16/40* (2013.01); *C12Y 204/99* (2013.01); *C12Y 302/01035* (2013.01); *A61K 2039/505* (2013.01); *A61K 2039/545* (2013.01); *A61K 2039/55* (2013.01); *C07K 2317/56* (2013.01); *C07K 2317/565* (2013.01)

(58) Field of Classification Search
CPC ...... C12Y 302/01035; A61K 2039/505; A61K 39/39558; C07K 2317/56; C07K 2317/565

See application file for complete search history.

(56) References Cited

U.S. PATENT DOCUMENTS

| | | |
|---|---|---|
| 6,737,056 B1 | 5/2004 | Presta |
| 7,183,387 B1 | 2/2007 | Presta |
| 7,223,397 B1 | 5/2007 | Rosenblum et al. |
| 7,829,673 B2 | 11/2010 | DeWeers |
| 7,829,693 B2 | 11/2010 | Kreutzer et al. |
| 8,088,896 B2 | 1/2012 | Tesar et al. |
| 8,153,765 B2 | 4/2012 | Park et al. |
| 9,040,050 B2 | 5/2015 | Van De Winkel |
| 9,603,927 B2 | 3/2017 | Doshi |
| 9,732,154 B2 | 8/2017 | Doshi |
| 10,385,135 B2 | 8/2019 | Jansson et al. |
| 10,556,961 B2 | 2/2020 | Doshi |
| 10,604,580 B2 | 3/2020 | Lokhorst |
| 10,668,149 B2 | 6/2020 | Doshi et al. |
| 10,766,965 B2 | 9/2020 | Chaulagain |
| 10,781,261 B2 | 9/2020 | Jansson et al. |
| 10,793,630 B2 | 10/2020 | Doshi et al. |
| 10,800,851 B2 | 10/2020 | Doshi |
| 2004/0141982 A1 | 7/2004 | Lust et al. |
| 2004/0268425 A1 | 12/2004 | Bookbinder et al. |
| 2006/0257397 A1 | 11/2006 | Throsby |
| 2007/0148178 A1 | 6/2007 | Fyfe et al. |
| 2008/0063642 A1 | 3/2008 | Adelman et al. |
| 2008/0166344 A1 | 7/2008 | Nakahara et al. |
| 2009/0076249 A1 | 3/2009 | Deweers et al. |
| 2009/0148449 A1 | 6/2009 | DeWeers |
| 2009/0304687 A1 | 12/2009 | Drachman |
| 2009/0304710 A1 | 12/2009 | Park et al. |
| 2010/0068136 A1 | 3/2010 | Hansen |
| 2010/0092489 A1* | 4/2010 | Van De Winkel ..... A61K 45/06 424/172.1 |
| 2010/0285004 A1 | 11/2010 | Tesar et al. |
| 2011/0044997 A1 | 2/2011 | Adler et al. |

(Continued)

FOREIGN PATENT DOCUMENTS

| | | |
|---|---|---|
| AU | 2013203186 A1 | 5/2013 |
| CL | 2013001944 A1 | 9/2014 |

(Continued)

OTHER PUBLICATIONS

Almagro & Fransson, Frontiers in Bioscience 2008; 13:1619-1633.*

(Continued)

*Primary Examiner* — Hong Sang
(74) *Attorney, Agent, or Firm* — Hamilton, Brook, Smith & Reynolds, P.C.

(57) ABSTRACT

The present invention relates to methods of immunomodulation and treating patients having solid tumors with antibodies that specifically bind CD38.

19 Claims, 39 Drawing Sheets

Specification includes a Sequence Listing.

(56) References Cited

U.S. PATENT DOCUMENTS

| | | |
|---|---|---|
| 2011/0066111 A1 | 3/2011 | Teschner et al. |
| 2011/0076273 A1 | 3/2011 | Adler et al. |
| 2011/0099647 A1 | 4/2011 | De Weers et al. |
| 2011/0293606 A1 | 12/2011 | Lejeune |
| 2011/0300157 A1 | 12/2011 | Devy et al. |
| 2012/0201827 A1 | 8/2012 | Elias |
| 2012/0219551 A1 | 8/2012 | Johnson et al. |
| 2012/0231008 A1 | 9/2012 | Guo et al. |
| 2012/0244110 A1 | 9/2012 | Chen et al. |
| 2012/0258081 A1 | 10/2012 | Corringham et al. |
| 2012/0259095 A1 | 10/2012 | Beliard et al. |
| 2012/0295864 A1 | 11/2012 | Taube et al. |
| 2013/0109593 A1 | 5/2013 | Hartmann et al. |
| 2013/0137134 A1 | 5/2013 | Mordechai et al. |
| 2013/0209355 A1 | 8/2013 | De Weers et al. |
| 2013/0302400 A1 | 11/2013 | Maneval et al. |
| 2013/0309250 A1* | 11/2013 | Cogswell .............. A61P 35/00 424/172.1 |
| 2013/0323247 A1 | 12/2013 | Zugmaier et al. |
| 2014/0099254 A1 | 4/2014 | Chang et al. |
| 2014/0155584 A1 | 6/2014 | Elias et al. |
| 2014/0248238 A1 | 9/2014 | Wilson et al. |
| 2014/0271644 A1 | 9/2014 | Elias et al. |
| 2014/0309183 A1 | 10/2014 | Kerr |
| 2014/0356318 A1 | 12/2014 | Barken |
| 2015/0118251 A1 | 4/2015 | Deslandes |
| 2015/0125447 A1 | 5/2015 | Heider |
| 2015/0231235 A1 | 8/2015 | Van De Winkel |
| 2015/0246123 A1 | 9/2015 | Doshi |
| 2015/0246975 A1 | 9/2015 | Doshi |
| 2015/0376276 A1* | 12/2015 | Lewis .................. A61P 35/02 424/133.1 |
| 2016/0009683 A1 | 1/2016 | Hansen et al. |
| 2016/0067205 A1 | 3/2016 | Lokhorst |
| 2016/0222106 A1 | 8/2016 | Doshi et al. |
| 2016/0367663 A1 | 12/2016 | Doshi et al. |
| 2016/0376373 A1 | 12/2016 | Ahmadi |
| 2017/0008966 A1 | 1/2017 | Chaulagain |
| 2017/0044265 A1 | 2/2017 | Ahmadi |
| 2017/0107295 A1 | 4/2017 | Lokhorst |
| 2017/0121414 A1 | 5/2017 | Jansson et al. |
| 2017/0121417 A1 | 5/2017 | Jansson et al. |
| 2017/0174780 A1 | 6/2017 | Doshi |
| 2017/0320961 A1 | 11/2017 | Doshi |
| 2018/0117150 A1 | 5/2018 | O'Dwyer et al. |
| 2019/0127479 A1 | 5/2019 | Ahmadi et al. |
| 2019/0144557 A1 | 5/2019 | Ahmadi et al. |
| 2019/0233533 A1 | 8/2019 | Otten |
| 2019/0330363 A1 | 10/2019 | Janssen et al. |
| 2020/0002433 A1 | 1/2020 | Jansson et al. |
| 2020/0121588 A1 | 4/2020 | Campbell et al. |
| 2020/0223936 A1 | 7/2020 | Doshi et al. |
| 2020/0231697 A1 | 7/2020 | Jansson et al. |
| 2020/0339701 A1 | 10/2020 | Jansson et al. |
| 2020/0392242 A1 | 12/2020 | Liu |
| 2020/0397896 A1 | 12/2020 | Liu |
| 2020/0405854 A1 | 12/2020 | Liu |
| 2020/0407459 A1 | 12/2020 | Chaulagain et al. |
| 2021/0047401 A1 | 2/2021 | Doshi et al. |
| 2021/0061920 A1 | 3/2021 | Doshi |
| 2021/0095042 A1 | 4/2021 | Jansson et al. |

FOREIGN PATENT DOCUMENTS

| | | |
|---|---|---|
| CL | 2016002158 A1 | 7/2017 |
| EA | 009383 B1 | 12/2007 |
| EA | 015584 B1 | 10/2011 |
| EA | 201390993 A1 | 12/2013 |
| EP | 2561868 A1 | 2/2013 |
| EP | 2567976 A2 | 3/2013 |
| JP | 2002-534396 A | 10/2002 |
| JP | 2008-533977 A | 8/2008 |
| JP | 2009-511033 A | 3/2009 |
| JP | 2010-506582 A | 3/2010 |
| JP | 2014-509837 A | 4/2014 |
| NZ | 576122 | 9/2012 |
| WO | WO 89/08114 A1 | 9/1989 |
| WO | WO 92/01049 A2 | 1/1992 |
| WO | WO 94/17184 A1 | 8/1994 |
| WO | WO 96/16990 A1 | 6/1996 |
| WO | WO 98/16245 A1 | 4/1998 |
| WO | WO 98/16254 A1 | 4/1998 |
| WO | WO 98/50435 A1 | 11/1998 |
| WO | WO 99/62526 A2 | 12/1999 |
| WO | WO 00/06194 A2 | 2/2000 |
| WO | WO 00/40265 A1 | 7/2000 |
| WO | WO 01/97844 A1 | 12/2001 |
| WO | WO 02/06347 A1 | 1/2002 |
| WO | WO 02/32288 A2 | 4/2002 |
| WO | WO 2003/106498 A2 | 12/2003 |
| WO | WO 2004/058288 A1 | 7/2004 |
| WO | WO 2004/078140 A2 | 9/2004 |
| WO | WO 2005/042019 A1 | 5/2005 |
| WO | WO 2005/044855 A2 | 5/2005 |
| WO | WO 2005/063819 A2 | 7/2005 |
| WO | WO 2005/103083 A2 | 11/2005 |
| WO | WO 2006/088951 A2 | 8/2006 |
| WO | WO 2006/099875 A1 | 9/2006 |
| WO | WO 2006/125640 A2 | 11/2006 |
| WO | WO 2007/042309 A2 | 4/2007 |
| WO | WO 2008/037257 A2 | 4/2008 |
| WO | WO 2008/047242 A2 | 4/2008 |
| WO | WO 2008/073160 A2 | 6/2008 |
| WO | WO 2008/116103 A2 | 9/2008 |
| WO | WO 2008/121615 A2 | 10/2008 |
| WO | WO 2008/150530 A2 | 12/2008 |
| WO | WO 2009/062054 A1 | 5/2009 |
| WO | WO 2009/118142 A1 | 10/2009 |
| WO | WO 2009/128917 | 10/2009 |
| WO | WO 2010/052014 | 5/2010 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |
| WO | WO 2011/109365 A2 | 9/2011 |
| WO | WO 2011/154453 A1 | 12/2011 |
| WO | WO 2012/041800 A1 | 4/2012 |
| WO | WO 2012/076663 A1 | 6/2012 |
| WO | WO 2012/092612 A1 | 7/2012 |
| WO | WO 2012/092616 A1 | 7/2012 |
| WO | WO 2013/059885 A2 | 5/2013 |
| WO | WO 2013/164837 A1 | 11/2013 |
| WO | WO 2014/048921 A1 | 4/2014 |
| WO | WO 2014/068114 A1 | 5/2014 |
| WO | WO 2014/089416 A1 | 6/2014 |
| WO | WO 2014/142220 A1 | 9/2014 |
| WO | WO 2014/178820 A1 | 11/2014 |
| WO | WO 2015/009726 A2 | 1/2015 |
| WO | WO 2015/066450 A1 | 7/2015 |
| WO | WO 2015/130728 A1 | 9/2015 |
| WO | WO 2015/130732 A2 | 9/2015 |
| WO | WO 2015/195555 A1 | 12/2015 |
| WO | WO 2015/195556 A1 | 12/2015 |
| WO | WO 2016/040294 A2 | 3/2016 |
| WO | WO 2016/089960 A1 | 6/2016 |
| WO | WO 2016/133903 A2 | 8/2016 |
| WO | WO 2016/187546 A1 | 11/2016 |
| WO | WO 2016/209921 A1 | 12/2016 |
| WO | WO 2016/210223 A1 | 12/2016 |
| WO | WO 2017/079150 A1 | 5/2017 |
| WO | WO 2018/002181 A1 | 1/2018 |
| WO | WO 2019/089832 A1 | 5/2019 |
| WO | WO 2019/186273 A1 | 10/2019 |

OTHER PUBLICATIONS

Berglund et al., Protein Science, 2008, 17:606-613.*
Tzartos et al., Methods in Molecular Biology, 1996, 66:55-66.*
Carter et al., Endocrine-Related Cancer, 2004, 11:659-687.*
Clinical Trial NCT02519452, fist posted on Aug. 6, 2015.*

(56) References Cited

OTHER PUBLICATIONS

ClinicalTrials.gov, "Daratumumab in Combination with ATRA (DARA/ATRA)," Identifier: NCT02751255; First posted: Apr. 26, 2016 (11 pages).

ClinicalTrials.gov, "A Study of Daratumumab with the Addition of Recombinant Human Hyaluronidase (rHuPH20) for the Treatment of Participants with Relapsed or Refractory Multiple Myeloma," Identifier: NCT02519452; First Posted: Aug. 11, 2015 (13 pages).

ClinicalTrials.gov, "A Study to Evaluate Subcutaneous Daratumumab in Combination with Standard Multiple Myeloma Treatment Regimens," Identifier: NCT03412565, First Posted: Jan. 26, 2018 (16 pages).

ClinicalTrials.gov, "A Phase 1 Study to Assess the Safety, Tolerability, and Pharmacokinetics of TAK-079 in Healthy Participants," Identifier: NCT02219256, Latest version posted: Mar. 22, 2017 (13 pages).

Dispenzieri, A. et al., "Treatment of Immunoglobulin Light Chain Amyloidosis: Mayo Stratification of Myeloma and Risk-Adapted Therapy (mSMART) Consensus Statement," Mayo Clin Proc., vol. 90; No. 8; 1054-1081 (2015).

Fujioka, Y. and Kurokawa, M., "Follicular lymphoma presenting with massive splenomegaly," International J Hematol, vol. 95; 3-4 (2012).

Kaufman, G.P. et al., "Daratumumab yields rapid and deep hematologic responses in patients with heavily pretreated AL amyloidosis," Blood, vol. 130; No. 7; 900-902 (2017).

Machida, H. et al., "Aggressive plasma cell leukemia with cleaved, multilobated and monocytoid nuclei," International Journal of Hematol., vol. 73; Suppl 1; 158; Abstract No. 411 (2001).

Mai, E. et al., "Phase III trial of bortezomib, cyclophosphamide and dexamethasone (VCD) versus bortezomib, doxorubicin and dexamethasone (Pad) in newly diagnosed myeloma," Leukemia, vol. 29; 1721-1729 (2015).

Park, S. et al., "Successful Treatment by Rituximab of an Ebv-Related Lymphoma after Autologous Transplantation for Angioimmunoblastic T-Cell Lymphoma," International Journal of Hematol., vol. 76; Suppl. 1; 118; Abstract No. P340 (2002).

Rai, S. et al., "Successful Allogeneic Hematopoietic Stem Cell Transplantation in a Young Patient with Richter Syndrome Presenting with Chronic Lymphocytic Leukemia and Diffuse Large B-Cell Lymphoma with Different Cell Origins," Intern Med, vol. 52; 273-276 (2013).

Saito, M. et al., "A Case of Retroperitoneal Extramedullary Plasmacytoma," Acta Urol. Jpn., vol. 49; 735-739 (2003).

Smithson, G. et al., "TAK-079 is a high affinity monoclonal antibody that effectively mediates CD38+ cell depletion," Journal of Immunol., vol. 198; Suppl. 1; 224.20; Abstract (2017).

Usmani, S.Z. et al., "Open-Label, Multicenter, Dose Escalation Phase 1b Study to Assess the Subcutaneous Delivery of Daratumumab in Patients (pts) with Relapsed or Refractory Multiple Myeloma," Blood, vol. 128; No. 22; 1149 (2016).

Usmani, S.Z. et al., "Subcutaneous delivery of daratumumab in relapsed or refractory multiple myeloma," Blood, vol. 134; No. 8; 668-677 (2019).

International Preliminary Report on Patentability dated Jan. 10, 2019 for International Application No. PCT/EP2017/066063, entitled "Treatment of IgE-Mediated Diseases With Antibodies That Specifically Bind CD38".

International Preliminary Report on Patentability dated May 14, 2020 for International Application No. PCT/US2018/058561, entitled "Methods of Treating High Risk Multiple Myeloma".

International Search Report and Written Opinion dated Apr. 24, 2020 for International Application No. PCT/US2019/056838, entitled "Method of Providing Subcutaneous Administration of Anti-CD38 Antibodies".

Notice of Allowance for U.S. Appl. No. 15/386,391 dated Nov. 18, 2019.

Notice of Allowance for U.S. Appl. No. 15/445,225 dated Dec. 4, 2019.

Notice of Allowance for U.S. Appl. No. 15/189,577 dated Dec. 19, 2019.

Non Final Office Action for U.S. Appl. No. 15/160,476 dated Dec. 20, 2019.

Final Office Action for U.S. Appl. No. 14/956,890 dated Jan. 7, 2020.

Non-Final Office Action for U.S. Appl. No. 15/798,670 dated Jan. 22, 2020.

English translation of Office Action for JP Application No. 2016-554350, mailed Nov. 27, 2018.

Notice of Allowance for U.S. Appl. No. 15/445,225 dated Mar. 25, 2020.

Notice of Allowance for U.S. Appl. No. 15/189,577 dated Mar. 31, 2020.

Notice of Allowance for U.S. Appl. No. 15/160,476 dated May 4, 2020.

Notice of Allowance for U.S. Appl. No. 16/380,994 dated May 12, 2020.

Notice of Allowance for U.S. Appl. No. 16/460,754 dated May 18, 2020.

Notice of Allowance for U.S. Appl. No. 15/445,225 dated Jul. 15, 2020.

Abdi, J. et al., "Drug resistance in multiple myeloma: latest findings and new concepts on molecular mechanisms," Oncotarget, vol. 4; No. 12; 2186-2207 (2013).

Chaulagain, C.P. and Comenzo, R.L., "New Insights and Modern Treatment of AL Amyloidosis," Curr Hematol Malig Rep, vol. 8; 291-298 (2013).

Chiarugi, A. et al., "The NAD metabolome—a key determinant of cancel cell biology," Nature Reviews, vol. 12; 741-752 (2012).

Comenzo, R.L. et al., "Consensus guidelines for the conduct and reporting of clinical trials in systemic light-chain amyloidosis," Leukemia, vol. 26; 2317-2325 (2012).

Ettinger, R. et al., "Pathogenic mechanisms of IgE-mediated inflammation in self-destructive autoimmune responses," Autoimmunity, vol. 50; No. 1; 25-36 (2017).

Gupta, R. et al., "The Economic Impact of Childhood Food Allergy in the United States," JAMA Pediatrics, vol. 167; No. 11; 1026-1031 (2013).

Holgate, S.T., "New strategies with anti-IgE in allergic diseases," World Allergy Organization Journal, vol. 7; No. 17; 6 pages (2014).

Inaba, H. et al., "Acute lymphoblastic leukaemia," Lancet, vol. 381; 27 pages (2013).

Krejcik, J. et al., "Daratumumab depletes CD38+ immune regulatory cells, promotes T-cell expansion, and skews T-cell repertoire in multiple myeloma," Blood, vol. 128; No. 3; 384-394 (2016).

Krejcik, J. et al., Immunomodulatory Effects and Adaptive Immune Response to Daratumumab in Multiple Myeloma,: Blood, vol. 126; 3037; 7 pages (2015).

Lepenies, B. and Jacobs, T., "The Role of Negative Costimulators During Parasitic Infections," Endocrine, Metabolic & Immune Disorders—Drug Targets, vol. 8; 279-288 (2008).

Manier, S. et al., "Bone Marrow Microenvironment in Multiple Myeloma Progession," Journal of Biomedicine and Biotechnology, vol. 2012; 5 pages (2012).

Mauri, C. and Menon, M., "The expanding family of regulatory B cells," International Immunology, vol. 27; No. 10; 479-486 (2015).

Merlini, G. and Bellotti, V., "Molecular Mechanisms of Amyloidosis," The New England Journal of Medicine, vol. 349; No. 6; 583-596 (2003).

Mills, E.N.C. et al., "The prevalence, cost and basis of food allergy across Europe," Allergy, vol. 62; 717-722 (2007).

Nijhof, I.S. et al., Preclinical Evidence for the Therapeutic Potential of CD38-Targeted Immuno-Chemotherapy in Multiple Myeloma Patients Refractory to Lenalidomide and Bortezomib. Clin Cancer Res., vol. 21, No. 12, pp. 2802-2810 (2014).

Patel, J.P., "Prognostic Relevance of Integrated Genetic Profiling in Acute Myeloid Leukemia," The New England Journal of Medicine, vol. 366; No. 12; 1079-1089 (2012).

Patton, D.T. et al., "The P13K p110δ Regulates Expression of CD38 on Regulatory T Cells," PLOS one, vol. 6; No. 3; e17359; 8 pages (2011).

(56) References Cited

OTHER PUBLICATIONS

Sher, T. et al., "First report of safety and efficacy of daratumumab in 2 cases of advanced immunoglobulin light chain amyloidosis," Blood, vol. 128; No. 15; 1987-1989 (2016).
Sicherer, S.H. and Sampson, H.A., "Food allergy: Epidemiology, pathogenesis, diagnosis, and treatment," J. Allergy Clin Inmmunol, vol. 133; 291-307 (2014).
Swaika, A. et al., "Current state of anti-PD-L1 and anti-PD-1 agents in cancer therapy," Molecular Immunology, vol. 67; 4-17 (2015).
Talmadge, J.E. and Gabrilovich, D.I, "History of myeloid-derived suppressor cells," Nature Reviews, vol. 13; 739-752 (2013).
Wang, L. et al., "VISTA, a novel mouse Ig superfamily ligand that negatively regulates T cell responses," J. Exp. Med., vol. 208; No. 3; 577-592 (2011).
Wei, W. et al., "Roles and mechanisms of the CD38/cyclic adenosine diphosphate ribose/Ca2+ signaling pathway," World Journal of Biological Chemistry, vol. 5; No. 1; 58-67 (2014).
Notice of Allowance for U.S. Appl. No. 15/386,391 dated Mar. 29, 2019.
Notice of Allowance for U.S. Appl. No. 15/340,290 dated May 22, 2019.
Notice of Allowance for U.S. Appl. No. 15/651,333 dated May 31, 2019.
Final Office Action for U.S. Appl. No. 15/160,476 dated Jun. 14, 2019.
Notice of Allowance for U.S. Appl. No. 15/445,225 dated Jul. 29, 2019.
Notice of Allowance for U.S. Appl. No. 15/386,391 dated Jul. 30, 2019.
Non-Final Office Action for U.S. Appl. No. 14/956,890 dated Jul. 30, 2019.
"A Prospective Phase II of Daratumumab in Previously Treated Systemic Light Chain (AL) Amyloidosis", published online at (http://cms.cws.net/content/beta.myelomasociety.org/files/2017ash/Roussel,%20Murielle-ASH2017.pdf (2017).
Aarhust, et al., "ADP-ribosyl Cyclase and CD38 Catalyze the Synthesis of a Calcium mobilizing Metabolite from NADP+," The Journal of Biological Chemistry, 270(51): 30327-30333 (1995).
Adriouch et al., "Extracellular NAD+: a danger signal hindering regulatory T cells," Microbes and Infection, 14:1284-1292 (2012).
Agheli, A. et al., "A Rare Case of Primary Amyloidosis, Presenting with Severe Pulmonary Hypertension and Bilateral Pleural Effusion," Blood, vol. 106: p. 5100 (2005).
Arican, et al., "Philadelphia Chromosome (+) T-Cell Acute Lymphoblastic Leukemia After Renal Transplantation," Transplantation Proceedings, vol. 31; 3242-3243 (1999).
Armitage et al., "Long-Term Remission Durability and Functional Status of Patients Treated for Diffuse Histiocytic Lymphoma with the CHOP Regimen," J. Clin. Oncol. 2:898-902, (1984).
Arthur, "Innovations in subcutaneous infusions," J. Infus. Nurs. 38(3); 179-87; May/Jun. 2015.
Bachireddy, et al., "Haematologic Malignancies: at the Forefront of Immunotherapeutic Innovation," Nature Reviews Cancer, vol. 15, No. 4, pp. 201-215, Apr. 1, 2015 (Apr. 1, 2015).
Bahlis, N.J. et al., "Daratumumab, lenalidomide, and dexamethasone (DRd) vs lenalidomide and dexamethasone (Rd) in relapsed or refractory multiple myeloma (RRMM): Efficacy and safety updated (POLLUX)," Journal of Clinical Oncology, vol. 35; No. 15; 8025; Abstract (2017).
Blankestijn, et al., "Could daratumumab be used to treat severe allergy?," Journal of Allergy and Clinical Immunology, Elsevier, Amsterdam, NL, vol. 139, No. 5, p. 1677-1678, Jan. 19, 2017.
Brand, F-X. et al., "Prospect for Anti-HER2 Receptor Therapy in Breast Cancer," AntiCancer Research, vol. 26; 463-470 (2006).
Brown, et al., "Tolerance of single, but not multiple, amino acid replacements in antibody VH CDR 2: a means of minimizing B cell wastage from somatic hypermutation?" The Journal of Immunology, 156: 3285-3291 (1996).

Carter et al., "Identification and validation of cell surface antigens for antibody targeting in oncology," Endocrine-Related Cancer, vol. 11, pp. 659-687, (2004).
Chari et al., "Subcutaneous Delivery of Daratumumab in Patients with Relapsed or Refractory Multiple Myeloma (RRMM): PAVO, an Open-label, Multicenter, Dose Escalation Phase 1b Study," American Society of Hematology, Clinical Trials.gov Identifier NCT02519452, Dec. 2017.
Chari A. et al., "Subcutaneous delivery of daratumumab in patients (pts) with relapsed or refractory multiple myeloma (RRMM): PAVO, an openlabel, multicenter, dose escalation phase 1b study," 2017 ASH Annual Meeting *ANZMAP Multiple Myeloma Highlights*, 2017.
Chaulagain, C.P., et al., "How we Treat Systemic Light-Chain Amyloidosis," Clinical Advances in Hematology & Oncology, vol. 13; No. 5; 315-324 (2015).
Chen, et al., "Selection and Analysis of an Optimized Anti-VEGF Antibody: Crystal Structure of an Affinity-matured Fab in Complex with Antigen," Journal of Molecular Biology, 293: 865-881 (1999).
Cheson et al., "Revised Response Criteria for Malignant Lymphoma," Journal of Clinical Oncology, vol. 25, No. 5, 579-586 (Feb. 10, 2007).
Chillemi, A. et al., "Anti-CD38 Antibody Therapy: Windows of Opportunity Yielded by the Functional Characteristics of the Target Molecule," Molecular Medicine, vol. 19; 99-108 (2013).
Chou, et al., "Drug Combination Studies and their Synergy Quantification Using the Chou-Talalay Method," Cancer Research, 70(2): 440-446 (2010).
ClinicalTrials.gov "Study of YM155 in Refractory Diffuse Large B-cell Lymphoma (DLBCL) Subjects," Interventional Studies, U.S. National Library of Medicine, https://clinicaltrials.gov/ct2/show/record/NCT00498914, First posted Jul. 11, 2007 [retrieved on Sep. 10, 2018].
Colman, "Effects of amino acid sequence changes on antibody-antigen interactions, A Structural View of Immune Recognition by Antibodies," Biomolecular Research Institute, 33-36, (1994).
Cotner, et al., "Human T Cell Proteins Recognized by Rabbit Heteroantisera and Monoclonal Antibodies," International Journal of Immunopharmaceuticals, 3(3): 255-268 (1981).
Davies, et al., "Affinity improvement of single antibody VH domains: residues in all three hypervariable regions affect antigen binding," Immunotechnology, 2: 169-179 (1996).
Davis, et al., "Transgenic mice as a source of fully human antibodies for the treatment of cancer," Cancer and Metastasis Reviews, 18: 421-425 (1999).
Deckert, et al., "SAR650984, A Novel Humanized CD38-Targeting Antibody, Demonstrates Potent Antitumor Activity in Models of Multiple Myeloma and Other CD38β Hematologic Malignancies," Clinical Cancer Research. vol. 20, No. 17, pp. 4574-4583 (2014).
Dennis, "Off by a Whisker," Nature, 442 (17): 749-741 (2006).
DePascalis, et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084 (2002).
De Weers, et al., "Daratumumab, a Novel Therapeutic Human CD38 Monoclonal Antibody, Induces Killing of Multiple Myeloma and Other Hematological Tumors," The Journal of Immunology, 186: 1840-1848 (Pre-published online Dec. 27, 2010).
De Weers, M. et al., "Humax-CD38, a New Human CD38 Monoclonal Antibody, Effectively Mediates Killing of Multiple Myeloma and Plasma Cell Leukemia Cells," abstract, Submitted for the 16th European Congress of Immunology—ECI2006, Paris, France, [Sep. 6-9, 2006].
De Weers et al., "HuMax-CD38, a new human CD38 monoclonal antibody, effectively mediates killing of multiple myeloma and plasma cell leukemia cells," The 23rd International Conference on Advances in the Application of Monoclonal Antibodies in Clinical Oncology, (Jun. 26-28, 2006), Royal Myconian Resort & Thalasso Spa Center, Mykonos, Greece (Abstract).
Dimopoulos, M.A. et al., "Daratumumab, Lenalidomide, and Dexamethasone for Multiple Myeloma," The New England Journal of Medicine, vol. 375; No. 14; 1319-1331 (2016).

(56) References Cited

OTHER PUBLICATIONS

Dimopoulos, M.A. et al., "Daratumumab plus lenalidomide and dexamethasone versus lenalidomide and dexamethasone in relapsed or refractory multiple myeloma: updated analysis of POLLUX," Haematologica, vol. 103; No. 12; 2088-2096 (2018).

Dos Santos, et al., Anti-Leukemic Activity of Daratumumab in Acute Myeloid Leukemia Cells and Patient-Derived Xenografts, Blood, vol. 124, Abstract 2312, (2014).

Doshi, et al., "Daratumumab Treatment in Combination with Chop or R-Chop Results in the Inhibition or Regression of Tumors in Preclinical Models of Non-Hodgkins Lymphoma," Haematologica, The Hematology Journal, 99(1): 138 (2014).

Ellis, et al., "Engineered Anti-CD38 Monoclonal Antibodies for Immunotherapy of Multiple Myeloma," The Journal of Immunology, 155: 925-937 (1995).

Eldfors, et al., "Landscape of Mutations in Relapsed Acute Myeloid Leukemia," vol. 124: No. 21, p. 2367; (2014).

Engert, et al., "A Phase-I Study of an Anti-CD25 Ricin A-Chain Immunotoxin (RFT5-SMPT-dgA) in Patients with Refractory Hodgkin's Lymphoma," Blood, 89(2): 403-410 (1997).

Ferrero, et al., Characterization and phylogenetic epitope mapping of CD38 ADPR cyclase in the cynomolgus macaque, BMC Immunology, 5(21): 1-13 (2004).

Field-Smith, "Bortezomid (Velcade™) in the treatment of multiple myeloma," Therapeutic and Clinical Risk Management, 2(3): 271-279 (2006).

Flavell, et al., "Therapy of human T-cell acute lymphoblastic leukaemia with a combination of anti-CD7 and anti-CD38-SAPORIN immunotoxins is significantly better than therapy with each individual immunotoxin," Br. J. Cancer, vol. 84, No. 4, pp. 571-578, (2001).

Franco, et al., "The transmembrane glycoprotein CD38 is a catalytically active transporter responsible for generation and influx of the second messenger cyclic ADP-ribose across membranes," FASEB Journal, 12: 1507-1520 (1998).

Fujimori, et al., "A Modeling Analysis of Monoclonal Antibody Percolation Though Tumors: A Binding-Site Barrier," Journal of Nucleic Medicine, 31: 1191-1198 (1990).

Funaro et al., "CD38 Functions Are Regulated Through an Internalization Step," Journal of Immunology, 160: 2238-2247 (1998).

Funaro, et al., "Human CD38: a versatile leukocyte molecule with emerging clinical prospectives," Fundamental and Clinical Immunology, 3(3): 101-113 (1995).

Funaro, et al., "Identification and characterization of an active soluble form of human CD38 in normal and pathological fluids," International Immunology, 8(11): 1643-1650 (1996).

Funaro, et al., "Involvement of the Multilineage CD38 Molecule in a Unique Pathway of Cell Activation and Proliferation," The Journal of Immunology, 145: 2390-2396 (1990).

Gallo, et al., "The human immunoglobulin loci introduced into mice: V(D) and J gene segment usage similar to that of adult humans," European Journal of Immunology, 30: 534-540 (2000).

Genmab "Humanx-CD38 Effective in Preclinical Studies," Genmab A/S, Stock Exchange Release 57/2005.

Genmab "Daratumumab Receives Breakthrough Therapy Designation from US Food and Drug Administration", Copenhagen, Denmark; May 1, 2013—Genmab A/S (OMX: GEN) disponible en: http://files.shareholder.com/downloads/AMDA-KPIBN/0x0x659093/64b187b8-830c-4252-acd6-8019b4199069/18%20Daratumumab%20breakthrough%20status 010513_uk.pdf, (May 1, 2013).

Genmab Announces Daratumumab and Ofatumumab Data to Be Presented at American Society of Hematology Annual Meeting (ASH), American Society of Hematology Annual Meeting and Exposition, San Francisco, California, Media Release 06; pp. 1-3 (Nov. 2014).

George, et al., "Differential Effects of Anti-β2-Glycoprotein I Antibodies on Endothelial Cells and on the Manifestations of Experimental Antiphospholipid Syndrome," Circulation, 97: 900-906 (1998).

Goldmacher, et al., "Anti-CD38-Blocked Ricin: An immunotoxin for the Treatment of Multiple Myeloma," The American Society of Hematology, 84(9): 3017-3025 (1994).

Goodwin, "Subcutaneous Daratumumab Potential Game Changer for Multiple Myeloma," Oncology Times, 2017 American Society of Hematology Annual Meeting, p. 49, (2017).

Gopalakrishnan, et al. "Daratumumab improves the anti-myeloma effect of newly emerging multidrug therapies," Blood and Lymphatic Cancer: Targets and Therapy, 3: 19-24 (2013).

Graeff, et al., "Enzymatic Synthesis and Characterizations of Cyclic GDp-ribose," The Journal of Biological Chemistry, 269(48): 30260-30267 (1994).

Green, "Antibody engineering via genetic engineering of the mouse: XenoMouse strains are a vehicle for the facile generation of therapeutic human monoclonal antibodies," Journal of Immunological Methods, 231: 11-23 (1999).

Green, et al., "Antigen-specific human monoclonal antibodies from mice engineered with hyman Ig heavy and light chain YACs," Nature Genetics, 7: 13-21 (1994).

Guse et al., "Regulation of calcium signaling in T lymphocytes by the second messenger cyclic ADP-ribose," Nature 398:70-73, (1999).

Haart, et al., "Sepantronium bromide (YM155) improves daratumumab-mediated cellular lysis of multiple myeloma cells by abrogation of bone marrow stromal cell-induced resistance," Haematologica, Letters to the Editor, vol. 101, No. 8, pp. e339-e343, (2016).

Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).

Hartmann, Radioimmunotherapy of Nude Mice Bearing a Human Interleukin 2 Receptor α-expressing Lymphoma Utilizing the α-emitting Radionuclide-eonjugated Monoclonal Antibody 212Bi-anti-Tac, Cancer Research, 54: 4362-4370 (1994).

Henry, et al., "The use of basiliximab in solid organ transplantation," Expert Opinion Pharmacotherapy, 3(10): 1657-1663 (2002).

Holm, et al., "Functional mapping and single chain construction of the anti-cytokeratin 8 monoclonal antibody TS1," Molecular Immunology, 44: 1075-1084 (2017).

Hoshino, et al., "Mapping of the Catalylic and Epitopic Sites of Human CD38/NAD+ Glycohydrolase to a Functional Domain in the Carboxyl Terminus1," The Journal of Immunology, 158: 741-747 (1997).

Howard, et al., "Formation and Hydrolysis of Cyclic ADP-Ribose Catalyzed by lymphocyte Antigen CD38," Science, 262(5136): 1056-1059 (1993).

Hu, Y., et al., "Immunophenotypic analysis of abnormal plasma cell clones in bone marrow of primary systemic light chain amyloidosis patients," Chin Med J., vol. 127; No. 15; 2765-2770; Abstract only (2014).

Hu, Y. et al., "The Significance of Abnormal Plasma Cell Clone in Bone Marrow of Primary Systemic Light Chain Amyloidosis Patients," Blood, vol. 122; p. 5342 (2013).

Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).

Jackisch, et al., "Subcutaneous versus intravenous formulation of trastuzumab for HER2-positive early breast cancer: updated results from the phase III HannaH study," Annals of Oncology, vol. 26, pp. 320-325, (2015).

Jackson, et al., "Isolation of a cDNA Encoding the Human CD38 (T10) molecule, A Cell Surface Glycoprotein With an Unusual Discontinuous Pattern of Expression During Lymphocyte Differentiation," The Journal of Immunology, 144(7): 2811-2815 (1990).

Jagannath, et al. Treatment (tx) journeys in newly diagnosed multiple myeloma (NDMM) patients (pts): Results from the Connect MM Registry. Multiple Myeloma Update from the American Society of Clinical Oncology. (ASCO) 41st Annual meeting, (Jun. 4, 2018).

Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).

(56) References Cited

OTHER PUBLICATIONS

Jakobovits, "The long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia: morphologic, immunophenotypic, and cytogenetic features of 4 cases treated with chemotherapy and stem cell transplantation," Annals of Diagnostic Pathology, 10: 263-268 (2006).
Johnson & Johnson, Janssen to Demonstrate Breadth of Oncology Portfolio with 42 Clinical Data Presentation at the 2014 American Society of Hematology (ASH) Annual Meeting, San Francisco, California (Nov. 2014).
Jones, et al., "Depletion of CD25+ regulatory calls results in suppression of melanoma growth and induction of autoreactivity in mice," Cancer Immunity, 2: 1 (2002). Abstract.
Jones, et al., "Replacing the complementarity-determining regions in a human antibody with those from a mouse," Nature, 321: 522-525 (1986).
Kita et al., "Antitumor effects of YM155, a novel suppressant, against human aggressive non-Hodgkin Lymphoma," Leukemia Research, vol. 35, pp. 787-792, (2011).
Kita, A., et al., "Sepantronium Bromide (YM155) Enhances Response of Human B-Cell Non-Hodgkin Lymphoma to Rituximab," The Journal of Pharmacology and Experimental Therapeutics, vol. 343; No. 1; 178-183 (2012).
Konapleva, et al., "Ligation of Cell Surface CD38 Protein with Agonistic Monoclonal Antibody Induced a Cell Growth Signal in Myeloid Leukemia Cells," The Journal of Immunology, 161: 4702-4708 (1998).
Kong, S.Y., et al., "Daratumumab Directly Induces Human Multiple Myeloma Cell Death and Acts Synergistically with Conventional and Novel Anti-Myeloma Drugs," Blood, vol. 116; Abstract 3013 (2010).
Konopleva, et al., "CD38 in Hematopoietic Malignancies," Chemical Immunol. Basel Karger, 75: 189-206 (2000).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Kreuger, et al., "Successful in vivo blockade of CD25 (high-affinity interleukin 2 receptor) on T cells by administration of humanized anti-Tac antibody to patients with psoriasis," Journal of American Academy of Dermatology, 41(3): 448-458 (2000).
Kropff, et al., "Bortezomib in combination with dexamethoasone for relapsed multiple myeloma," Leukemia Research, 29: 587-590 (2005).
Kumar, S. et al., "Expression of CD52 on plasma cells in plasma cell proliferative disorders," Blood, vol. 102; No. 3; 1075-1077 (2003).
Kupiec-Weglinski, "CD25-Targeted Therapy Revisited," Transplantation, 69(3): 328-330 (2000).
Lakshman, A. et al., "Efficacy of daratumumab-based therapies in patients with relapsed, refractory multiple myeloma treated outside of clinical trials," Am J. Hematol., vol. 92; 1146-1155 (2017).
Lande, et al., "CD38 ligation plays a direct role in the induction of IL-1β, I-6, and IL-10 secretion in resting human monocytes," Cellular Immunology, 220: 30-38 (2002).
Laubach, J.P., "Daratumumab granted breakthrough drug status," Expert Opinion Investig. Drugs, vol. 23; No. 4; 445-452 (2014).
Laurie, et al., "The role of CD4+CD25+ immunoregulatory T cells in the induction of autoimmune gastritis," Immunology and Cell Biology, 80: 567-573 (2002).
Lazar, et al., "Transforming Growth Factor α: Mutation of Aspartic Acid 47 and Leucine 48 Results in Different Biological Activities," Molecular and Cellular Biology, 8(3): 1247-1252 (1988).
Leonard, et al., "Molecular cloning and expression of cDNAs for the human interleukin-2 receptor," Nature 311(18): 626-631 (1984).
Leveque "Subcutaneous Administration of Anticancer Agents" Anticancer Research, Departments of Pharmacy, University Hospital, Strasbourg, France, vol. 34, pp. 1579-1586 (2014).

Li, et al., "Creation of Patient Derived AML Xenografts Displaying Distinct Phenotypes and Genotypes," Blood, vol. 122: No. 21, p. 5018 (2013).
Lin, et al., "Structure-Function Relationships in Glucagon: Properties of Highly Purified Des-His1-, Monoiodi-, and [Des-Asn28, Thr29](homoserine lactone27)-glucagon," Biochemistry, 14(9): 1559-1563 (1975).
Lippincott-Schwartz, "Antibodies as cell Biological Tools," Current Protocols in Cell Biology, 16.0.1-16.0.2, (2002).
Liu et al., "Induction of Chemoresistance by All-Trans Retinoic Acid via a Noncanonical Signaling in Multiple Myeloma Cells," PLOS One, vol. 9, No. 1, page Article No. e85571, Jan. 2014.
Lonberg, et al., "Antigen-specific human antibodies from mice comprising four distinct genetic modifications," Nature: 308: 856-859 (1994).
Lu et al., "Issues Related to Targeted Delivery of Proteins & Peptides," The AAPS Journal, vol. 8, No. 3, Article 55, pp. E466-E478, Jul. 21, 2006.
MacCallum, et al., "Antibody-antigen Interactions: Contact Analysis and Binding Site Topography," Journal of Molecular Biology, 262, 732-745 (1998).
Malavasi, et al., "Human CD38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
Matas-Cespedes, A. et al., "The human CD38 monoclonal antibody daratumumab shows anti-tumor activity and hampers leukemia-microenvironment interactions in chronic lympocytic leukemia," Clinical Cancer Research, vol. 23; No. 6; 1493-1505 (2017).
McCarthy, P.L., "Strategies for induction, autologous hematopoietic stem cell transplantation, consolidation, and maintenance for transplantation-eligible multiple myeloma patients", Hematology, vol. 2013, NI. 1, pp. 496-503 (Dec. 2013).
McKelvey, et al., "Hydroxyldaunomycian (Adriamycin) Combination Chemotherapy in Malignant Lymphoma," Cancer, vol. 38, No. 4, pp. 1485-1493 (Oct. 1976).
Mills, et al., Characterization of Monoclonal Antibodies that Inhibit CD38 ADp-ribosyl Cyclase Activity, LSSURP HLB Program, Department of Pharmacology, University of Minnesota, 2007.
Mikhael et al., "Cyclophosphamide-Bortezomib-Dexamethasone (CYBORD) Produces Rapid and Complete Hematological Response in Patients with AL Amyloidosis," Blood 119:4391-94 (Year: 2012).
Mohammad et al., "The Addition of Bryostatin 1 to Cyclophosphamide, Doxorubicin, Vincristine, and Prednisone (CHOP) Chemotherapy Improves Response in a CHOP-resistant Human Diffuse Large Cell Lymphoma Xenograft Model," Clinical Cancer Research, vol. 6, 4950-4956 (Dec. 2000).
Morrison, et al., "Chimeric human antibody molecules: Mouse antigen-binding domains with human constant region domains," Proceedings of the National Academy of Science USA, vol. 81; 6851-6855 (1984).
Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, "Single domain camel antibodies: current status," Reviews in molecular Biotechnology, 74: 277-302 (2001).
Muyldermans, et al., "Recognition of antigens by single-domain antibody fragments: the superfluous luxury of paired domains," Trends in Biochemical Sciences, 26(4): 230-235 (2001).
Najjar et al., "Abstract P227: Accumulation of MDSC Subsets in Renal Cell Carcinoma Correlates with Grade and Progression Free Survival, and is Associated with Intratumoral Expression of IL-1β, IL-8 and CXCLS," Journal for Immunotherapy of Cancer, Nov. 6, 2014, vol. 2, p. 110-112.
Nijhof, et al.,"Modulation of CD 38 Expression Levels on Multiple Myeloma Tumor Cells by All-Trans Retinoic Acid Improves the Efficacy of the Anti-CD 38 Monoclonal Antibody Daratumumab," Blood, American Society of Hematology, US, vol. 124, No. 21, p. 2096, Dec. 6, 2014. (Abstract Only).
Nijhof, I.S. et al., Combination of the anti-CD38 monoclonal antibody daratumumab and all-trans retinoic acid (Abstract in

(56) References Cited

OTHER PUBLICATIONS

Proceedings of the AACR Special Conference on Hematologic Malignancies: Translating Discoveries to Novel Therapies). Clin Cancer Res, Sep. 20, 2014, vol. 21, No. 17 Suppl, pages Abstract A12; Abstract.
Nijhof I.S. et al.: "Upregulation of CD38 expression on multiple myeloma cells by all-trans retinoic acid improves the efficacy of daratumumab", Leukemia, vol. 29, No. 10, ISSN 1476-5551, pp. 2039-2049 (2015).
Nikaido, et al., "Molecular cloning of cDNA encoding human interleukin-2 receptor," Nature, 311: 631-635 (1984).
Offidani et al., "An evidence-based review of ixazomib citrate and its potential in the treatment of newly diagnosed multiple myeloma," OncoTargets and Therapy, vol. 7, pp. 1793-1800, 2014.
Onizuka, et al., "Tumor Rejection by in Vivo Administration of Anti-CD25 (Interleukin-2 Receptor α Monoclonal Antibody," Cancer Research, 59: 3128-3133 (1999).
Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Palumbo, A. et al., "Daratumumab, Bortezomib, and Dexamethasone for Multiple Myeloma," The New England Journal of Medicine, vol. 375; No. 8; 754-766 (2016).
Parren et al., "HuMax-CD38, a new human CD38 monoclonal antibody, effectively mediates killing of multiple myeloma and plasma cell leukemia cells," American Society of Hematology 47th annual meeting, Atlanta, Georgia, USA, Dec. 10-13, 2005 (Abstract).
Parren, et al., HuMax-CD38, Myconos, Jun. 26, 2006.
Parren, et al., HuMax-CD38, Torino, Jun. 8-10, 2006.
Pascual, et al., "Anti-interleukin-2 receptor antibodies: basiliximab and daclizumab," Nephrology Dial. Transplant, 16: 1756-1760 (2001).
Paul, M.D., "Fundamental Immunology," Chapter 9, Raven Press, New York, 3rd ed., 292-295 (1993).
Peipp, et al., "Fully Human CD38 Antibodies Efficiently Trigger ADCC and CDC of Multiple Myeloma Cell Lines and Primary Tumor Cells (Poster)," Blood, vol. 106(11): 944A, 47th Annual Meeting of the American Society of Hematology, 2005; published (Nov. 16, 2005).
Peipp, et al., Fully Human CD38 Antibodies Efficiently Trigger ADCC and CDC of Multiple Myeloma and Plasma Cell Leukemia Cells (Poster 2) Conference proceedings, poster presentation at the 2005 Annual Meeting of the American Society of Hematology, (Dec. 12, 2005).
Peipp, et al., 47th Annual Meeting of the American Society of Hematology, Atlanta, GA, Dec. 10-13 (2005). (Meeting Abstract).
Peng, et al., "Oncolytic measles viruses displaying a single-chain antibody against CD38, a myeloma cell marker," Blood, 101, 2557-2562 (2003).
Phase 1/2 Dose Escalation and Efficacy Study of Anti-CD38 Monoclonal Antibody in Patients With Selected CD38+ Hematological Malignancies, First posted Mar. 10, 2010, ClinicalTrials.gov. identifier No. NCT01084252.
Prosniak, M. et al.: "Development of a Cocktail of Recombinant-Expressed Human Rabies Virus-Neutralizing Monoclonal Antibodies for Postexposure Prophylaxis of Rabies," The Journal of Infectious Diseases, vol. 187; 53-56 (2003).
Richardson, et al., "Daratumumab," Drugs of the Future, 38(8): 545-554 (2013).
Rituxan Hycela Label, "Highlights of prescribing information. RITUXAN HYCELA™ (rituximab and hyaluronidase human) injection, for subcutaneous use," 32 pages (Jun. 2017).
Sachchithanantham, S. et al., "Use of Plasma Cell Immunophenotype as Prognostic Markers in Patients with Systemic AL Amyloidosis," Blood, vol. 122; p. 3120 (2013).
Salar et al., "Comparison of Subcutaneous Versus Intravenous Administration of Rituximab as Maintenance Treatment for Follicular Lymphoma: Results From a Two-Stage, Phase IB Study," Journal of Clinical Oncology, vol. 32, No. 17, pp. 1782-1791, (Jul. 10, 2014).
Sanchez-Gonzalez et al., "Rituximab subcutaneous in B-Cell non-Hodgkin lymphoma: clinical experience in a single center," Leukemia & Lymphoma, vol. 59, No. 4, pp. 1019-1021 (2018).
San-Miguel, J. et al., "Efficacy by cytogenetic risk status for daratumumab in combination with lenalidomide and dexamethasone or bortezomib and dexamethasone in relapsed or refractory multiple myeloma," EHA22; EHA Learning Center; Abstract; 4 pages (2017).
San-Miguel, J., "New approaches to myeloma treatment in 2017," EHA Learning Center; Abstract; 4 pages (2017).
Schonland, S., et al., "Detection and Charaterization of Plasma Cell and B Cell Clones in Patients with Systemic Light Chain Amyloidosis Using Flow Cytometry," Blood, vol. 142, p. 2068 (2014).
Shields, et al., "High Resolution mapping of the binding site on human IgG1 for FcγRi, FcγRII, FcγRIII, and FcRn and design of IgG1 variants with improved binding to the FcγR," J. Biol. Chem., vol. 276, No. 9, pp. 6591-6604, (2001).
Shpilberg, et al., "Subcutaneous administration of rituximab (MabThera) and trastuzumab (Herceptin) using hyaluronidase," British Journal of Cancer, vol. 109, pp. 1556-1561, 2013.
Shubinsky, et al., "The CD38 Lymphocyte Differentiation Marker: New Insight into Its Ectoenzymatic Activity and Its Role as a Signal Transducer," Immunity, 7: 315-324 (1997).
Skeel, Handbook of Cancer Gliemotherapy, 3rd edition, Little, Brown & Co., pp. 330-350 (1991).
Sonneveld, P. and Annemiek Broijl, "Treatment of Relapsed and Refractory Multiple Myeloma," Review Article, Leaders in Hematology, review series, Haematologica, 101(4):396-406 (2016).
Spencer, A. et al., "Daratumumab plus bortezomib and dexamethasone versus bortezomib and dexamethasone in relapsed or refractory multiple myeloma: updated analysis of CASTOR," Haematologica, vol. 103; No. 12; 2079-2087 (2018).
Strome, S.E. et al., "A Mechanistic Perspective of Monoclonal Antibodies in Cancer Therapy Beyond Target-Related Effects," The Oncologist, vol. 12; 1084-1095 (2007).
Tabernero, et al., "Adult precursor B-ALL with BCR/ABL gene rearrangements displays a unique immunophenotype based on the pattern of CD10, CD34, CD13, and CD38 expression," Leukemia, vol. 15, No. 3, pp. 406-414, (2001).
Terhorst, et al., "Biochemical Studies of the Human Thymocyte Cell-Surface Antigens T6, T9 and T10," Cell, 23: 771-780 (1981).
Topalian, S.L., et al., "Immune Checkpoint Blockade: A Common Denominator Approach to Cancer Therapy," Cancer Cell, vol. 27; 450-461 (2015).
Usmani, et al., "Clinical efficacy of daratumumab monotherapy in patients with heavily pretreated relapsed or refractory multiple myeloma," Blood, vol. 128, No. 1, pp. 37-44, (May 23, 2016).
Usmani, S.Z. et al., "Efficacy of Daratumumab, Lenalidomide, and Dexamethasone Versus Lenalidomide and Dexamethasone in Relapsed or Refractory Multiple Myeloma Patients with 1 to 3 Prior Lines of Therapy: Updated Analysis of Pollux," Blood, vol. 128; No. 22; 1151; 10 pages (2016).
Vadjos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).
Van Bueren, et al., "Direct In Vitro Comparison of Daratumumab With Surrogate Analogs of Anti-CD38 Antibodies," New Evidence Oncology Issue, Apr. 2015 [retrieved on Feb. 3, 2016] Retrieved from the Internet: URL: Http:///www.newevidence.com/oncology/direct-in-vitro-comparison-of-daratumumab-with-surrogate-analogs-of-anti-cd38-antibodies>.
Van de Donk et al., "Monoclonal antibodies targeting CD38 in hematological malignancies and beyond," Immunological Reviews, vol. 270, pp. 95-112, (2016).
Venner et al., "Cyclophosphamide, bortezomib, and dexamethasone therapy in AL amyloidosis is associated with high clonal response rates and prolonged progression-free survival," Blood, vol. 119, No. 9, pp. 4387-4390, (2012).

(56) References Cited

OTHER PUBLICATIONS

Vorre, et al., "Multiple Daratumumab Abstracts to be Presented at EHA," ArrayDiagnostica, Abstract Only (2014).
Wagner, V., et al., "Preclinical Efficacy of Sepantronium Bromide (YM155) in multiple myeloma is conferred by down regulation of Mcl-1," Oncotarget, 5(21): 10237-10250 (2014).
Wagner et al., Survivin in Multiple Myeloma: Prognostic and Therapeutic Implications, vol. 118, Article 137, 2011 (Abstract Only).
WCJ van de Donk, "A Phase 1 and Phase 2 Study of Daratumumab in Combination With All-Trans Retinoic Acid in Relapsed/Refractory Multiple Myeloma," Clinical Trials.gov Identification No. NCT02751255; (First posted Apr. 26, 2016).
Weisel, K.C. et al., "Efficacy of daratumumab in combination with lenalidomide plus dexamethasone (DRd) or bortezomib plus dexamethasone (RVd) in relapsed or refractory multiple myeloma (RRMM) based on cytogenetic risk status," Journal of Clinical Oncology, vol. 35; No. 15; 8006; Abstract (2017).
Ye et al, "Abstract P240: Treg Increases HepG2 Cell Growth by RANK-RANKL pathway." Journal for Immunotherapy of Cancer, vol. 2; Suppl 3; P240 (Nov. 6, 2014).
International Search Report and Written Opinion dated Feb. 12, 2019 for International Application No. PCT/US2018/058561, entitled "Methods of Treating High Risk Multiple Myeloma".
International Preliminary Report on Patentability dated May 8, 2018 for International Application No. PCT/US2016/59893, entitled "Subcutaneous Formulations of Anti-CD38 Antibodies and Their Uses".
International Search Report and Written Opinion dated Jan. 24, 2017 for International Application No. PCT/US2016/59893, entitled "Subcutaneous Formulations of Anti-CD38 Antibodies and Their Uses".
International Preliminary Report on Patentability dated Dec. 26, 2017 for International Application No. PCT/US2016/038702, entitled "Combination Therapies for Heme Malignancies With Anti-CD38 Antibodies and Survivin Inhibitors".
International Search Report and Written Opinion dated Nov. 29, 2016 for International Application No. PCT/US2016/038702, entitled "Combination Therapies for Heme Malignancies With Anti-CD38 Antibodies and Survivin Inhibitors".
International Preliminary Report on Patentability dated Mar. 14, 2017 for International Application No. PCT/US2015/048899, entitled "Combination Therapies With Anti-CD38 Antibodies".
International Search Report and Written Opinion dated Apr. 8, 2016 for International Application No. PCT/US2015/048899, entitled "Combination Therapies With Anti-CD38 Antibodies".
International Preliminary Report on Patentability dated Nov. 21, 2017 for International Application No. PCT/US2016/033544, entitled "Anti-CD38 Antibodies for Treatment of Light Chain Amyloidosis and Other CD38-Positive Hematological Malignancies".
International Search Report and Written Opinion dated Oct. 24, 2016 for International Application No. PCT/US2016/033544, entitled "Anti-CD38 Antibodies for Treatment of Light Chain Amyloidosis and Other CD38-Positive Hematological Malignancies".
International Preliminary Report on Patentability dated Jun. 6, 2016 for International Application No. PCT/US2015/063371, entitled "Anti-CD38 Antibodies for Treatment of Acute Myeloid Leukemia".
International Search Report and Written Opinion dated Feb. 19, 2016 for International Application No. PCT/US2015/063371, entitled "Anti-CD38 Antibodies for Treatment of Acute Myeloid Leukemia".
International Preliminary Report on Patentability dated Dec. 26, 2017 for International Application No. PCT/US2016/039165, entitled "Immune Modulation and Treatment of Solid Tumors With Antibodies That Specifically Bind CD38".
International Search Report and Written Opinion dated Oct. 14, 2016 for International Application No. PCT/US2016/039165, entitled "Immune Modulation and Treatment of Solid Tumors With Antibodies That Specifically Bind CD38".
International Preliminary Report on Patentability dated Sep. 6, 2016 for International Application No. PCT/US2015/017425, entitled "Anti-CD38 Antibodies for Treatment of Acute Leukemia".
International Search Report and Written Opinion dated Sep. 21, 2015 for International Application No. PCT/US2015/017425, entitled "Anti-CD38 Antibodies for Treatment of Acute Lymphoblastic Leukemia".
International Search Report and Written Opinion dated Sep. 25, 2017 for International Application No. PCT/EP2017/066063, entitled "Treatment of IgE-Mediated Diseases With Antibodies That Specifically Bind CD38".
International Preliminary Report on Patentability dated Sep. 6, 2016 for International Application No. PCT/US2015/017420, entitled "Combination Therapies With Anti-CD38 Antibodies".
International Search Report and Written Opinion dated Jul. 8, 2015 for International Application No. PCT/US2015/017420, entitled "Combination Therapies With Anti-CD38 Antibodies".
Intellectual Property Office of Singapore Written Opinion dated Apr. 17, 2018 for Application No. 11201701867S, entitled "Combination Therapies with Anti-CD38 Antibodies".
Supplementary European Search Report dated Feb. 21, 2018 for European Application No. EP 15839752, entitled "Combination Therapies with Anti-CD38 Antibodies".
Non Final Office Action for U.S. Appl. No. 15/340,290 dated Nov. 20, 2017.
Final Office Action for U.S. Appl. No. 15/340,290 dated May 16, 2018.
Non Final Office Action for U.S. Appl. No. 15/340,290 dated Oct. 10, 2018.
Non Final Office Action for U.S. Appl. No. 15/366,474 dated Nov. 20, 2017.
Final Office Action for U.S. Appl. No. 15/366,474 dated May 16, 2018.
Applicant Initiated Interview for U.S. Appl. No. 15/366,474 dated Sep. 17, 2018.
Non Final Office Action for U.S. Appl. No. 15/366,474 dated Oct. 11, 2018.
Non Final Office Action for U.S. Appl. No. 15/189,577 dated Oct. 31, 2017.
Final Office Action for U.S. Appl. No. 15/189,577 dated Apr. 13, 2018.
Non Final Office Action for U.S. Appl. No. 15/189,577 dated Sep. 28, 2018.
Non Final Office Action for U.S. Appl. No. 14/847,428 dated Sep. 23, 2016.
Non Final Office Action for U.S. Appl. No. 15/386,391 dated Jun. 18, 2018.
Non Final Office Action for U.S. Appl. No. 15/160,476 dated Sep. 15, 2017.
Non Final Office Action for U.S. Appl. No. 15/160,476 dated Nov. 5, 2018.
Final Office Action for U.S. Appl. No. 15/160,476 dated Apr. 23, 2018.
Non Final Office Action for U.S. Appl. No. 14/956,890 dated Nov. 25, 2016.
Final Office Action for U.S. Appl. No. 14/956,890 dated Jul. 24, 2018.
Non Final Office Action for U.S. Appl. No. 15/340,214 dated May 16, 2018.
Non Final Office Action for U.S. Appl. No. 14/629,965 dated Dec. 21, 2015.
Final Office Action for U.S. Appl. No. 14/629,965 dated Apr. 29, 2016.
Notice of Allowance for U.S. Appl. No. 14/629,965 dated Apr. 13, 2017.
Non Final Office Action for U.S. Appl. No. 15/445,225 dated Jun. 29, 2018.
Final Office Action for U.S. Appl. No. 15/445,225 dated Dec. 17, 2018.
Non Final Office Action for U.S. Appl. No. 15/651,333 dated Sep. 27, 2018.
Final Office Action for U.S. Appl. No. 15/386,391 dated Dec. 28, 2018.

(56) References Cited

OTHER PUBLICATIONS

Final Office Action for U.S. Appl. No. 14/956,890 dated Jan. 14, 2019.
Notice of Allowance for U.S. Appl. No. 15/651,333 dated Feb. 21, 2019.
Notice of Allowance for U.S. Appl. No. 15/189,577 dated Mar. 5, 2019.
Final Office Action for U.S. Appl. No. 15/340,290 dated Mar. 11, 2019.
The Cancer Genome Atlas Research Network et al., "Genomic and Epigenomic Landscapes of Adult De Novo Acute Myeloid Leukemia," N. Engl. J. Med, vol. 368; No. 22; 2059-2074 (2013).
Notice of Allowance for U.S. Appl. No. 15/189,577 dated Sep. 12, 2019.
Notice of Allowance for U.S. Appl. No. 15/651,333 dated Oct. 9, 2019.
Palumbo, A. et al., "Daratumumab, Bortezomib, and Dexamethasone for Multiple Myeloma," The New England Journal of Medicine, vol. 375; No. 8; 754-766; Suppl. Material: the protocol; total pages 119 (2016).
Final Office Action for U.S. Appl. No. 16/177,239 dated Feb. 10, 2021.
Non-Final Office Action for U.S. Appl. No. 15/798,670 dated Apr. 2, 2021.
Data show daratumumab achieved a pronounced overall response rate as a single-agent with tolerable safety profile in heavily pre-treated multiple myeloma patients, Johnson & Johnson Press release[online](retrieved on Jul. 27, 2020), May 30, 2015, retrieved from the InternetURL:https://www.jnj.com/media-center/press-releases/Data-show-daratumumab-achieved-a-pronounced-overall-response-rate-as-a-single-agent-with-tolerable-safety-profile-in-heavily-pre-treated-multiple-myeloma-patients; 4 pages.
de Haart, S.J. et al., "Accessory Cells of the Microenvironment Protect Multiple Myeloma from T-Cell Cytotoxicity through Cell Adhesion-Mediated Immune Resistance," Clinical Cancer Research, vol. 19; No. 20; 5591-5601 (2013).
DMC recommends termination of study into daratumumab with atezolizumab to treat NSCLC, European Pharmaceutic Manufacturer[online](retrieved on Jul. 26, 2020), May 30, 2018, retrieved from the InternetURL:https://www.epmmagazine.com/news/dmc-recommends-termination-of-study-into-daratumumab/; 3 pages.
Palumbo, A. et al., "Daratumumab, Bortezomib, and Dexamethasone for Multiple Myeloma," The New England Journal of Medicine, vol. 375; No. 8; 754-766; Suppl. Material: the protocol; total pp. 119 (2016).
Sagaster, V. et al., "Bortezomib in relapsed multiple myeloma: response rates and duration of response are independent of a chromosome 13q-deletion," Leukemia, vol. 21; 164-168 (2007).
Notice of Allowance for U.S. Appl. No. 14/956,890 dated Jul. 29, 2020.
Non-Final Office Action for U.S. Appl. No. 15/798,670 dated Aug. 7, 2020.
Notice of Allowance for U.S. Appl. No. 16/380,994 dated Aug. 12, 2020.
Non-Final Office Action for U.S. Appl. No. 16/177,239 dated Aug. 24, 2020.
Notice of Allowance for U.S. Appl. No. 16/460,754 dated Sep. 10, 2020.
Final Office Action for U.S. Appl. No. 15/798,670 dated Dec. 16, 2020.

\* cited by examiner

Figue 16E.
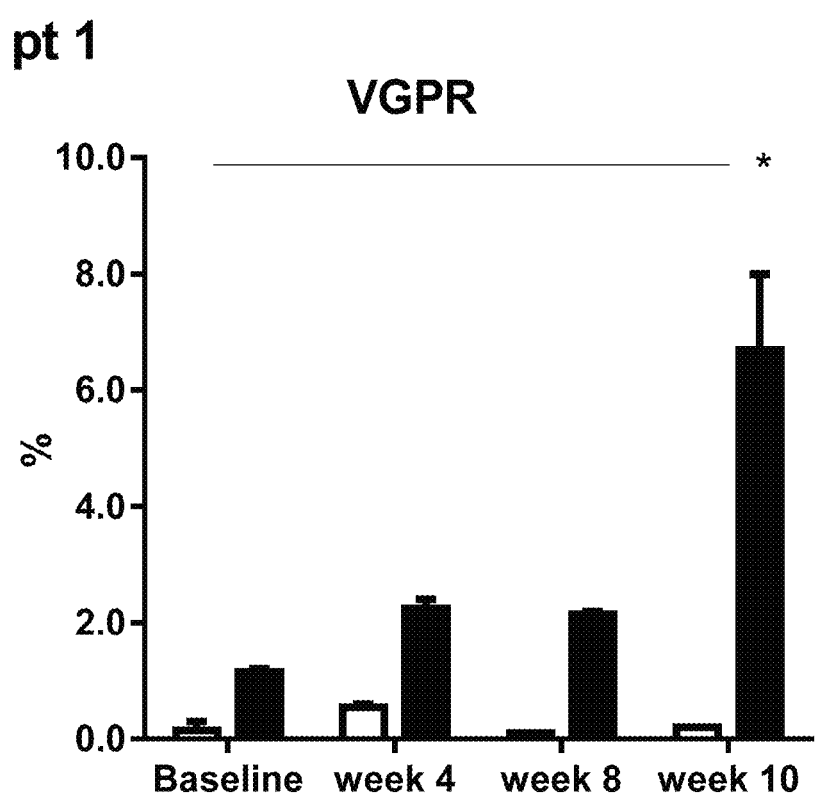

IMMUNE MODULATION AND TREATMENT OF SOLID TUMORS WITH ANTIBODIES THAT SPECIFICALLY BIND CD38

CROSS-REFERENCE TO RELATED APPLICATIONS

This application is a continuation of U.S. patent application Ser. No. 15/340,214, filed Nov. 1, 2016, which is a continuation-in-part of U.S. patent application Ser. No. 15/191,808, filed 24 Jun. 2016, which is now abandoned, which claims the benefit of U.S. Provisional Application No. 62/331,489 filed 4 May 2016, and U.S. Provisional Application No. 62/263,307, filed 4 Dec. 2015, and U.S. Provisional Application No. 62/250,566, filed 4 Nov. 2015, and U.S. Provisional Application No. 62/249,546, filed 2 Nov. 2015, and U.S. Provisional Application No. 62/184,018, filed 24 Jun. 2015, the entire contents of which are incorporated herein by reference.

SEQUENCE LISTING

This application contains a Sequence Listing submitted via EFS-Web in application Ser. No. 15/340,214 on Nov. 1, 2016, the entire content of which is incorporated herein by reference in its entirety. The ASCII text file, created on 29 Oct. 2016, is named JBI5067USCIPSEQLIST.txt and is 45 kilobytes in size.

FIELD OF THE INVENTION

The present invention relates to methods of immune modulation and treatment of solid tumors with antibodies that specifically bind CD38.

BACKGROUND OF THE INVENTION

The immune system is tightly controlled by a network of costimulatory and co-inhibitory ligands and receptors. These molecules provide secondary signals for T cell activation and provide a balanced network of positive and negative signals to maximize immune responses against infection and tumors, while limiting immunity to self (Wang et al., (Epub Mar. 7, 2011) *J Exp Med* 208(3):577-92; Lepenies et al., (2008) *Endocr Metab Immune Disord Drug Targets* 8:279-288).

Immune checkpoint therapy to treat solid tumors, targeting co-inhibitory pathways in T cells to promote antitumor immune responses, has led to advances in clinical care of cancer patients with approval of anti-CTLA-4 and anti-PD-1 antibodies YERVOY® (ipilimumab), KEYTRUDA® (pembrolizumab) and OPDIVO® (nivolumab). While anti-PD-1/PD-L1 antibodies are demonstrating encouraging clinical responses in patients with multiple solid tumors, the response rates are still fairly low, about 15%-20% in pretreated patients (Swaika et al., (2015) *Mol Immunol* doi: 10.1016/j.molimm.2015.02.009).

While natural killer cells (NK), dendritic cells (DC) and effector T cells are capable of driving potent anti-tumor responses, tumor cells often induce an immunosuppressive microenvironment, favoring the development of immunosuppressive populations of immune cells, such as myeloid-derived suppressor cells (MDSC), regulatory T-cells (Treg) or regulatory B-cells (Breg), which contribute to tumor immune tolerance and the failure of immunotherapy regimens in cancer patients and experimental tumor models.

Thus, there remains a need to develop new cancer immunotherapies that induce adaptive immune response against tumors or target the immunosuppressive immune cells.

SUMMARY OF THE INVENTION

The invention provides a method of treating a patient having a solid tumor comprising administering to the patient in need thereof a therapeutically effective amount of an antibody that specifically binds CD38.

The invention also provides a method for treating a patient having a regulatory T-cell (Treg) mediated disease comprising administering to the patient in need thereof a therapeutically effective amount of an antibody that specifically binds CD38.

The invention also provides a method for treating a patient having a myeloid-derived suppressor cell (MDSC) mediated disease comprising administering to the patient in need thereof a therapeutically effective amount of an antibody that specifically binds CD38.

The invention also provides a method for treating a patient having a regulatory B-cell (Breg) mediated disease comprising administering to the patient in need thereof a therapeutically effective amount of an antibody that specifically binds CD38.

The invention also provides a method of suppressing activity of a regulatory T-cell (Treg), comprising contacting the Treg with an antibody that specifically binds CD38.

The invention also provides method of suppressing activity of a myeloid-derived suppressor cell (MDSC), comprising contacting the MDSC with an antibody that specifically binds CD38.

The invention also provides a method of suppressing activity of a regulatory B-cell (Breg), comprising contacting the Breg with an antibody that specifically binds CD38.

The invention also provides a method of enhancing an immune response in a patient, comprising administering to the patient an antibody that specifically binds CD38.

The invention also provides a method of treating a patient having a solid tumor comprising reducing the number of Tregs cells in the patient by administering to the patient an antibody that specifically binds CD38.

The invention also provides a method of treating a patient having a solid tumor, comprising reducing the number of myeloid-derived suppressor cells (MDSC) in the patient by administering to the patient an antibody that specifically binds CD38.

The invention also provides a method of suppressing activity of an immune suppressor cell, comprising contacting the immune suppressing cell with an antibody that specifically binds CD38.

The invention also provides a method of treating a patient having a viral infection, comprising administering to the patient in need thereof an antibody that specifically binds CD38.

BRIEF DESCRIPTION OF THE DRAWINGS

FIG. 16E shows the percentage (%) of proliferating virus-reactive T cells in PBMCs from DARZALEX™ (daratumumab) treated patient with VGPR at baseline and at indicated times during treatment. White bar: negative control; black bar: CEF added. Asterix indicates a statistically significant change. Pre 4, 8, 10=Week 4, 8 or 10 of treatment.

DETAILED DESCRIPTION OF THE INVENTION

Figure 1:
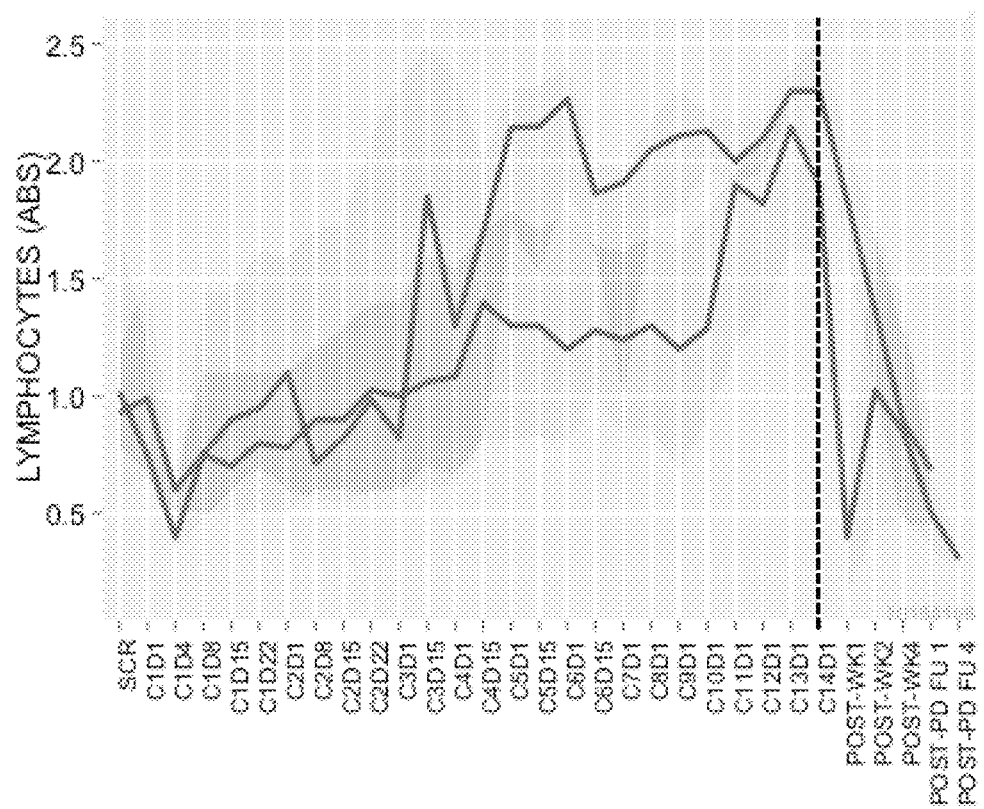
FIG. 1 shows that the median number of lymphocytes was increased in patients responding to DARZALEX™ (daratumumab) treatment at 8 mg/kg (upper line) or 16 mg/kg (lower line) doses over time, and that the lymphocyte numbers returned to baseline after end of treatment. Study: SIRIUS. X-axis indicates time expressed as treatment cycle and days of dosing within each treatment cycle (C1D1: cycle 1, day 1; C1D4; cycle 1, day 4, etc). SCR: baseline; EOT: end of treatment; WK: week; POST-WK: post-treatment at indicated weeks; post-PD FU: follow-up after progression. The highlighted areas in gray shades indicate the 25-27% Interquartile Range (IQR) for the data points for each visit for responders.

As used in this specification and the appended claims, the singular forms "a," "an," and "the" include plural referents unless the content clearly dictates otherwise. Thus, for example, reference to "a cell" includes a combination of two or more cells, and the like.

"CD38" refers to the human CD38 protein (synonyms: ADP-ribosyl cyclase 1, cADPr hydrolase 1, cyclic ADP-ribose hydrolase 1). Human CD38 has an amino acid sequence shown in GenBank accession number NP_001766 and in SEQ ID NO: 1. It is well known that CD38 is a single pass type II membrane protein with amino acid residues 1-21 representing the cytosolic domain, amino acid residues 22-42 representing the transmembrane domain, and residues 43-300 representing the extracellular domain of CD38.

SEQ ID NO: 1
MANCEFSPVSGDKPCCRLSRRAQLCLGVSILVLILVVVLAVVVPRWRQQW

SGPGTTKRFPETVLARCVKYTEIHPEMRHVDCQSVWDAFKGAFISKHPCN

ITEEDYQPLMKLGTQTVPCNKILLWSRIKDLAHQFTQVQRDMFTLEDTLL

GYLADDLTWCGEFNTSKINYQSCPDWRKDCSNNPVSVFWKTVSRRFAEAA

CDVVHVMLNGSRSKIFDKNSTFGSVEVHNLQPEKVQTLEAWVIHGGREDS

RDLCQDPTIKELESIISKRNIQFSCKNIYRPDKFLQCVKNPEDSSCTSEI

"Antibodies" as used herein is meant in a broad sense and includes immunoglobulin molecules including monoclonal antibodies including murine, human, humanized and chimeric monoclonal antibodies, antibody fragments, bispecific or multispecific antibodies, dimeric, tetrameric or multimeric antibodies, single chain antibodies, domain antibodies and any other modified configuration of the immunoglobulin molecule that comprises an antigen binding site of the required specificity.

Immunoglobulins may be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species can be assigned to one of two clearly distinct types, namely kappa (κ) and lambda (λ), based on the amino acid sequences of their constant domains.

"Antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CH1 domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a domain antibody (dAb) fragment (Ward et al., Nature 341:544-6, 1989), which consists of a VH domain. VH and VL domains may be engineered and linked together via a synthetic linker to form various types of single chain antibody designs in which the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Intl. Pat. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

"Isolated antibody" refers to an antibody or antibody fragment that is substantially free of other antibodies having different antigenic specificities (e.g., an isolated antibody specifically binding CD38 is substantially free of antibodies that specifically bind antigens other than human CD38). An isolated antibody that specifically binds CD38, however, may have cross-reactivity to other antigens, such as orthologues of human CD38, such as *Macaca fascicularis* (cynomolgus) CD38. In case of a bispecific antibody, the bispecific antibody specifically binds two antigens of interest, and is substantially free of antibodies that specifically bind antigens other that the two antigens of interest. Moreover, an isolated antibody may be substantially free of other cellular material and/or chemicals. "Isolated antibody" encompasses antibodies that are isolated to a higher purity, such as antibodies that are 80%, 81%, 82%, 83%, 84%, 85%, 86%, 87%, 88%, 89%, 90%, 91%, 92%, 93%, 94%, 95%, 96%, 97%, 98%, 99% or 100% pure.

"Specific binding" or "specifically binds" or "binds" refers to an antibody binding to an antigen or an epitope within the antigen with greater affinity than for other antigens. Typically, the antibody binds to the antigen or the epitope within the antigen with an equilibrium dissociation constant ($K_D$) of about $1\times10^{-8}$ M or less, for example about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a non-specific antigen (e.g., BSA, casein). The dissociation constant may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset). While a monospecific antibody specifically binds one antigen or one epitope, a bispecific antibody specifically binds two distinct antigens or two distinct epitopes.

An antibody variable region consists of a "framework" region interrupted by three "antigen binding sites". The antigen binding sites are defined using various terms: Complementarity Determining Regions (CDRs), three in the VH (HCDR1, HCDR2, HCDR3) and three in the VL (LCDR1, LCDR2, LCDR3) are based on sequence variability (Wu and Kabat (1970) *J Exp Med* 132:211-50; Kabat et al Sequences of Proteins of Immunological Interest, 5th Ed. Public Health Service, National Institutes of Health, Bethesda, Md., 1991); "Hypervariable regions", "HVR", or "HV", three in the VH (H1, H2, H3) and three in the VL (L1, L2, L3) refer to the regions of antibody variable domains which are hypervariable in structure as defined by Chothia and Lesk (Chothia and Lesk (1987) *Mol Biol* 196:901-%17). Other terms include "IMGT-CDRs" (Lefranc et al., (2003) *Dev Comparat Immunol* 27:55-77) and "Specificity Determining Residue Usage" (SDRU) (Almagro (2004) *Mol Recognit* 17:132-43). The International ImMunoGeneTics (IMGT) database provides a standardized numbering and definition of antigen-binding sites. The correspondence between CDRs, HVs and IMGT delineations is described in Lefranc et al., (2003) *Dev Comparat Immunol* 27:55-77.

"Chothia residues" as used herein are the antibody VL and VH residues numbered according to Al-Lazikani (Al-Lazikani et al., (1997) *J Mol Biol* 273:927-48).

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin wherein the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci. A "human antibody" may contain amino acid differences when compared to the human germline immunoglobulin or rearranged immunoglobulin genes due to for example naturally occurring somatic mutations or intentional introduction of substitutions in the framework or antigen binding site, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) *J Mol Biol* 296:57-86, or synthetic HCDR3 incorporated into human immunoglobulin gene libraries displayed on phage, for example as described in Shi et al., (2010) *J Mol Biol* 397:385-96, and Intl. Pat. Publ. No. WO2009/085462.

Human antibodies derived from human immunoglobulin sequences may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

Antibodies in which antigen binding sites are derived from a non-human species are not included in the definition of human antibody.

"Recombinant antibody" includes all antibodies that are prepared, expressed, created or isolated by recombinant means, such as antibodies isolated from an animal, for example a mouse or a rat that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

"Monoclonal antibody" refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes. "Monoclonal antibody" therefore refers to an antibody population with single amino acid composition in each heavy and each light chain, except for possible well known alterations such as removal of C-terminal lysine from the antibody heavy chain. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Epitope" means a portion of an antigen to which an antibody specifically binds. Epitopes usually consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or noncontiguous amino acids that form a conformational spatial unit. For a noncontiguous epitope, amino acids from differing portions of the linear sequence of the antigen come in close proximity in 3-dimensional space through the folding of the protein molecule.

"Variant" refers to a polypeptide or a polynucleotide that differs from a reference polypeptide or a reference polynucleotide by one or more modifications for example, substitutions, insertions or deletions.

"In combination with" means that two or more therapeutics are administered to a subject together in a mixture, concurrently as single agents or sequentially as single agents in any order. In general, each agent will be administered at a dose and/or on a time schedule determined for that agent.

"Treat" or "treatment" refers to therapeutic treatment wherein the object is to slow down (lessen) an undesired physiological change or disease, such as the development or spread of tumor or tumor cells, or to provide a beneficial or desired clinical outcome during treatment. Beneficial or desired clinical outcomes include alleviation of symptoms, diminishment of extent of disease, stabilized (i.e., not worsening) state of disease, delay or slowing of disease progression, lack of metastasis, amelioration or palliation of the disease state, and remission (whether partial or total), whether detectable or undetectable. "Treatment" may also mean prolonging survival as compared to expected survival if a subject was not receiving treatment. Those in need of treatment include those subjects already with the undesired physiological change or disease as well as those subjects prone to have the physiological change or disease.

"Therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics include, for example, improved well-being of the patient, reduction in a tumor burden, arrested or slowed growth of a tumor, and/or absence of metastasis of cancer cells to other locations in the body.

"Inhibits growth" (e.g. referring to tumor cells) refers to a measurable decrease or delay in the tumor cell growth or tumor tissue in vitro or in vivo when contacted with a therapeutic or a combination of therapeutics or drugs, when compared to the decrease or delay in the growth of the same tumor cells or tumor tissue in the absence of the therapeutic or the combination of therapeutic drugs. Inhibition of growth of a tumor cell or tumor tissue in vitro or in vivo may be at least about 10%, 20%, 30%, 40%, 50%, 60%, 70%, 80%, 90%, 99%, or 100%.

"Regulatory T cells" or "Tregs" or "Treg" refers to T lymphocytes that regulates the activity of other T cell(s) and/or other immune cells, usually by suppressing their activity. The Tregs may be CD3$^+$CD4$^+$CD25$^+$CD127$^{dim}$ T cells. It is appreciated that the Tregs may not be fully restricted to this phenotype, and may express Foxp3.

"Effector T cells" or "Teffs" or "Teff" refers to T lymphocytes that carry out a function of an immune response, such as killing tumor cells and/or activating an anti-tumor immune-response which can result in clearance of the tumor cells from the body. The Teffs may be CD3$^+$ with CD4$^+$ or CD8$^+$. The Teffs may secrete, contain or express markers such as IFN-γ, granzyme B and ICOS. It is appreciated that the Teffs may not be fully restricted to these phenotypes.

"Function of Tregs" or "Treg function" refers to a suppressive function of the Tregs that relates to regulation of host immune responses and/or prevention of autoimmunity. Function of Tregs may be suppression of an anti-tumor response elicted by CD8$^+$ T cells, natural killer (NK) cells, MØ cells, B cells, or dendritic cells (DCs), or suppression of proliferation of effector T cells.

"Inhibit function of Tregs" or "inhibit Treg function" refers to decreasing the level of function of Tregs in vitro or in vivo in an animal or human subject, which may be determined by conventional techniques known in the art. The level of the function of Tregs may be decreased by, for example, at least about 1%, 5%, 10%, 20%, 30%, 40%, 50%, 60%, 70%, 80%, 90%, 95%, 99% or 100%. "Inhibit function of Tregs" include reducing the number of Tregs, for example by killing the Tregs via antibody effector functions such as antibody-dependent cellular cytotoxicity (ADCC).

"Myeloid-derived suppressor cells" or "MDSCs" or "MDSC" refers to a specialized population of cells that are of the hematopoietic lineage and express the macrophage/monocyte marker CD11b and the granulocyte marker Gr-1/Ly-6G. Phenotype of the MDSCs may be for example CD11b+HLA-DR$^-$CD14$^-$CD33$^+$CD15$^+$. The MDSCs express low or undetectable expression of the mature antigen presenting cell markers MHC Class II and F480. The MDSCs are immature cells of the myeloid lineage and may further differentiate into several cell types, including macrophages, neutrophils, dendritic cells, monocytes or granulocytes. The MDSCs may be found naturally in normal adult bone marrow of human and animals or in sites of normal hematopoiesis, such as the spleen.

"Inhibit function of MDSCs" or "inhibit MDSC function" refers to decreasing the level of function of MDSCs in vitro or in vivo in an animal or human subject, which may be determined by conventional techniques known in the art. The level of the function of MDSC may be decreased by, for example, at least about 1%, 5%, 10%, 20%, 30%, 40%, 50%, 60%, 70%, 80%, 90%, 95%, 99% or 100%. "Inhibit function of MDSC" include reducing the number of MDSC, for example by killing the MDSC via antibody effector functions, such as ADCC. The MDSCs may suppress T cell responses such as proliferation, clonal expansion or cytokine production by various mechanisms such as production of reactive oxygen species, peroxynitrites, increased arginase metabolism due to high levels of arginase, and increased nitrous oxide synthase. The MDSCs may response to IFN-γ and several cytokines such as IL-4 and IL-13. IFN-γ may activate MDSCs which induces the activity of nitric-oxide synthase 2 (NOS2). Alternately, Th2 cytokines such as interleukin-4 (IL-4) and IL-13 may activate MDSCs which may lead to the induction of arginase-1 (ARG1) activity. The metabolism of L-arginine by either NOS2 or ARG1 may lead to the inhibition of T-cell proliferation, and the activity of both enzymes together can result in T-cell apoptosis through the production of reactive nitrogen-oxide species.

"Treg related disease" refers to a disease or disorder linked to T regulatory cells (Tregs). Treg related disease may be caused by Treg function, for example, suppression of an anti-tumor response or suppression of effector T cell proliferation. The Treg mediated disease may be cancer. "Treg related disease" and "Treg mediated disease" are used exchangeably herein.

"Enhance response of effector T cells" or "enhance T cell responses" refers to enhancement or stimulation of effector T cells in vitro or in vivo in an animal or human subject to have a sustained or amplified biological function, or renew or reactivate exhausted or inactive T-cells. Exemplary T-cell responses are proliferation, secretion of γ-interferon from CD 8$^+$ T-cells, antigen responsiveness, or clonal expansion. The manner of measuring this enhancement is known to one of ordinary skill in the art.

"MDSC related disease" refers to a disease or disorder linked to myeloid-derived suppressor cells (MDSCs). MDSC related disease may be caused by a MDSC function, for example, suppression of an anti-tumor response or effector T cell proliferation. The MDSC mediated disease may be cancer. "MDSC related disease" and "MDSC mediated disease" are used exchangeably herein.

"Regulatory B cell" or "Breg" or "Bregs" refers to B lymphocytes that suppress immune responses. The Bregs may be CD19$^+$CD24$^+$CD38$^+$ cells, and may suppress immune responses by inhibiting T cell proliferation mediated by IL-10 secreted by the Bregs. It is appreciated that other Breg subsets exists, and are described in for example Ding et al., (2015) *Human Immunology* 76: 615-621.

"Breg related disease" refers to a disease or disorder linked to regulatory B cells. Breg related disease may be caused by for example Breg mediated suppression of an anti-tumor response or effector T cell proliferation. The Breg mediated disease may be cancer. "Breg related disease" and "Breg mediated disease" are used exchangeably herein.

"Patient" includes any human or nonhuman animal. "Nonhuman animal" includes all vertebrates, e.g., mammals and non-mammals, such as nonhuman primates, sheep, dogs, cats, horses, cows chickens, amphibians, reptiles, etc. "Patient" and "subject" are used interchangeably herein.

The invention provides a method for treating a patient having a solid tumor with an antibody that specifically binds CD38 regardless whether the tumor cells express CD38 or not. The invention further provides methods for treating a patient having regulatory T cell (Treg), myeloid-derived suppressor cell (MDSC) or regulatory B cell (Breg) mediated disease. The invention further provides methods for modulating Treg, MDSC or Breg activity to treat solid tumors that are CD38 positive and/or associated with high levels of these immune suppressive cells.

The invention is based, at least in part, on the discovery that the anti-CD38 antibody DARZALEX™ (daratumumab) has an immunomodulatory activity in patients, reducing the number of immune suppressive Tregs, MDSCs and Bregs, increasing the number of CD8$^+$ T cells and the ratio of CD8$^+$ to Tregs, promoting CD8$^+$ central memory cell formation and increasing T cell clonality.

DARZALEX™ (daratumumab) and other anti-CD38 antibodies are being evaluated in the clinic for their efficacy to treat heme malignancies and plasma cell disorders, including multiple myeloma, by the ability of the antibody to eliminate CD38-positive cells by antibody effector functions, such as ADCC, CDC, ACDP and apoptosis, but their immunomodulatory activity in promoting adaptive immune responses has not been recognized. Other immune modulatory antibodies (anti-PD1, anti-CTLA4) function through targeting components of the immune system that suppress anti-tumor responses. For example, anti-PD1 antibodies have been demonstrated to increase T-cell proliferation, stimulate antigen-specific memory responses, and partially relieve Treg-mediated suppression of effector T cells in vitro (for example, see U.S. Pat. No. 8,779,105). Two anti-PD-1 antibodies are currently approved for treatment of melanoma, OPDIVO® (nivolumab) and KEYTRUDA® (pembrolizumab) and these antibodies are in clinical development for various solid tumors, such as lung non-small cell carcinoma, prostate, head and neck, gastrointestinal, stomach, prostate, fallopian tube, ovarian, pancreatic, breast and brain cancer, renal, bladder, urethral, oesophageal and colorectal cancer. Anti-CTLA-4 antibody YERVOY® (ipilimumab) has been approved for treatment of melanoma. YERVOY® (ipilimumab) and another anti-CTLA-4 antibody, tremelimumab are also being developed for prostate, non-small cell lung cancer, ovarian, gastrointestinal, stomach, colorectal, renal, oesophageal, and genitourinary cancer.

Without wishing to be bound by any particular theory, based on the immunomodulatory effects observed with DARZALEX™ (daratumumab) described herein, DARZALEX™ (daratumumab) and other anti-CD38 antibodies may be efficacious in treatment of solid tumors. Due to the general activation of immune response observed in patients treated with DARZALEX™ (daratumumab), patients having CD38-negative solid tumors may respond to anti-CD38 antibody therapies as well.

The invention provides for a method of treating a patient having a solid tumor, comprising administering to the patient in need thereof a therapeutically effective amount of an antibody that specifically binds CD38 for a time sufficient to treat the solid tumor.

The invention also provides for a method of treating a patient having a regulatory T cell (Treg) mediated disease, comprising administering to the patient in need thereof a therapeutically effective amount of an antibody that specifically binds CD38 for a time sufficient to treat the Treg mediated disease.

The invention also provides for a method of treating a patient having a myeloid-derived suppressor cell (MDSC) mediated disease, comprising administering to the patient in need thereof a therapeutically effective amount of an antibody that specifically binds CD38 for a time sufficient to treat the MDSC mediated disease.

The invention also provides for a method of treating a patient having a regulatory B cell (Breg) mediated disease, comprising administering to the patient in need thereof a therapeutically effective amount of an antibody that specifically binds CD38 for a time sufficient to treat the Breg mediated disease.

The invention also provides for a method of suppressing activity of a regulatory T cell (Treg), comprising contacting the regulatory T cell with an antibody that specifically binds CD38.

The invention also provides for a method of suppressing activity of a myeloid-derived suppressor cell (MDSC), comprising contacting the MDSC with an antibody that specifically binds CD38.

The invention also provides for a method of suppressing activity of a regulatory B cell (Breg), comprising contacting the Breg with an antibody that specifically binds CD38.

The invention also provides for a method of treating a patient having a solid tumor, comprising reducing the number of regulatory T cells (Treg) in the patient by administering to the patient an antibody that specifically binds CD38.

The invention also provides for a method of treating a patient having a solid tumor, comprising reducing the number of myeloid-derived suppressor cells (MDSC) in the patient by administering to the patient an antibody that specifically binds CD38.

The invention also provides for a method of treating a patient having a solid tumor, comprising reducing the number of regulatory B cells (Breg) in the patient by administering to the patient an antibody that specifically binds CD38.

The invention also provides for a method of enhancing an immune response in a patient, comprising administering to the patient in need thereof an antibody that specifically binds CD38 for a time sufficient to enhance the immune response.

In some embodiments, the patient has a viral infection.

The invention also provides for a method of treating a viral infection in a patient, comprising administering to the patient in need therefor an antibody that specifically binds CD38 for a time sufficient to treat the viral infection.

In some embodiments, the immune response is an effector T cell (Teff) response.

In some embodiments, the Teff response is mediated by $CD4^+$ T cells or $CD8^+$ T cells.

In some embodiments, the Teff response is mediated by $CD4^+$ T cells.

In some embodiments, the Teff response is mediated by $CD8^+$ T cells.

In some embodiments, the Teff response is an increase in the number of $CD8^+$ T cells, increased $CD8^+$ T cell proliferation, increased T cell clonal expansion, increased $CD8^+$ memory cell formation, increased antigen-dependent antibody production, or increased cytokine, chemokine or interleukin production.

Proliferation of T cells may be assessed for example by measuring the rate of DNA synthesis using tritiated thymidine or measuring production of interferon-γ (IFN-γ) in vitro, or measuring absolute number or percentage of T cells in a population of cells from patient samples using known methods.

Clonal expansion may be assessed by for example sequencing TCR from a pool of T cells using know methods.

Memory cell formation may be assessed by measuring the ratio of naïve T cells ($CD45RO^-/CD62L^+$) to memory T cells ($CD45RO^+/CD62L^{high}$) using for example FACS.

Cytokine, chemokine or interleukin production, such as production of interferon-γ (IFN-γ), tumor necrosis factor-alpha (TNF-α), IL-1, IL-2, IL-3, IL-4, IL-6, IL-8, IL-10, IL-12, IL-13, IL-16, IL-18 and IL-23, MIP-1α, MIP-1β, RANTES, CCL4 may be assessed using standard methods such as ELISA or ELLISPOT assay.

Antigen-specific antibody production may be assessed from samples derived from patient using standard methods, such as ELISA or radioimmunoassay (RIA).

The meaning of "increase" or "increasing" various Teff responses is readily understood. The increase may be increase of at least about 5%, at least about 10%, 25%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 200%, 250%, 300%, 350%, 400% or more in a test sample or in a subject when compared to control, e.g., for example in a patient treated with an anti-CD38 antibody when compared to the same patient before treatment, or in a patient or group of patients that are responsive to anti-CD38 antibody treatment when compared to a patient or a group of patients that are non-responsive to the same treatment. Typically, the increase is statistically significant.

Similarly, the meaning of "reduce" or "reducing" or "decreasing" or "decrease" the number of Tregs, MDSCs and/or Bregs is readily understood. The decrease may be at least about 10%, 25%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 200%, 250%, 300%, 350%, 400% or more in a test sample or in a subject when compared to control, e.g., for example in a patient treated with an anti-CD38 antibody when compared to the same patient before treatment, or in a patient or group of patients that are responsive to anti-CD38 antibody treatment when compared to a patient or a group of patients that are non-responsive to the same treatment. Typically, the decrease is statistically significant.

In some embodiments, the antibody that specifically binds CD38 inhibits function of immune suppressor cells.

In some embodiments, the immune suppressor cells are regulatory T cells (Tregs), myeloid-derived suppressor cells (MDSC) or regulatory B cells (Bregs).

In some embodiments, the Tregs are CD3$^+$CD4$^+$CD25$^+$CD127$^{dim}$ T cells.

In some embodiments, the CD3$^+$CD4$^+$CD25$^+$CD127$^{dim}$ cells express Foxp3.

In some embodiments, the CD3$^+$CD4$^+$CD25$^+$CD127$^{dim}$ T cells express CD38.

Treg function, such as their ability to suppress Teff cells, may be assessed using known methods, such as assessing the ability of Tregs to suppress Teff proliferation in mixed lymphocyte reaction (MLR).

Treg function may be inhibited by for example reducing the relative number of Tregs when compared to Teffs (e.g. increasing the ratio of CD8$^+$/Treg cells) by direct killing of Tregs or a sub-population of Tregs, such as CD38$^+$ Tregs.

In some embodiments, the Treg function is inhibited by killing the Treg cells.

In some embodiments, the Treg killing is mediated by antibody-induced antibody-dependent cell cytotoxicity (ADCC), antibody-dependent cell phagocytosis (ADCP), complement-dependent cytotoxicity (CDC) or apoptosis induced by an antibody specifically binding CD38.

In some embodiment, the Treg killing is mediated by ADCC.

In some embodiments, the CD38$^+$ Tregs are killed.

In some embodiments, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58% or 60% of Tregs are killed.

As CD38 is expressed only in a portion of Tregs and MDSCs, it is expected that treatment of patients with solid tumors will not result in systemic depletion of Tregs and MDSCs, therefore likely providing an improved safety profile.

In some embodiments, the MDSCs are CD11b$^+$HLA-DR$^-$CD14$^-$CD33$^+$CD15$^+$ cells.

In some embodiments, the CD11b$^+$HLA-DR$^-$CD14$^-$CD33$^+$CD15$^+$ MDSCs express CD38.

MDSC function may be inhibited for example by reducing the number of MDSCs by direct killing of the cells.

In some embodiments, the MDSC function is inhibited by killing the CD38$^+$ MDSC.

In some embodiments, the MDSC killing is mediated by antibody-induced antibody-dependent cell cytotoxicity (ADCC), antibody-dependent cell phagocytosis (ADCP), complement-dependent cytotoxicity (CDC) or apoptosis induced by the antibody that specifically binds CD38.

In some embodiments, the MDSC killing is mediated by ADCC.

In some embodiments, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58% or 60% of the MDSCs are killed.

In some embodiments, the Bregs are CD19$^+$CD24$^+$CD38$^+$ cells.

The Breg function may be inhibited for example by reducing the number of Bregs by direct killing of the Bregs.

In some embodiments, the Breg function is inhibited by killing the CD38$^+$ Bregs.

In some embodiments, the Breg killing is mediated by antibody-induced antibody-dependent cell cytotoxicity (ADCC), antibody-dependent cell phagocytosis (ADCP), complement-dependent cytotoxicity (CDC) or apoptosis induced by the antibody that specifically binds CD38.

In some embodiments, the Breg killing is mediated by ADCC.

In some embodiments, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58% or 60% of the Bregs are killed.

Tregs play a critical role in the maintenance of peripheral self-tolerance. Naturally occurring CD4$^+$CD25$^{hi}$ Tregs are produced in the thymus and express Foxp3, a transcriptional factor required for establishment and maintenance of Treg lineage identity and suppressor function. Tregs can accumulate at a disease site (e.g. within tumor), where they suppress the effector function of tumor antigen specific T cells, resulting in insufficient anti-tumor responses. Increased densities of tumor-infiltrating Foxp3$^+$ Tregs have been associated with poor prognosis in various solid tumors, including pancreatic, ovarian, and hepatocellular carcinoma. Depletion of Tregs results in enhanced antitumor immunity and tumor rejection in murine models but may also result in the development of autoimmune diseases.

Myeloid-derived suppressor cells (MDSC) are a heterogeneous population of early myeloid progenitors, immature granulocytes, macrophages, and dendritic cells at different stages of differentiation. They accumulate in large numbers in cancer patients and they have potent immunosuppressive functions, suppressing both the cytotoxic activities of natural killer cells (NK) and natural killer T cells (NKT), and the adaptive immune response mediated by CD8$^+$ T cells. While the mechanism of NK cell inhibition is currently not well-understood, multiple pathways are responsible for MDSC-mediated T cell suppression including production of arginase 1/ARG1 and upregulation of nitric oxide synthase 2 (NOS2). ARG1 and NOS2 metabolize L-arginine and either together or separately blocks the translation of the T cell CD3zeta chain, inhibits T cell proliferation, and promotes T cell apoptosis. Additionally, MDSCs secrete immunosuppressive cytokines and induce regulatory T cell development.

MDSC are induced by pro-inflammatory cytokines and are found in increased numbers in infectious and inflammatory pathological conditions. They accumulate in the blood, bone marrow, and secondary lymphoid organs of tumor-bearing mice and their presence in the tumor microenvironment has been suggested to have a causative role in promoting tumor-associated immune suppression.

MDSC have been described in patients with colon carcinoma, melanoma, hepatocellular carcinoma, head and neck squamous cell carcinoma, non-small cell lung carcinoma, renal cell carcinoma, pancreatic adenocarcinoma and breast carcinoma (Mandruzzato et al., (2009) *J Immunol* 182: 6562-6568; Liu et al., (2009) *J Cancer Res Clin Oncol* 136: 35-45; Ko et al., (2009) *Clin Cancer Res* 15: 2148-2157; Morse et al., (2009) *Expert Opin Biol Ther* 9: 331-339; Diaz-Montero et al., (2009) *Cancer Immunol Immunother* 58: 49-59; Corzo et al., (2009) *J Immunol* 182: 5693-5701). In cancer patients, Diaz et al (Diaz-Montero et al., (2009) *Cancer Immunol Immunother* 58: 49-59) propose that accumulation of MDSC correlates with more advanced disease and poor prognosis.

Tumor-infiltrating Bregs have been identified in solid tumors, and the Bregs may promote tumor growth and metastasis by various mechanisms such as suppressing the anti-tumor activity of $CD8^+$ T cells and NK cells, as described in for example Ding et al., (2015) *Human Immunology* 76:615-62.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcvRIIIa. Death of the antibody-coated target cell, such as CD38-expressing cells, occurs as a result of effector cell activity through the secretion of membrane pore-forming proteins and proteases. To assess ADCC activity of an antibody that specifically binds CD38, the antibody may be added to CD38-expressing cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include Tregs or MDSCs expressing CD38. In an exemplary assay, target cells are labeled with 20 µCi of $^{51}Cr$ for 2 hours and washed extensively. Cell concentration of the target cells may be adjusted to $1\times10^6$ cells/ml, and anti-CD38 antibodies at various concentrations are added. Assays are started by adding target cells at an effector:target cell ratio of 40:1. After incubation for 3 hr at 37° C. assays are stopped by centrifugation and $^{51}Cr$ release from lysed cells are measured in a scintillation counter. Percentage of cellular cytotoxicity may be calculated as % maximal lysis which may be induced by adding 3% perchloric acid to target cells.

"Antibody-dependent cellular phagocytosis" ("ADCP") refers to a mechanism of elimination of antibody-coated target cells by internalization by phagocytic cells, such as macrophages or dendritic cells. ADCP may be evaluated by using Tregs or MDSCs expressing CD38 as target cells engineered to express GFP or other labeled molecule. Effector:target cell ratio may be for example 4:1. Effector cells may be incubated with target cells for 4 hours with or without anti-CD38 antibody. After incubation, cells may be detached using accutase. Macrophages may be identified with anti-CD11b and anti-CD14 antibodies coupled to a fluorescent label, and percent phagocytosis may be determined based on % GFP fluorescent in the $CD11^+CD14^+$ macrophages using standard methods.

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes.

The ability of monoclonal antibodies to induce ADCC may be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs may be achieved using different methods reported to lead to the successful expression of relatively high defucosylated antibodies bearing the biantennary complex-type of Fc oligosaccharides such as control of culture osmolality (Konno et al., (2012) *Cytotechnology* 64:249-65), application of a variant CHO line Lec 13 as the host cell line (Shields et al., (2002) *J Biol Chem* 277:26733-26740), application of a variant CHO line EB66 as the host cell line (Olivier et al., (2010) *MAbs* 2(4), Epub ahead of print; PMID:20562582), application of a rat hybridoma cell line YB2/0 as the host cell line (Shinkawa et al., (2003) *J Biol Chem* 278:3466-3473), introduction of small interfering RNA specifically against the oc 1,6-fucosyltrasferase (FUT8) gene (Mori et al., (2004) *Biotechnol Bioeng* 88:901-908), or coexpression of β-1,4-N-acetylglucosaminyltransferase III and Golgi α-mannosidase II or a potent alpha-mannosidase I inhibitor, kifunensine (Ferrara et al., (2006) *J Biol Chem* 281:5032-5036; Ferrara et al., (2006) *Biotechnol Bioeng* 93:851-861; Xhou et al., (2008) *Biotechnol Bioeng* 99:652-65). ADCC elicited by anti-CD38 antibodies used in the methods of the invention, and in some embodiments of each and every one of the numbered embodiments listed below, may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

In some embodiments, the antibody that specifically binds CD38 comprises a substitution in the antibody Fc.

In some embodiments, the antibody that specifically binds CD38 comprises a substitution in the antibody Fc at amino acid positions 256, 290, 298, 312, 356, 330, 333, 334, 360, 378 or 430 (residue numbering according to the EU index).

In some embodiments, the antibody that specifically binds CD38 has a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some embodiments, the antibody that specifically binds CD38 has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%

Substitutions in the Fc and reduced fucose content may enhance the ADCC activity of the antibody that specifically binds CD38.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Intl. Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used herein refers to antibodies with fucose content of about 0%-15%.

"Normal fucose" or "normal fucose content" as used herein refers to antibodies with fucose content of about over 50%, typically about over 60%, 70%, 80% or over 85%.

In some embodiments, the antibody that specifically binds CD38 may induce killing of Tregs, MDSCs and/or Bregs by apoptosis. Methods for evaluating apoptosis are well known, and include for example annexin IV staining using standard methods. The anti-CD38 antibodies used in the methods of the invention may induce apoptosis in about 20%, 25%, 30%, 35%, 40%, 45%, 50%, 55%, 60%, 65%, 70%, 75%, 80%, 85%, 90%, 95% or 100% of cells.

In some embodiments, the Teffs or the immune suppressor cells reside in bone marrow or in peripheral blood.

In some embodiments, the Teffs or the immune suppressor cells reside in bone marrow.

In some embodiments, the Teffs or the immune suppressor cells reside in peripheral blood.

In some embodiments, the antibody that specifically binds CD38 increases the ratio of CD8$^+$ T cells to Tregs.

In some embodiments, the antibody that specifically binds CD38 increases the ratio of CD8$^+$ central memory cells to CD8$^+$ naïve cells. CD8$^+$ central memory cells can be identified as CD45RO$^+$/CD62L$^{+high}$ cells. CD8$^+$ naïve cells can be identified as CD45RO-/CD62L$^+$ cells.

In some embodiments, the antibody that specifically binds CD38 is a non-agonistic antibody.

A non-agonistic antibody that specifically binds CD38 refers to an antibody which upon binding to CD38 does not induce significant proliferation of a sample of peripheral blood mononuclear cells in vitro when compared to the proliferation induced by an isotype control antibody or medium alone.

In some embodiments, the non-agonistic antibody that specifically binds CD38 induces proliferation of peripheral blood mononuclear cells (PBMCs) in a statistically insignificant manner. PBMC proliferation may be assessed by isolating PBMCs from healthy donors and culturing the cells at 1×10$^5$ cells/well in flat bottom 96-well plates in the presence or absence of a test antibody in 200 µl RPMI After four day incubation at 37° C., 30 µl $^3$H-thymidine (16.7 µCi/ml) may be added, and culture may be continued overnight. $^3$H-thymidine incorporation may be assessed using a Packard Cobra gamma counter (Packard Instruments, Meriden, DT, USA), according to the manufacturer's instructions. Data may be calculated as the mean cpm (±SEM) of PBMCs obtained from several donors. Statistical significance or insignificance between samples cultured in the presence or absence of the test antibody is calculated using standard methods.

An exemplary anti-CD38 antibody that may be used in the methods of the invention is DARZALEX™ (daratumumab). DARZALEX™ (daratumumab) comprises a heavy chain variable region (VH) and a light chain variable region (VL) amino acid sequences shown in SEQ ID NO: 4 and 5, respectively, a heavy chain complementarity determining region 1 (HCDR1), a HCDR2 and a HCDR3 of SEQ ID NOs: 6, 7 and 8, respectively, and a light chain complementarity determining region 1 (LCDR1), a LCDR2 and a LCDR3 of SEQ ID NOs: 9, 10 and 11, respectively, and is of IgG1/κ subtype and described in U.S. Pat. No. 7,829,693. DARZALEX™ (daratumumab) heavy chain amino acid sequence is shown in SEQ ID NO: 12 and light chain amino acid sequence shown in SEQ ID NO: 13.

In some embodiments, the antibody that specifically binds CD38 competes for binding to CD38 with an antibody comprising a heavy chain variable region (VH) of SEQ ID NO: 4 and a light chain variable region (VL) of SEQ ID NO: 5.

In some embodiments, the antibody that specifically binds CD38 binds at least to the region SKRNIQFSCKNIYR (SEQ ID NO: 2) and the region EKVQTLEAWVIHGG (SEQ ID NO: 3) of human CD38 (SEQ ID NO: 1).

```
                                                SEQ ID NO: 1
MANCEFSPVSGDKPCCRLSRRAQLCLGVSILVLILVVVLAVVVPRWRQQW

SGPGTTKRFPETVLARCVKYTEIHPEMRHVDCQSVWDAFKGAFISKHPCN

ITEEDYQPLMKLGTQTVPCNKILLWSRIKDLAHQFTQVQRDMFTLEDTLL

GYLADDLTWCGEFNTSKINYQSCPDWRKDCSNNPVSVFWKTVSRRFAEAA

CDVVHVMLNGSRSKIFDKNSTFGSVEVHNLQPEKVQTLEAWVIHGGREDS

RDLCQDPTIKELESIISKRNIQFSCKNIYRPDKFLQCVKNPEDSSCTSEI

SEQ ID NO: 2
SKRNIQFSCKNIYR
```

-continued

SEQ ID NO: 3
EKVQTLEAWVIHGG

SEQ ID NO: 4
EVQLLESGGGLVQPGGSLRLSCAVSGFTFNSFAMSWVRQAPGKGLEWVSA
ISGSGGGTYYADSVKGRFTISRDNSKNTLYLQMNSLRAEDTAVYFCAKDK
ILWFGEPVFDYWGQGTLVTVSS

SEQ ID NO: 5
EIVLTQSPATLSLSPGERATLSCRASQSVSSYLAWYQQKPGQAPRLLIYD
ASNRATGIPARFSGSGSGTDFTLTISSLEPEDFAVYYCQQRSNWPPTFGQ
GTKVEIK

SEQ ID NO: 6
SFAMS

SEQ ID NO: 7
AISGSGGGTYYADSVKG

SEQ ID NO: 8
DKILWFGEPVFDY

SEQ ID NO: 9
RASQSVSSYLA

SEQ ID NO: 10
DASNRAT

SEQ ID NO: 11
QQRSNWPPTF

SEQ ID NO: 12
EVQLLESGGGLVQPGGSLRLSCAVSGFTFNSFAMSWVRQAPGKGLEWVSA

ISGSGGGTYYADSVKGRFTISRDNSKNTLYLQMNSLRAEDTAVYFCAKDK

ILWFGEPVFDYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

SEQ ID NO: 13
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Antibodies may be evaluated for their competition with a reference antibody such as DARZALEX™ (daratumumab) having the VH of SEQ ID NO: 4 and the VL of SEQ ID NO: 5 for binding to CD38 using well known in vitro methods. In an exemplary method, CHO cells recombinantly expressing CD38 may be incubated with an unlabeled reference antibody for 15 min at 4° C., followed by incubation with an excess of fluorescently labeled test antibody for 45 min at 4° C. After washing in PBS/BSA, fluorescence may be measured by flow cytometry using standard methods. In another exemplary method, extracellular portion of human CD38 may be coated on the surface of an ELISA plate. Excess of the unlabeled reference antibody may be added for about 15 minutes and subsequently biotinylated test antibodies may be added. After washes in PBS/Tween, binding of the test biotinylated antibody may be detected using horseradish peroxidase (HRP)-conjugated streptavidin and the signal detected using standard methods. It is readily apparent that in the competition assays, the reference antibody may be labelled and the test antibody unlabeled. The test antibody competes with the reference antibody when the reference antibody inhibits binding of the test antibody, or the test antibody inhibits binding of the reference antibody to CD38 by at least 80%, for example 81%, 82%, 83%, 84%, 85%, 86%, 87%, 88%, 89%, 90%, 91%, 92%, 93%, 94%, 95%, 96%, 97%, 98%, 99% or 100%. The epitope of the test antibody may further be defined for example by peptide mapping or hydrogen/deuterium protection assays using known methods, or by crystal structure determination.

Antibodies binding to the region SKRNIQFSCKNIYR (SEQ ID NO: 2) and the region EKVQTLEAWVIHGG (SEQ ID NO: 3) of human CD38 (SEQ ID NO: 1) may be generated for example by immunizing mice with peptides having the amino acid sequences shown in SEQ ID NOs: 2 and 3 using standard methods and those described herein, and characterizing the obtained antibodies for binding to the peptides using for example ELISA or mutagenesis studies.

The invention also provides for a method of treating a patient having a solid tumor, comprising administering to the patient in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1). The epitope of the antibody used in the methods of the invention includes some or all of the residues having the sequences shown in SEQ ID NO: 2 or SEQ ID NO: 3. In some embodiments, the antibody epitope comprises at least one amino acid in the region SKRNIQFSCKNIYR (SEQ ID NO: 2) and at least one amino acid in the region EKVQTLEAWVIHGG (SEQ ID NO: 3) of human CD38 (SEQ ID NO: 1). In some embodiments, the antibody epitope comprises at least two amino acids in the region SKRNIQFSCKNIYR (SEQ ID NO: 2) and at least two amino acids in the region EKVQTLEAWVIHGG (SEQ ID NO: 3) of human CD38 (SEQ ID NO: 1). In some embodiments, the antibody epitope comprises at least three amino acids in the region SKRNIQFSCKNIYR (SEQ ID NO: 2) and at least three amino acids in the region EKVQTLEAWVIHGG (SEQ ID NO: 3) of human CD38 (SEQ ID NO: 1).

In some embodiments, the antibody that specifically binds CD38 comprises the HCDR1, the HCDR2 and the HCDR3 amino acid sequences of SEQ ID NOs: 6, 7 and 8, respectively.

In some embodiments, the antibody that specifically binds CD38 comprises the LCDR1, the LCDR2 and the LCDR3 amino acid sequences of SEQ ID NOs: 9, 10 and 11, respectively.

In some embodiments, the antibody that specifically binds CD38 comprises the HCDR1, the HCDR2, the HCDR3, the LCDR1, the LCDR2 and the LCDR3 amino acid sequences of SEQ ID NOs: 6, 7, 8, 9, 10 and 11, respectively.

In some embodiments, the antibody that specifically binds CD38 comprises the VH that is 95%, 96%, 97%, 98%, 99% or 100% identical to SEQ ID NO: 4 and the VL that is 95%, 96%, 97%, 98%, 99% or 100% identical to SEQ ID NO: 5.

In some embodiments, the antibody that specifically binds CD38 comprises the VH of SEQ ID NO: 4 and the VL of SEQ ID NO: 5.

In some embodiments, the antibody that specifically binds CD38 comprises the heavy chain of SEQ ID NO: 12 and the light chain of SEQ ID NO: 13.

Other exemplary anti-CD38 antibodies that may be used in any embodiment of the invention are:

mAb003 comprising the VH and the VL sequences of SEQ ID NOs: 14 and 15, respectively and described in U.S. Pat. No. 7,829,693. The VH and the VL of mAb003 may be expressed as IgG1/κ.

```
                                             SEQ ID NO: 14
QVQLVQSGAEVKKPGSSVKVSCKASGGTFSSYAFSWVRQAPGQGLEWMGR
VIPFLGIANSAQKFQGRVTITADKSTSTAY
MDLSSLRSEDTAVYYCARDDIAALGPFDYWGQGTLVTVSSAS

SEQ ID NO: 15
DIQMTQSPSSLSASVGDRVTITCRASQGISSWLAWYQQKPEKAPKSLIYA
ASSLQSGVPSRFSGSGSGTDFTLTISSLQP
EDFATYYCQQYNSYPRTFGQGTKVEIK;
``` mAb024 comprising the VH and the VL sequences of SEQ ID NOs: 16 and 17, respectively, described in U.S. Pat. No. 7,829,693. The VH and the VL of mAb024 may be expressed as IgG1/κ.

```
                                             SEQ ID NO: 16
EVQLVQSGAEVKKPGESLKISCKGSGYSFSNYWIGWVRQMPGKGLEWMGH
YPHDSDARYSPSFQGQVTFSADKSISTAY
LQWSSLKASDTAMYYCARHVGWGSRYWYFDLWGRGTLVTVSS

SEQ ID NO: 17
EIVLTQSPATLSLSPGERATLSCRASQSVSSYLAWYQQKPGQAPGLLIYD
ASNRASGIPARFSGSGSGTDFTLTISSLEPEDFAVYYCQQRSNWPLTFGG
GTKVEIK
```

MOR-202 (MOR-03087) comprising the VH and the VL sequences of SEQ ID NOs: 18 and 19, respectively, described in U.S. Pat. No. 8,088,896. The VH and the VL of MOR-202 may be expressed as IgG1/κ.

```
                                             SEQ ID NO: 18
QVQLVESGGGLVQPGGSLRLSCAASGFTFSSYYMNWVRQAPGKGLEWVSG
ISGDPSNTYYADSVKGRFTISRDNSKNTLY
LQMNSLRAEDTAVYYCARDLPLVYTGFAYWGQGTLVTVSS

SEQ ID NO: 19
DIELTQPPSVSVAPGQTARISCSGDNLRHYYVYWYQQKPGQAPVLVIYGD
SKRPSGIPERFSGSNSGNTATLTISGTQAE
DEADYYCQTYTGGASLVFGGGTKLTVLGQ;
```

Isatuximab; comprising the VH and the VL sequences of SEQ ID NOs: 20 and 21, respectively, described in U.S. Pat. No. 8,153,765. The VH and the VL of Isatuximab may be expressed as IgG1/κ.

```
SEQ ID NO 20:
QVQLVQSGAEVAKPGTSVKLSCKASGYTFTDYWMQWVKQRPGQGLEWIGT
IYPGDGDTGYAQKFQGKATLTADKSSKTVYMHLSSLASEDSAVYYCARGD
YYGSNSLDYWGQGTSVTVSS

SEQ ID NO: 21:
DIVMTQSHLSMSTSLGDPVSITCKASQDVSTVVAWYQQKPGQSPRRLIYS
ASYRYIGVPDRFTGSGAGTDFTFTISSVQAEDLAVYYCQQHYSPPYTFGG
GTKLEIK
```

Other exemplary anti-CD38 antibodies that may be used in the methods of the invention include those described in Intl. Pat. Publ. No. WO05/103083, Intl. Pat. Publ. No. WO06/125640, Intl. Pat. Publ. No. WO07/042309, Intl. Pat. Publ. No. WO08/047242 or Intl. Pat. Publ. No. WO14/178820.

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 14 and the VL of SEQ ID NO: 15 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 16 and the VL of SEQ ID NO: 17 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 18 and the VL of SEQ ID NO: 19 or a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 20 and the VL of SEQ ID NO: 21 or a time sufficient to treat the solid tumor.

In some embodiments, the solid tumor is a melanoma.

In some embodiments, the solid tumor is a lung cancer.

In some embodiments, the solid tumor is a squamous non-small cell lung cancer (NSCLC).

In some embodiments, the solid tumor is a non-squamous NSCLC.

In some embodiments, the solid tumor is a lung adenocarcinoma.

In some embodiments, the solid tumor is a renal cell carcinoma (RCC) (e.g., a kidney clear cell carcinoma or a kidney papillary cell carcinoma), or a metastatic lesion thereof.

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer or castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the solid tumor lacks detectable CD38 expression.

The solid tumor lacks detectable CD38 expression when CD38 expression in the solid tumor tissue or on cells isolated from the solid tumor is statistically insignificant when compared to a control, e.g. expression detected with anti-CD38 antibody vs expression detected with an isotype control antibody using well known methods.

Anti-CD38 antibodies used in the methods of the invention may also be selected de novo from, e.g., a phage display library, where the phage is engineered to express human immunoglobulins or portions thereof such as Fabs, single chain antibodies (scFv), or unpaired or paired antibody variable regions (Knappik et al., (2000) *J Mol Biol* 296:57-86; Krebs et al., (2001) *J Immunol Meth* 254:67-84; Vaughan et al., (1996) *Nature Biotechnology* 14:309-314; Sheets et al., (1998) *PITAS* (USA) 95:6157-6162; Hoogenboom and Winter, (1991) *J Mol Biol* 227:381; Marks et al., (1991) *J Mol Biol* 222:581). CD38 binding variable domains may be isolated from e.g., phage display libraries expressing antibody heavy and light chain variable regions as fusion proteins with bacteriophage pIX coat protein as described in Shi et al., (2010) *J Mol Biol* 397:385-96, and Intl. Pat. Publ. No. WO09/085462. The antibody libraries may be screened for binding to human CD38 extracellular domain, the obtained positive clones further characterized, Fabs isolated from the clone lysates, and subsequently cloned as full length antibodies. Such phage display methods for isolating human antibodies are established in the art. See for example: U.S. Pat. Nos. 5,223,409, 5,403,484, 5,571,698, 5,427,908, 5,580,717, 5,969,108, 6,172,197, 5,885,793, 6,521,404, 6,544,731, 6,555,313, 6,582,915, and 6,593,081.

In some embodiments, the anti-CD38 antibody is of IgG1, IgG2, IgG3 or IgG4 isotype.

The Fc portion of the antibody may mediate antibody effector functions such as antibody-dependent cell-mediated cytotoxicity (ADCC), antibody-dependent cellular phagocytosis (ADCP) or complement dependent cytotoxicity (CDC). Such function may be mediated by binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of target cells, for example CD38-expressing cells. Human IgG isotypes IgG1, IgG2, IgG3 and IgG4 exhibit differential capacity for effector functions. ADCC may be mediated by IgG1 and IgG3, ADCP may be mediated by IgG1, IgG2, IgG3 and IgG4, and CDC may be mediated by IgG1 and IgG3.

Antibodies that are substantially identical to the antibody comprising the VH of SEQ ID NO: 4 and the VL of SEQ ID NO: 5 may be used in the methods of the invention. The term "substantially identical" as used herein means that the two antibody VH or VL amino acid sequences being compared are identical or have "insubstantial differences". Insubstantial differences are substitutions of 1, 2, 3, 4, 5, 6, 7, 8, 9, 10, 11, 12, 13, 14, or 15 amino acids in an antibody heavy chain or light chain that do not adversely affect antibody properties. Percent identity may be determined for example by pairwise alignment using the default settings of the AlignX module of Vector NTI v.9.0.0 (Invitrogen, Carlsbad, Calif.). The protein sequences of the present invention may be used as a query sequence to perform a search against public or patent databases to, for example, identify related sequences. Exemplary programs used to perform such searches are the XBLAST or BLASTP programs, or the GenomeQuest™ (GenomeQuest, Westborough, Mass.) suite using the default settings. Exemplary substitutions that may be made to the antibodies that specifically bind CD38 are for example conservative substitutions with an amino acid having similar charge, hydrophobic, or stereochemical characteristics. Conservative substitutions may also be made to improve antibody properties, for example stability or affinity, or to improve antibody effector functions. 1, 2, 3, 4, 5, 6, 7, 8, 9, 10, 11, 12, 13, 14, or 15 amino acid substitutions may be made for example to the heavy or the light chain of the anti-CD38 antibody. Furthermore, any native residue in the VH or the VL may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions may be determined by those skilled in the art at the time such substitutions are desired. Amino acid substitutions may be done for example by PCR mutagenesis (U.S. Pat. No. 4,683,195). Libraries of variants may be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties. The generated variants may be tested for their binding to CD38, their ability to induce ADCC, ADCP or apoptosis, or modulate CD38 enzymatic activity in vitro using methods described herein.

In some embodiments, the antibody that specifically binds CD38 may bind human CD38 with a range of affinities ($K_D$). In one embodiment according to the invention, and in some embodiments of each and every one of the numbered embodiments listed below, the antibody that specifically binds CD38 binds to CD38 with high affinity, for example, with a $K_D$ equal to or less than about $10^{-7}$ M, such as but not limited to, 1-9.9 (or any range or value therein, such as 1, 2, 3, 4, 5, 6, 7, 8, or 9)$\times 10^{-8}$ M, $10^{-9}$ M, $10^{-10}$ M, $10^{-11}$ M, $10^{-12}$ M, $10^{-13}$ M, $10^{-14}$ M, $10^{-15}$ M or any range or value therein, as determined by surface plasmon resonance or the Kinexa method, as practiced by those of skill in the art. One exemplary affinity is equal to or less than $1 \times 10^{-8}$ M. Another exemplary affinity is equal to or less than $1 \times 10^{-9}$ M.

In some embodiments, the antibody that specifically binds CD38 is a bispecific antibody. The VL and/or the VH regions of the existing anti-CD38 antibodies or the VL and VH regions identified de novo as described herein may be engineered into bispecific full length antibodies. Such bispecific antibodies may be made by modulating the CH3 interactions between the monospecific antibody heavy chains to form bispecific antibodies using technologies such as those described in U.S. Pat. No. 7,695,936; Intl. Pat. Publ. No. WO04/111233; U.S. Pat. Publ. No. US2010/0015133; U.S. Pat. Publ. No. US2007/0287170; Intl. Pat. Publ. No. WO2008/119353; U.S. Pat. Publ. No. US2009/0182127; U.S. Pat. Publ. No. US2010/0286374; U.S. Pat. Publ. No. US2011/0123532; Intl. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention may be incorporated are for example Dual Variable Domain Immunoglobulins (Intl. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441).

For example, bispecific antibodies may be generated in vitro in a cell-free environment by introducing asymmetrical mutations in the CH3 regions of two monospecific homodimeric antibodies and forming the bispecific heterodimeric antibody from two parental monospecific homodimeric antibodies in reducing conditions to allow disulfide bond isomerization according to methods described in Intl. Pat. Publ. No. WO2011/131746. In the methods, the first monospecific bivalent antibody (e.g., anti-CD38 antibody) and the second monospecific bivalent antibody are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L.

The methods of the invention may be used to treat an animal patient belonging to any classification. Examples of such animals include mammals such as humans, rodents, dogs, cats and farm animals.

Administration/Pharmaceutical Compositions

The antibodies that specifically bind CD38 may be provided in the methods of the invention in suitable pharmaceutical compositions comprising the antibody that specifically bind CD38 and a pharmaceutically acceptable carrier. The carrier may be diluent, adjuvant, excipient, or vehicle with which the antibodies that specifically bind CD38 are administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies that specifically bind CD38 in such pharmaceutical formulation may vary widely, i.e., from less than about 0.5%, usually to at least about 1% to as much as 15 or 20%, 25%, 30%, 35%, 40%, 45% or 50% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, see especially pp. 958-989.

The mode of administration of the antibodies that specifically bind CD38 in the methods of the invention may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art. The antibodies that specifically bind CD38 may be administered intratumorally, to a lymph node draining site for local delivery into the tumor using known methods.

The antibodies that specifically bind CD38 may be administered to a patient by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours.

The dose given to a patient is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered, but 9, 10, 11, 12, 13, 14, 15, 16, 17, 18, 19, 20 or more doses may be given.

The administration of the antibodies that specifically bind CD38 in the methods of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the antibodies that specifically bind CD38 in the methods of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The antibodies that specifically bind CD38 may be administered in the methods of the invention by maintenance therapy, such as, e.g. once a week for a period of 6 months or more.

For example, the antibodies that specifically bind CD38 in the methods of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The antibodies that specifically bind CD38 in the methods of the invention may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The antibodies that specifically bind CD38 in the methods of the invention may be lyophilized for storage and reconstituted in a suitable carrier prior to use. This technique has been shown to be effective with conventional protein preparations and well known lyophilization and reconstitution techniques can be employed.

The antibodies that specifically bind CD38 in the methods of the invention may be administered in combination with a second therapeutic agent.

In the methods of the invention, the antibodies that specifically bind CD38 may be administered together with any one or more of the chemotherapeutic drugs or other anti-cancer therapeutics known to those of skill in the art. Chemotherapeutic agents are chemical compounds useful in the treatment of cancer and include growth inhibitory agents or other cytotoxic agents and include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL® docetaxel (TAXOTERE®) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including NEXAVAR® (sorafenib), SUTENT® (sunitinib), VOTRIENT™ (pazopanib), PALLADIA™ (toceranib), ZACTIMA™ (vandetanib), RECENTIN® (cediranib), regorafenib (BAY 73-4506), axitinib (AG013736), lestaurtinib (CEP-701), TARCEVA® (erlotinib), IRESSA™ (gefitinib), Gilotrif® (afatinib), TYKERB® (lapatinib), neratinib, and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and FARESTON® (toremifene); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in *Medical Oncology* (Calabresi et aL, eds.), Chapter 10, McMillan Publishing, are also applicable to the methods of the present invention.

Exemplary agents that may be used in combination with the antibody that specifically binds CD38 in the methods of the invention include tyrosine kinase inhibitors and targeted anti-cancer therapies such as IRESSA™ (gefitinib) and Tarceva® (erlotinib) and other antagonists of HER2, HER3, HER4 or VEGF. Exemplary HER2 antagonists include CP-724-714, HERCEPTIN™ (trastuzumab), OMNITARG™ (pertuzumab), TAK-165, TYKERB® (lapatinib) (EGFR and HER2 inhibitor), and GW-282974. Exemplary HER3 antagonists include anti-Her3 antibodies (see e.g., U.S. Pat. Publ. No. 2004/0197332). Exemplary HER4 antagonists include anti-HER4 siRNAs (see e.g., Maatta et al., Mol Biol Cell 17: 67-79, 2006. An exemplary VEGF antagonist is (Avastin™ (Bevacizumab).

Exemplary agents that may be used in combination with the antibody that specifically binds CD38 in the methods of the invention include standard of care drugs for solid tumors, or an immune checkpoint inhibitor.

The second therapeutic agent in the methods of the invention may be an immune checkpoint inhibitor.

In some embodiments, the immune checkpoint inhibitor is an anti-PD-1 antibody, an anti-PD-L1 antibody, an anti-PD-L2 antibody, an anti-LAG3 antibody, an anti-TIM3 antibody, or an anti-CTLA-4 antibody.

In some embodiments, the immune checkpoint inhibitor is an antagonistic anti-PD-1 antibody, an antagonistic anti-PD-L1 antibody, an antagonistic anti-PD-L2 antibody, an antagonistic anti-LAG3 antibody, or an antagonistic anti-TIM3 antibody.

In some embodiments, the immune checkpoint inhibitor is an anti-PD-1 antibody.

In some embodiments, the immune checkpoint inhibitor is an anti-PD-L1 antibody.

In some embodiments, the immune checkpoint inhibitor is an anti-PD-L2 antibody.

In some embodiments, the immune checkpoint inhibitor is an anti-LAG3 antibody.

In some embodiments, the immune checkpoint inhibitor is an anti-TIM3 antibody.

In some embodiments, the immune checkpoint inhibitor is an anti-CTLA-4 antibody.

Any antagonistic anti-PD-1 antibodies may be used in the methods of the invention. Exemplary anti-PD-1 antibodies that may be used are OPVIDO® (nivolumab) and KEYTRUDA® (pembrolizumab). OPVIDO® (nivolumab) is described in for example U.S. Pat. No. 8,008,449 (antibody 5C4) and comprises the VH of SEQ ID NO: 24 and the VL of SEQ ID NO: 25. KEYTRUDA® (pembrolizumab) is described in for example U.S. Pat. No. 8,354,509 and comprises the VH of SEQ ID NO: 22 and the VL of SEQ ID NO: 23. The amino acid sequences of nivolumab and pembrolizumab are also available through the CAS registry. Additional PD-1 antibodies that may be used are described in U.S. Pat. No. 7,332,582, U.S. Pat. Publ. No. 2014/0044738, Int. Pat. Publ. No. WO2014/17966 and U.S. Pat. Publ. No. 2014/0356363.

"Antagonist" refers to a molecule that, when bound to a cellular protein, suppresses at least one reaction or activity that is induced by a natural ligand of the protein. A molecule is an antagonist when the at least one reaction or activity is suppressed by at least about 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist. Antagonist may be an antibody, a soluble ligand, a small molecule, a DNA or RNA such as siRNA. A typical reaction or activity that is induced for example by PD-1 binding to its receptor PD-L1 or PD-L2 may be reduced antigen-specific $CD4^+$ or $CD8^+$ cell proliferation or reduced interferon-γ (IFN-γ) production by T cells, resulting in suppression of immune responses against for example tumor. A typical reaction or activity that is induced by TIM-3 binding to its receptor, such as galectin-9, may be reduced antigen specific $CD4^+$ or $CD8^+$ cell proliferation, reduced IFN-γ production by T cells, or reduced CD137 surface expression on $CD4^+$ or $CD8^+$ cells, resulting in suppression of immune responses against for example tumor. Hence, an antagonistic PD-1 antibody specifically binding PD-1, an antagonistic PD-L2, an antagonistic antibody specifically binding TIM-3 induces immune responses by inhibiting the inhibitory pathways.

```
                                          SEQ ID NO: 22
QVQLVQSGVEVKKPGASVKVSCKASGYTFTNYYMYWVRQAPGQGLEWMGG
INPSNGGTNFNEKFKNRVTLTTDSSTTTAYMELKSLQFDDTAVYYCARRD
YRFDMGFDYWGQGTTVTVSS

SEQ ID NO: 23
EIVLTQSPATLSLSPGERATLSCRASKGVSTSGYSYLHWYQQKPGQAPRL
LIYLASYLESGVPARFSGSGSGTDFTLTISSLEPEDFAVYYCQHSRDLPL
TFGGGTKVEIK

SEQ ID NO: 24
QVQLVESGGGVVQPGRSLRLDCKASGITFSNSGMHWVRQAPGKGLEWVAV
IWYDGSKRYYADSVKGRFTISRDNSKNTLFLQMNSLRAEDTAVYYCATND
DYWGQGTLVTVSS

SEQ ID NO: 25
EIVLTQSPATLSLSPGERATLSCRASQSVSSYLAWYQQKPGQAPRLLIYD
ASNRATGIPARFSGSGSGTDFTLTISSLEPEDFAVYYCQQSSNWPRTFGQ
GTKVEIK
```

Anti-PD-L1 antibodies that enhance immune response may be used in the methods of the invention (e.g. antagonistic anti-PD-L1 antibodies). Exemplary anti-PD-L1 antibodies that may be used are durvalumab, atezolizumab and avelumab, and those described in, for example, U.S. Pat. Publ. No. 2009/0055944, U.S. Pat. Nos. 8,552,154, 8,217,149 and 8,779,108.

Durvalumab comprises the VH of SEQ ID NO: 26 and the VL of SEQ ID NO: 27.

Atezolizumab comprises the VH of SEQ ID NO: 28 and the VL of SEQ ID NO: 29.

Avelumab comprises the VH of SEQ ID NO: 30 and the VL of SEQ ID NO: 31.

```
                                          SEQ ID NO: 26
EVQLVESGGGLVQPGGSLRLSCAASGFTFSRYWMSWVRQAPGKGLEWVAN
IKQDGSEKYYVDSVKGRFTISRDNAKNSLYLQMNSLRAEDTAVYYCAREG
GWFGELAFDYWGQGTLVTVSS

SEQ ID NO: 27
EIVLTQSPGTLSLSPGERATLSCRASQRVSSSYLAWYQQKPGQAPRLLIY
DASSRATGIPDRFSGSGSGTDFTLTISRLEPEDFAVYYCQQYGSLPWTFG
QGTKVEIK

SEQ ID NO: 28
EVQLVESGGGLVQPGGSLRLSCAASGFTFSDSWIHWVRQAPGKGLEWVAW
ISPYGGSTYYADSVKGRFTISADTSKNTAYLQMNSLRAEDTAVYYCARRH
WPGGFDYWGQGTLVTVSS

SEQ ID NO: 29
DIQMTQSPSSLSASVGDRVTITCRASQDVSTAVAWYQQKPGKAPKLLIYS
ASFLYSGVPSRFSGSGSGTDFTLTISSLQPEDFATYYCQQYLYHPATFGQ
GTKVEIK

SEQ ID NO: 30
EVQLLESGGGLVQPGGSLRLSCAASGFTFSSYIMMWVRQAPGKGLEWVSS
IYPSGGITFYADTVKGRFTISRDNSKNTLYLQMNSLRAEDTAVYYCARIK
LGTVTTVDYWGQGTLVTVSS

SEQ ID NO: 31
QSALTQPASVSGSPGQSITISCTGTSSDVGGYNYVSWYQQHPGKAPKLMI
YDVSNRPSGVSNRFSGSKSGNTASLTISGLQAEDEADYYCSSYTSSSTRV
FGTGTKVTVL
```

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-PD-1 antibody comprising the VH of SEQ ID NO: 24 and the VL of SEQ ID NO: 25 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-PD-1 antibody comprising the VH of SEQ ID NO: 22 and the VL of SEQ ID NO: 23 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-PD-L1 antibody comprising the VH of SEQ ID NO: 26 and the VL of SEQ ID NO: 27 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-PD-L1 antibody comprising the VH of SEQ ID NO: 28 and the VL of SEQ ID NO: 29 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-PD-L1 antibody comprising the VH of SEQ ID NO: 30 and the VL of SEQ ID NO: 31 for a time sufficient to treat the solid tumor.

The invention also provides for a method of enhancing an immune response in a patient, comprising administering to the patient in need thereof a therapeutically effective amount of an antibody that specifically binds CD38 comprising the VH of SEQ ID NO: 4 and the VL of SEQ ID NO: 5 in combination with an anti-PD-1 antibody comprising the VH of SEQ ID NO: 24 and the VL of SEQ ID NO: 25 for a time sufficient to enhance the immune response.

The invention also provides for a method of enhancing an immune response in a patient, comprising administering to the patient in need thereof a therapeutically effective amount of an antibody that specifically binds CD38 comprising the VH of SEQ ID NO: 4 and the VL of SEQ ID NO: 5 in combination with an anti-PD-1 antibody comprising the VH of SEQ ID NO: 22 and the VL of SEQ ID NO: 23 for a time sufficient to enhance the immune response.

The invention also provides for a method of enhancing an immune response in a patient, comprising administering to the patient in need thereof a therapeutically effective amount of an antibody that specifically binds CD38 comprising the VH of SEQ ID NO: 4 and the VL of SEQ ID NO: 5 in combination with an anti-PD-L1 antibody comprising the VH of SEQ ID NO: 26 and the VL of SEQ ID NO: 27 for a time sufficient to enhance the immune response.

The invention also provides for a method of enhancing an immune response in a patient, comprising administering to the patient in need thereof a therapeutically effective amount of an antibody that specifically binds CD38 comprising the VH of SEQ ID NO: 4 and the VL of SEQ ID NO: 5 in combination with an anti-PD-L1 antibody comprising the VH of SEQ ID NO: 28 and the VL of SEQ ID NO: 29 for a time sufficient to enhance the immune response.

The invention also provides for a method of enhancing an immune response in a patient, comprising administering to the patient in need thereof a therapeutically effective amount of an antibody that specifically binds CD38 comprising the VH of SEQ ID NO: 4 and the VL of SEQ ID NO: 5 in combination with an anti-PD-L1 antibody comprising the VH of SEQ ID NO: 30 and the VL of SEQ ID NO: 31 for a time sufficient to enhance the immune response.

The invention also provides for a method of treating a patient having a colorectal cancer, comprising administering to the patient in need thereof a therapeutically effective amount of an antibody that specifically binds CD38 in combination with an antagonistic anti-PD-1 antibody for a time sufficient to treat the colorectal cancer.

The invention also provides for a method of treating a patient having a colorectal cancer, comprising administering to the patient in need thereof a therapeutically effective amount of an antibody that specifically binds CD38 in combination with an antagonistic anti-PD-L1 antibody for a time sufficient to treat the colorectal cancer.

The invention also provides for a method of treating a patient having a colorectal cancer, comprising administering to the patient in need thereof a therapeutically effective amount of an antibody that specifically binds CD38 in combination with an antagonistic anti-PD-L2 antibody for a time sufficient to treat the colorectal cancer.

The invention also provides for a method of treating a patient having a lung cancer, comprising administering to the patient in need thereof a therapeutically effective amount of an antibody that specifically binds CD38 in combination with an antagonistic anti-PD-1 antibody for a time sufficient to treat the lung cancer.

The invention also provides for a method of treating a patient having a lung cancer, comprising administering to the patient in need thereof a therapeutically effective amount of an antibody that specifically binds CD38 in combination with an antagonistic anti-PD-L1 antibody for a time sufficient to treat the lung cancer.

The invention also provides for a method of treating a patient having a lung cancer, comprising administering to the patient in need thereof a therapeutically effective amount of an antibody that specifically binds CD38 in combination with an antagonistic anti-PD-L2 antibody for a time sufficient to treat the lung cancer.

The invention also provides for a method of treating a patient having a prostate cancer, comprising administering to the patient in need thereof a therapeutically effective amount of an antibody that specifically binds CD38 in combination with an antagonistic anti-PD-1 antibody for a time sufficient to treat the prostate cancer.

The invention also provides for a method of treating a patient having a prostate cancer, comprising administering to the patient in need thereof a therapeutically effective amount of an antibody that specifically binds CD38 in combination with an antagonistic anti-PD-L1 antibody for a time sufficient to treat the prostate cancer.

The invention also provides for a method of treating a patient having a prostate cancer, comprising administering to the patient in need thereof a therapeutically effective amount of an antibody that specifically binds CD38 in combination with an antagonistic anti-PD-L2 antibody for a time sufficient to treat the prostate cancer.

Anti-LAG-3 antibodies that enhance immune response may be used in the methods if the invention. Exemplary anti-LAG-3 antibodies that may be used are those described in, for example, Int. Pat. Publ. No. WO2010/019570.

Anti-CTLA-4 antibodies that enhance immune response may be used in the methods if the invention. An exemplary anti-CTLA-4 antibody that may be used is ipilimumab.

Anti-PD-1, anti-PD-L1, anti-PD-L2, anti-LAG3, anti-TIM3 and anti-CTLA-4 antibodies that may be used in the methods of the invention may also be generated de novo using methods described herein.

In some embodiments, anti-PD1 antibodies comprising the VH of SEQ ID NO: 32 and the VL of SEQ ID NO: 33 may be used.

In some embodiments, anti-PD1 antibodies comprising the VH of SEQ ID NO: 34 and the VL of SEQ ID NO: 35 may be used.

In some embodiments, anti-TIM-3 antibodies comprising the VH of SEQ ID NO: 36 and the VL of SEQ ID NO: 37 may be used.

In some embodiments, anti-TIM-3 antibodies comprising the VH of SEQ ID NO: 38 and the VL of SEQ ID NO: 39 may be used.

SEQ ID NO: 32
QVQLVQSGAEVKKPGSSVKVSCKASGGTFSSYAISWVRQAPGQGLEWMGG
IIPIFDTANYAQKFQGRVTITADESTSTAYMELSSLRSEDTAVYYCARPG
LAAAYDTGSLDYWGQGTLVTVSS

SEQ ID NO: 33
EIVLTQSPATLSLSPGERATLSCRASQSVRSYLAWYQQKPGQAPRLLIYD
ASNRATGIPARFSGSGSGTDFTLTISSLEPEDFAVYYCQQRNYWPLTFGQ
GTKVEIK

SEQ ID NO: 34
EVQLVESGGGLVQPGGSLRLSCAASGFAFSRYDMSWVRQAPGKGLESVAY
ISGGGANTYYLDNVKGRFTISRDNAKNSLYLQMNSLRAEDTAVYYCASPY
LSYFDVWGQGTLVTVSS

SEQ ID NO: 35
EIVMTQSPATLSVSPGERATLSCRASQSLSDYLHWYQQKPGQAPRLLIKS
ASQSISGIPARFSGSGSGTEFTLTISSLQSEDFAVYYCQNGHSFPYTFGQ
GTKLEIK

SEQ ID NO: 36
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKSP
YAPLDYWGQGTLVTVSS

SEQ ID NO: 37
EIVLTQSPATLSLSPGERATLSCRASQSVNDYLAWYQQKPGQAPRLLIYD
ASNRATGIPARFSGSGSGTDFTLTISSLEPEDFAVYYCQQGGHAPITFGQ
GTKVEIK

SEQ ID NO: 38
EVQLVQSGAEVKKPGESLKISCKGSGYSFTSYWMQWVRQMPGKGLEWMGA
IYPGDGDIRYTQNFKGQVTISADKSISTAYLQWSSLKASDTAMYYCARWE
KSTTVVQRNYFDYWGQGTTVTVSS

SEQ ID NO: 39
DIQMTQSPSSLSASVGDRVTITCKASENVGTFVSWYQQKPGKAPKLLIYG
ASNRYTGVPSRFSGSGSGTDFTLTISSLQPEDFATYYCGQSYSYPTFGQG
TKLEIK

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-PD-1 antibody comprising the VH of SEQ ID NO: 32 and the VL of SEQ ID NO: 33 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-PD-1 antibody comprising the VH of SEQ ID NO: 34 and the VL of SEQ ID NO: 35 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-TIM-3 antibody comprising the VH of SEQ ID NO: 36 and the VL of SEQ ID NO: 37 for a time sufficient to treat the solid tumor.

The invention also provides for a method of treating a patient having a solid tumor, comprising administering to the patient in need thereof a therapeutically effective amount of an antibody that specifically binds CD38 comprising the VH of SEQ ID NO: 4 and the VL of SEQ ID NO: 5 in combination with an anti-TIM-3 antibody comprising the VH of SEQ ID NO: 38 and the VL of SEQ ID NO: 39 for a time sufficient to treat the solid tumor.

In the methods of the invention, the combination of the antibody that specifically binds CD38 and the second therapeutic agent may be administered over any convenient timeframe. For example, the antibody that specifically binds CD38 and the second therapeutic agent may be administered to a patient on the same day, and even in the same intravenous infusion. However, the antibody that specifically binds CD38 and the second therapeutic agent may also be administered on alternating days or alternating weeks or months, and so on. In some methods, the antibody that specifically binds CD38 and the second therapeutic agent may be administered with sufficient proximity in time that they are simultaneously present (e.g., in the serum) at detectable levels in the patient being treated. In some methods, an entire course of treatment with the antibody that specifically binds CD38 consisting of a number of doses over a time period is followed or preceded by a course of treatment with the second therapeutic agent, consisting of a number of doses. A recovery period of 1, 2 or several days or weeks may be used between administration of the antibody that specifically binds CD38 and the second therapeutic agent.

The antibody that specifically binds CD38 or a combination of the antibody that specifically binds CD38 and the second therapeutic agent may be administered together with any form of radiation therapy including external beam radiation, intensity modulated radiation therapy (IMRT), focused radiation, and any form of radiosurgery including Gamma Knife, Cyberknife, Linac, and interstitial radiation (e.g. implanted radioactive seeds, GliaSite balloon), and/or with surgery.

Focused radiation methods that may be used include stereotactic radiosurgery, fractionated stereotactic radiosurgery, and intensity-modulated radiation therapy (IMRT). It is apparent that stereotactic radiosurgery involves the precise delivery of radiation to a tumorous tissue, for example, a brain tumor, while avoiding the surrounding non-tumorous, normal tissue. The dosage of radiation applied using stereotactic radiosurgery may vary, typically from 1 Gy to about 30 Gy, and may encompass intermediate ranges including, for example, from 1 to 5, 10, 15, 20, 25, up to 30 Gy in dose. Because of noninvasive fixation devices, stereotactic radiation need not be delivered in a single treatment. The treatment plan may be reliably duplicated day-to-day, thereby allowing multiple fractionated doses of radiation to be delivered. When used to treat a tumor over time, the radiosurgery is referred to as "fractionated stereotactic radiosurgery" or FSR. In contrast, stereotactic radiosurgery refers to a one-session treatment. Fractionated stereotactic radiosurgery may result in a high therapeutic ratio, i.e., a high rate of killing of tumor cells and a low effect on normal tissue. The tumor and the normal tissue respond differently to high single doses of radiation vs. multiple smaller doses of radiation. Single large doses of radiation may kill more normal tissue than several smaller doses of radiation may. Accordingly, multiple smaller doses of radiation can kill more tumor cells while sparing normal tissue. The dosage of radiation applied using fractionated stereotactic radiation may vary from range from 1 Gy to about 50 Gy, and may encompass intermediate ranges including, for example, from 1 to 5, 10, 15, 20, 25, 30, 40, up to 50 Gy in hypofractionated doses. Intensity-modulated radiation therapy (IMRT) may also be used. IMRT is an advanced mode of high-precision three-dimensional conformal radiation therapy (3DCRT), which uses computer-controlled linear accelerators to deliver precise radiation doses to a malignant tumor or specific areas within the tumor. In 3DCRT, the profile of each radiation beam is shaped to fit the profile of the target from a beam's eye view (BEV) using a multileaf collimator (MLC), thereby producing a number of beams. IMRT allows the radiation dose to conform more precisely to the three-dimensional (3-D) shape of the tumor by modulating the intensity of the radiation beam in multiple small volumes. Accordingly, IMRT allows higher radiation doses to be focused to regions within the tumor while minimizing the dose to surrounding normal critical structures. IMRT improves the ability to conform the treatment volume to concave tumor shapes, for example, when the tumor is wrapped around a vulnerable structure, such as the spinal cord or a major organ or blood vessel.

Subcutaneous Administration of Pharmaceutical Compositions Comprising an Antibody that Specifically Binds CD38 and a Hyaluronidase The antibody that specifically binds CD38 may be administered as a pharmaceutical composition comprising the antibody that specifically binds CD38 and a hyaluronidase subcutaneously.

The concentration of the antibody that specifically binds CD38 in the pharmaceutical composition administered subcutaneously may be about 20 mg/ml.

The pharmaceutical composition administered subcutaneously may comprise between about 1,200 mg-1,800 mg of the antibody that specifically binds CD38.

The pharmaceutical composition administered subcutaneously may comprise about 1,200 mg of the antibody that specifically binds CD38.

The pharmaceutical composition administered subcutaneously may comprise about 1,600 mg of the antibody that specifically binds CD38.

The pharmaceutical composition administered subcutaneously may comprise about 1,800 mg of the antibody that specifically binds CD38.

The pharmaceutical composition administered subcutaneously may comprise between about 30,000 U-45,000 U of the hyaluronidase.

The pharmaceutical composition administered subcutaneously may comprise about 1,200 mg of the antibody that specifically binds CD38 and about 30,000 U of the hyaluronidase.

The pharmaceutical composition administered subcutaneously may comprise about 1,800 mg of the antibody that specifically binds CD38 and about 45,000 U of the hyaluronidase.

The pharmaceutical composition administered subcutaneously may comprise about 1,600 mg of the antibody that specifically binds CD38 and about 30,000 U of the hyaluronidase.

The pharmaceutical composition administered subcutaneously may comprise about 1,600 mg of the antibody that specifically binds CD38 and about 45,000 U of the hyaluronidase.

The pharmaceutical composition administered subcutaneously may comprise the hyaluronidase rHuPH20 having the amino acid sequence of SEQ ID NO: 40.

rHuPH20 is a recombinant hyaluronidase (HYLENEX® recombinant) and is described in Int. Pat. Publ. No. WO2004/078140.

Hyaluronidase is an enzyme that degrades hyaluronic acid (EC 3.2.1.35) and lowers the viscosity of hyaluronan in the extracellular matrix, thereby increasing tissue permeability.

```
                                              SEQ ID NO: 40
MGVLKFKHIFFRSFVKSSGVSQIVFTFLLIPCCLTLNFRAPPVIPNVPFL

WAWNAPSEFCLGKFDEPLDMSLFSFIGSPRINATGQGVTIFYVDRLGYYP

YIDSITGVTVNGGIPQKISLQDHLDKAKKDITFYMPVDNLGMAVIDWEEW

RPTWARNWKPKDVYKNRSIELVQQQNVQLSLTEATEKAKQEFEKAGKDFL

VETIKLGKLLRPNHLWGYYLFPDCYNHHYKKPGYNGSCFNVEIKRNDDLS

WLWNESTALYPSIYLNTQQSPVAATLYVRNRVREAIRVSKIPDAKSPLPV

FAYTRIVFTDQVLKFLSQDELVYTFGETVALGASGIVIWGTLSIMRSMKS

CLLLDNYMETILNPYIINVTLAAKMCSQVLCQEQGVCIRKNWNSSDYLHL

NPDNFAIQLEKGGKFTVRGKPTLEDLEQFSEKFYCSCYSTLSCKEKADVK

DTDAVDVCIADGVCIDAFLKPPMETEEPQIFYNASPSTLSATMFIVSILF

LIISSVASL
```

The administration of the pharmaceutical composition comprising the antibody that specifically binds CD38 and the hyaluronidase may be repeated after one day, two days, three days, four days, five days, six days, one week, two weeks, three weeks, four weeks, five weeks, six weeks, seven weeks, two months, three months, four months, five months, six months or longer. Repeated courses of treatment are also possible, as is chronic administration. The repeated administration may be at the same dose or at a different dose. For example, the pharmaceutical composition comprising the antibody that specifically binds CD38 and the hyaluronidase may be administered once weekly for eight weeks, followed by once in two weeks for 16 weeks, followed by once in four weeks. The pharmaceutical compositions to be administered may comprise about 1,200 mg of the antibody that specifically binds CD38 and about 30,000 U of hyaluronidase, wherein the concentration of the antibody that specifically binds CD38 in the pharmaceutical composition is about 20 mg/ml. The pharmaceutical compositions to be administered may comprise about 1,800 mg of the antibody that specifically binds CD38 and about 45,000 U of hyaluronidase. The pharmaceutical compositions to be administered may comprise about 1,600 mg of the antibody that specifically binds CD38 and about 30,000 U of hyaluronidase. The pharmaceutical compositions to be administered may comprise about 1,600 mg of the antibody that specifically binds CD38 and about 45,000 U of hyaluronidase.

The pharmaceutical composition comprising the antibody that specifically binds CD38 and the hyaluronidase may be administered subcutaneously to the abdominal region.

The pharmaceutical composition comprising the antibody that specifically binds CD38 and the hyaluronidase may be administered in a total volume of about 80 ml, 90 ml, 100 ml, 110 ml or 120 ml.

For administration, 20 mg/ml of the antibody that specifically binds CD38 in 25 mM sodium acetate, 60 mM sodium chloride, 140 mM D-mannitol, 0.04% polysorbate 20, pH 5.5 may be mixed with rHuPH20, 1.0 mg/mL (75-150 kU/mL) in 10 mM L-Histidine, 130 mM NaCl, 10 mM L-Methionine, 0.02% Polysorbate 80, pH 6.5 prior to administration of the mixture to a subject.

While having described the invention in general terms, the embodiments of the invention will be further disclosed in the following examples that should not be construed as limiting the scope of the claims.

Example 1. General Materials and Methods

Sample Collection and Processing

Peripheral blood and bone marrow aspirates were collected in heparinized tubes at baseline immediately prior to the first infusion and at specified time points during treatment. The majority of samples were evaluated using real-time flow cytometry, as they arrived at a central laboratory, 24-48 hours after collection. Peripheral blood mononuclear cells (PBMCs) were obtained from whole blood, isolated by density-gradient centrifugation, and stored frozen until analysis. For the T-cell activation, clonality, and $CD38^+$ Treg suppression assays, pre- and post-treatment samples were analyzed at the same time, using frozen PBMC samples.

Flow cytometric analysis of these samples was performed at BARC global central laboratory for evaluation of NK, T, B, myeloma cells ($CD138^+$) and CD38 expression using a pre-validated immunophenotyping assay. Briefly, blood samples and bone marrow samples were stained with the following multifluorochrome antibody panels: cell lineage panel: PerCPCy5.5α-CD19 (cloneHIB19; Becton Dickinson [BD]), APCα-CD24 (SN3; eBioscience), PC7α-CD3 (UCHT-1; Beckman Coulter), V500α-CD16 (3G8; BD), and PEα-CD56 (MY; BD); regulatory T cell ($T_{reg}$) panel: APCα-CD25 (2A3; BD), PEα-CD127 (HIL-7R-M21; BD), APC-H7α-HLA-DR (G46-6; BD), and PerCPα-CD4 (L200; BD); naive/memory T-cell panel: APC-H7α-CD4 (RPA-T4; BD), PerCP-Cy5.5α-CD8 (RPA-T4 BD), PEα-CD62L (SKI 1; BD), and APCα-CD45RA (HI100; BD). CD38 expression was evaluated using Alexa 647 labeled antibody mAb 003 described in U.S. Pat. No. 7,829,693 having the VH and the VL sequences of SEQ ID NO: 14 and SEQ ID NO: 15. The blood samples were prepared using different Lyse-wash methods. For bone marrow aspirate samples either membrane or intracellular staining was performed with various antibodies. Becton Dickinson FACSLysing solution was used for lysing red blood cells in peripheral blood samples and Fix and Perm cell permeabilization reagents from Invitrogen were used for intracellular staining of bone marrow aspirate samples. Stained samples were acquired on FACS Canto II flow cytometers and data was analyzed using FacsDiva software. Absolute counts of immune cell populations in the blood samples and as percent of lymphocytes in bone marrow samples were determined at all the time points tested.

T-Cell Receptor (TCR) Sequencing

T-cell diversity was analyzed by deep sequencing of TCR rearrangements to assess $CD8^+$ T-cell clonality using genomic DNA from PBMC samples. TCR sequencing was performed using Adaptive Biotechnologies commercial Immunoseq™ assay, and analysis was performed using prequalified multiplex polymerase chain reaction (PCR) assays (TR2015CRO-V-019), which were composed of forward and reverse primers that directly targeted the family of variable (V) genes (forward primers) and joining (J) genes (reverse primers). Each V and J gene primer acted as priming pairs to amplify somatically recombined TCRs, and each primer contained a specific universal DNA sequence. Following the initial PCR amplification, each amplicon was amplified a second time with forward and reverse primers containing the universal sequence and adaptor sequence needed for DNA sequencing by Illumina.

T-Cell Responses to Viral- and Alloantigens

Patient PBMCs were seeded on 96 well plates ($2\times10^5$ cells/well) and stimulated for 5 days with a cocktail of 23 major histocompatibility complex (MHC) class I-restricted viral peptides from human cytomegalovirus (CMV), Epstein-Barr virus (EBV), and influenza virus (2 μg/ml; CEF peptide pool; PANATecs®) or an equivalent number of 25-Gy irradiated allogeneic PBMCs from healthy donors. Unstimulated PBMCs and PBMCs stimulated with anti-CD3/CD28-coated beads served as negative and positive controls, respectively. On day 5, interferon γ (IFN-γ) from cell-free supernatant was measured by sandwich enzyme-linked immunosorbent assay (ELISA; Human IFN gamma ELISA Ready-SET-Go; eBioscience) and served as a surrogate marker for T-cell activation.

Regulatory T-Cell (Treg) Suppression of Effector Cell Functions: Carboxyfluorescein Succinimidyl (CFSE) Dilution Assay PBMCs from healthy donors were labelled with PerCP-Cy5.5α-CD3 (SK7; BD), KOα-CD45, (J33; Beckman Coulter), V450α-CD4 (SK3; BD), PEα-CD25 (M-A251, BD), PE Cy7α-CD127 (HIL-7R-M21; BD), and APCα-CD38 (HB-7; BD) and sorted by FACS Aria (BD). Sorted effector cells were labelled with carboxyfluorescein succinimidyl ester (CFSE; eBioscience) and stimulated with anti-CD3/CD28-coated beads in the presence or absence of $CD38^+$ Tregs or $CD38^-$ Tregs (1:1 Treg to effector cell ratio) in RPMI plus 10% fetal calf serum. After 72 hours, flow cytometry was performed and the percent dilution of CFSE was used as a surrogate for T-cell proliferation.

Myeloid Derived Suppressor Cell (MDSC) Phenotyping and DARZALEX™ (Daratumumab)-Mediated ADCC PBMC from three normal healthy donors were co-cultured with myeloma tumor cell lines (RPMI8226, U266, H929) for six days, and evaluated for the production of granulocytic MDSC (G-MDSC) ($CD11b^+CD14^-HLA^-DR^-CD15^+CD33^+$) as described in Gorgun et al., Blood 121: 2975-87, 2013. G-MDSC were not present in normal healthy PBMC, however following co-culture with all three myeloma cells lines G-MDSC were present as 5-25% of total PBMC population (data not shown). Gating strategy for flow cytometric evaluation of G-MDSC included $CD11b^+$ as the first gate, followed by $CD14^-$ and $HLA^-DR^-$ gating, and then followed by $CD15^+$ and $CD33^+$ gating. G-MDSCs were cell sorted and evaluated for CD38 expression levels and sensitivity to DARZALEX™ (daratumumab) mediated ADCC. To evaluate the effect of DARZALEX™ (daratumumab) on ADCC/CDC of MDSCs, serum containing complement or an isotype control was added to ADCC assays.

Naïve and Memory T-Cell Analysis

Heparinized peripheral-blood samples were obtained from patients prior to each infusion of DARZALEX™ (daratumumab). Peripheral-blood mononuclear cells (PBMCs) were isolated by Ficoll-Hypaque density-gradient centrifugation and stored in cryopreservation medium (RPMI supplemented with 10% human serum and 10% dimethyl sulfoxide) in liquid nitrogen. For FACS analysis, PBMCs were thawed and $2\times10^6$ cells/panel was resuspended in phosphate-buffered saline (PBS) with 0.05% azide and 0.1% HAS.

Data Analysis

All data analysis and generation of relevant graphs were performed exclusively using R software (R: A Language and Environment for Statistical Computing, R Development Core Team, R Foundation for Statistical Computing, Vienna, Austria, 2011, ISBN 3-900051-07-0. All treated subjects with an evaluable response were included in the data analysis. Consistently throughout, responders are defined as subjects with a Best Response per IRC of sCR, VGPR and PR, and non-responders are defined as subjects with a Best Response per IRC of MR, SD and PD.

Different statistical comparisons included (i) baseline levels between responders and non-responders, (ii) baseline versus on treatment for responders and for non-responders, (iii) percent changes between responders and non-responders, (iv) ratio changes of baseline versus on treatment. Each comparison included first a test for normality with a Shapiro-Wilk test (Royston (1995) Remark AS R94: A remark on Algorithm AS 181: The W test for normality. Applied Statistics, 44, 547-551). Almost exclusively, the data was found to not have a normal distribution. The differential level testing included conducting both a non-parametric Wilcox rank sum test (Hollander and Wolfe (1973), Non-parametric Statistical Methods. New York: John Wiley & Sons. Pages 27-33 (one-sample), 68-75 (two-sample), and a t-test following a Box Cox transformation (Weisberg, S. (2014) Applied Linear Regression, Fourth Edition, Wiley Wiley, Chapter 7). For the Box Cox transformation, a small number (1e-07) was added to values equal to zero. In all cases, the two tests agreed. The Wilcox rank sum test p-values are shown in the tables throughout the specification unless otherwise indicated. When testing for differences of the baseline versus on treatment for responders and non-responders a two-group paired test per subject was ran, in all other cases a two group unpaired test was conducted.

As samples to analyze various lymphocyte populations were not taken at identical time points for the different dosing schedules, population modeling was conducted. Model fitting was done on the rank of the visits. Population modeling on total and activated NK cells involved fitting a broken stick model (Lutz et al., "Statistical model to estimate a threshold dose and its confidence limits for the analysis of sublinear dose-response relationships, exemplified for mutagenicity data." Mutation Research/Genetic Toxicology and Environmental Mutagenesis 678.2 (2009): 118-122.). Linear mixed effect models with random intercept and slope were fit on the B-cell, T-cell subpopulations, and leukocytes, monocytes, neutrophils and lymphocytes patient population data (Bates et al., (2014). "lme4: Linear mixed-effects models using Eigen and S4." ArXiv e-print; submitted to *Journal of Statistical Software*. This linear mixed modeling was done on the relative day since treatment start (ADY). The linear mixed model fitting were done on log transformed response variables. In case of response variable values equal to zero, 0.1 was added to all response variable values to allow for modeling on log scale.

Example 2. Study 54767414MMY2002 Design (SIRIUS)

The target population for Study 54767414MMY2002 (SIRIUS) is patients with advanced multiple myeloma who received at least 3 prior lines of therapy including a proteasome inhibitor (PI) and an immunomodulatory drug (IMiD) or double refractory to a PI and an IMiD. Response evaluations for the primary endpoint/final analysis were based on assessments from an independent review committee (IRC) and computerized algorithm, using 2011 IMWG Guidelines (Clinical Study Report: An Open-label, Multicenter, Phase 2 Trial Investigating the Efficacy and Safety of DARZALEX™ (daratumumab) in Subjects With Multiple Myeloma Who Have Received at Least 3 Prior Lines of Therapy (Including a Proteasome Inhibitor and IMiD) or are Double Refractory to a Proteasome Inhibitor and an IMiD (EDMS-ERI-92399922; de Weers et al., (2011) *J Immunol* 186(3): 1840-1848).

These assessments included: overall response rate (ORR), duration of response, time to response and best response, clinical benefit rate, time to progression (TTP), progression free survival (PFS), and overall survival (OS).

A total of 124 subjects were treated with DARZALEX™ (daratumumab) in this study (de Weers et al., (2011) *J Immunol* 186(3):1840-1848). 18 subjects were treated with 8 mg/kg and 106 subjects were treated with 16 mg/kg. The dosing schedule was as follows:

Group A: DARZALEX™ (daratumumab) 16 mg/kg: Cycles 1 and 2: Days 1, 8, 15, and 22 (weekly), Cycle 3 to 6: Days 1 and 15 (every other week), Cycles $7^+$: Day 1 (every 4 weeks). Each cycle was 4 weeks.

Group B: DARZALEX™ (daratumumab) 8 mg/kg: Cycle $1^+$: Day 1 (every 4 weeks).

The primary objective of the study was to determine the efficacy of 2 treatment regimens of DARZALEX™ (daratumumab), as measured by the ORR (CR+PR), in subjects with multiple myeloma who have received at least 3 prior lines of therapy including a PI and an IMiD or whose disease is double refractory to both a PI and an IMiD (Clinical Study Report: An Open-label, Multicenter, Phase 2 Trial Investigating the Efficacy and Safety of DARZALEX™ (daratumumab) in Subjects With Multiple Myeloma Who Have Received at Least 3 Prior Lines of Therapy (Including a Proteasome Inhibitor and IMiD) or are Double Refractory to a Proteasome Inhibitor and an IMiD. EDMS-ERI-92399922).

The secondary objectives of this study included evaluation of the safety and tolerability of DARZALEX™ (daratumumab), demonstration of additional measures of efficacy (e.g, clinical benefit, TTP, PFS, and OS) along with assessment of pharmacokinetics, immunogenicity, pharmacodynamics, and to explore biomarkers predictive of response to DARZALEX™ (daratumumab). Additional study related information is available from the clinical study protocol (Clinical Study Report: An Open-label, Multicenter, Phase 2 Trial Investigating the Efficacy and Safety of DARZALEX™ (daratumumab) in Subjects With Multiple Myeloma Who Have Received at Least 3 Prior Lines of Therapy (Including a Proteasome Inhibitor and IMiD) or are Double Refractory to a Proteasome Inhibitor and an IMiD. EDMS-ERI-92399922).

In Stage 1 of Part 1, 1 subject (6%) responded in the 8 mg/kg group, and 5 subjects (31%) responded in the 16 mg/kg group. Therefore, only the 16 mg/kg group was expanded in Stage 2 of Part 1 and in Part 2.

In the 16 mg/kg group, 31 subjects achieved response of PR or better based on IRC assessment; the ORR was 29% (95% CI: 21%, 39%). Three subjects (3%) achieved sCR, and 13 subjects (12%) achieved VGPR or better.

Example 3. Effect of DARZALEX™ (Daratumumab) on T-Cell Expansion and Activity in Patients Enrolled in the 54767414MMY2002 Study (SIRIUS)

CD38 is expressed on a variety of immune and hematopoietic cells. Broad immune profiling by flow cytometry was performed to examine the effect of DARZALEX™ (daratumumab) on immune cell subsets and the association of baseline levels of these cells to clinical response. Various cell populations, including T-cells ($CD3^+$, $CD4^+$, $CD8^+$ and regulatory T-cells (Treg)), B-cells ($CD19^+$), NK cells, monocytes ($CD\ 14^k$), leukocytes, and neutrophils were evaluated by flow cytometry in peripheral blood and bone marrow aspirates at baseline and following DARZALEX™ (daratumumab) treatment to monitor for changes in these cellular populations in responders and non-responders.

Lymphocytes, Leukocytes, Monocytes and Neutrophils

Leukocyte, lymphocyte, monocyte, and neutrophil counts were studied in peripheral blood in responders and non-responders. Total lymphocytes were found increased with DARZALEX™ (daratumumab) treatment in responders with both 8 mg/kg and 16 mg/kg dose (FIG. 1). Linear mixed effect modeling revealed an increase of $0.8 \times 10^6$ cells/μL on log scale per 100 days (CI=0.06, 0.11). Slight increases were found for monocytes and leukocytes with significant increase of $0.03 \times 10^6$ cells/μL (CI=0.01, 0.04) and $0.03 \times 10^6$ cells/μL on log scale (CI=0.01, 0.05) for each 100 days respectively. Median neutrophil counts were consistent with baseline and did not vary significantly, although there was neutropenia noted for some patients.

Baseline levels of each of these cellular populations were compared between response groups. No evidence was found for baseline levels to be different for any of these cell types across response groups using Wilcoxon signed-rank test (Table 1).

TABLE 1

Peripheral blood cell counts in responders vs non-responders at baseline

| | N | Median | Mean (SD) | Range | P-value* |
|---|---|---|---|---|---|
| Leukocytes: R | 33 | 4.3 | 4.32 (1.65) | (1.6; 8.8) | |
| Leukocytes: NR | 82 | 4.19 | 4.77 (2.26) | (2.13; 13.8) | 0.60987 |
| Lymphocytes: R | 33 | 0.9 | 1.09 (0.59) | (0.27; 2.67) | |
| Lymphocytes: NR | 82 | 1 | 1.05 (0.55) | (0.3; 2.8) | 0.85028 |
| Monocytes: R | 33 | 0.43 | 0.5 (0.25) | (0.2; 0.97) | |
| Monocytes: NR | 82 | 0.5 | 0.51 (0.25) | (0.04; 1.3) | 0.72803 |
| Neutrophils: R | 33 | 2.47 | 2.54 (1.23) | (1.06; 5.94) | |
| Neutrophils: NR | 82 | 2.44 | 3.05 (2.08) | (1; 11.7) | 0.40373 |

N: number of samples per group
R: responder
NR: non-responder
*non-responder vs responder
SD: standard deviation NK Cells Total NK cells (CD $16^+$CD$56^+$) and activated NK cells (CD$16^+$CD$56^{dim}$) were reduced with DARZALEX™ (daratumumab) treatment over time (data not shown).

B-Cells

Absolute counts of B-cells (CD$45^+$CD$3^-$CD$19^+$) were measured in peripheral blood or bone marrow aspirates during DARZALEX™ (daratumumab) treatment over time in responders and non-responders. B-cells slightly increased in the whole blood and were maintained in the bone marrow aspirates. Linear mixed modeling of B-cells in peripheral blood revealed a minimal increase of $0.1 \times 10^6$ cells/μl [CI=0.04, 0.16 for each 100 days on log scale over the course of DARZALEX™ (daratumumab) treatment. There were no changes to the percentages of B-cells (CD$45^+$CD$3^-$CD$19^+$/Lymphocytes) in the bone marrow aspirates during daratumumab treatment, in either responders or non-responders (p=0.1 and 0.4, respectively). Further, no evidence was found for B-cell counts to be different at baseline between responders and non-responders (p=0.5).

T-Cells

Lymphocytes were noted to increase with DARZALEX™ (daratumumab) treatment (FIG. 1) even though B cells showed only a minimal increase (see above). To investigate further, various T-cell populations were studied (CD$3^+$, CD$4^+$, CD$8^+$ T cells, regulatory T cells) in both peripheral blood and bone marrow.

Figure 2:
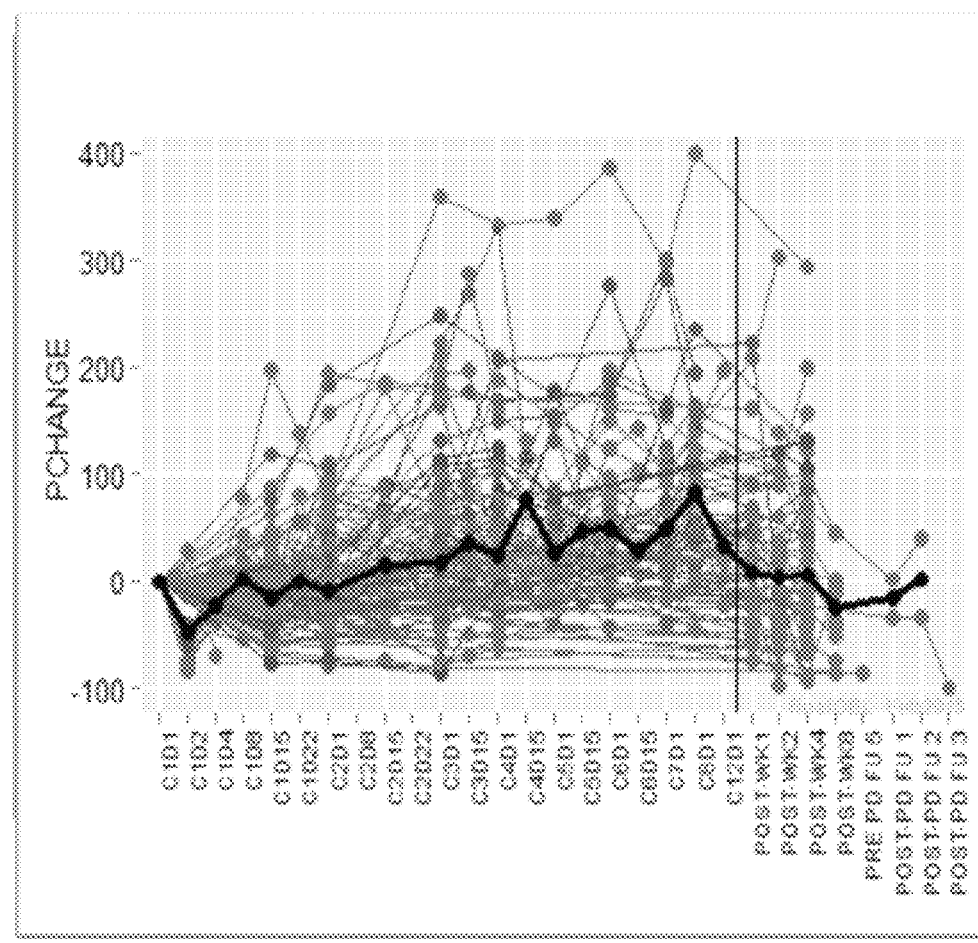
FIG. 2 shows the percent (%) change of absolute counts of $CD3^+$ T cells to baseline in peripheral blood in patients treated with DARZALEX™ (daratumumab) for each individual patient (light gray lines). Study: SIRIUS (MMY2002). The X-axis indicates time expressed as treatment cycle and days of dosing within each treatment cycle (C1D1: cycle 1, day 1; C1D4; cycle 1, day 4, etc). WK: week; POST-WK: post-treatment at indicated weeks; POST-PD FU: follow-up after progression. The black line shows the median % change for all patients.
Figure 3:
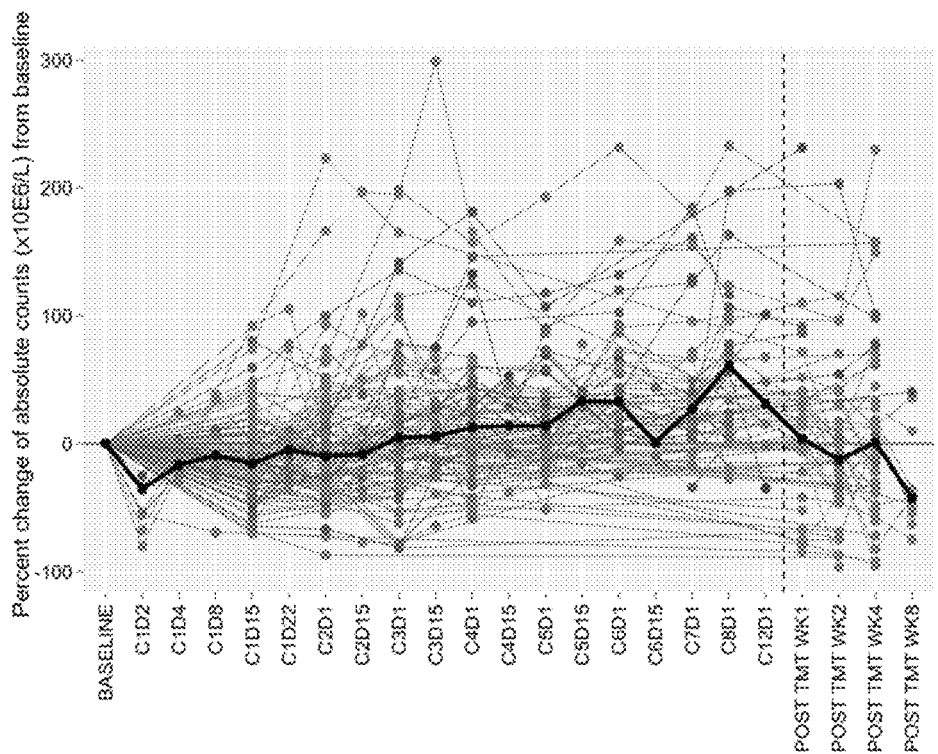
FIG. 3 shows the percent (%) change of absolute counts of $CD4^+$ T cells to baseline in peripheral blood in patients treated with DARZALEX™ (daratumumab) for each individual patient (light gray lines). Study: SIRIUS. The X-axis indicates time expressed as treatment cycle and days of dosing within each treatment cycle (C1D1: cycle 1, day 1; C1D4; cycle 1, day 4, etc). WK: week; POST-TMT: post-treatment. The black line shows the median % change for all patients.
Figure 4:
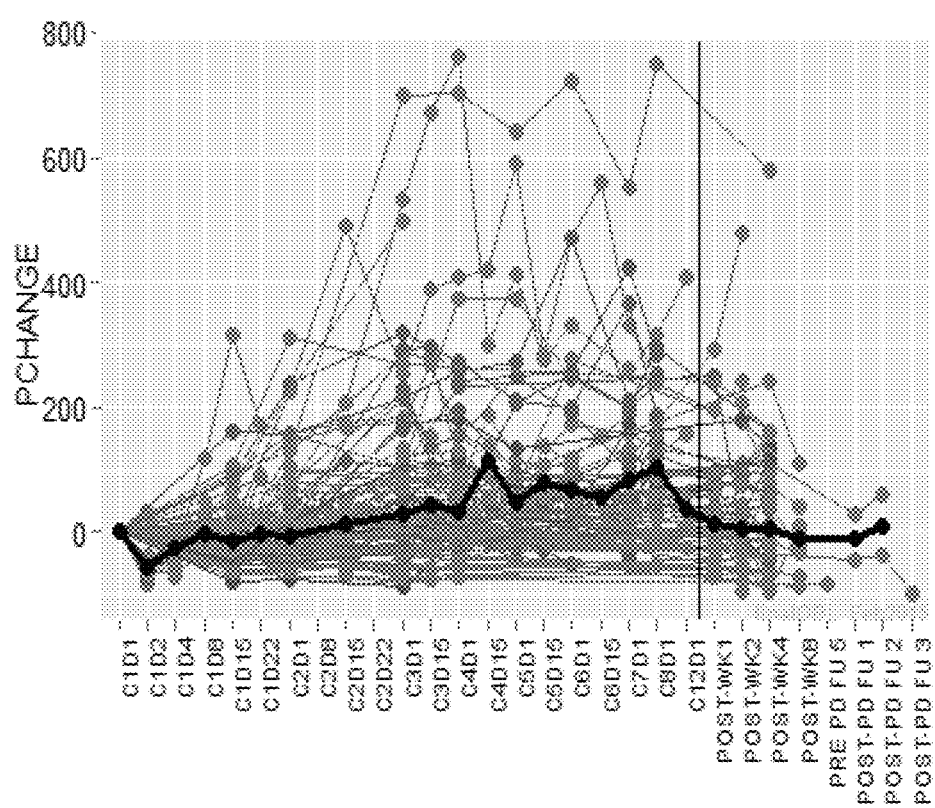
FIG. 4 shows the percent (%) change of absolute counts of $CD8^+$ T cells to baseline in peripheral blood in patients treated with DARZALEX™ (daratumumab) for each individual patient (light gray lines). Study: SIRIUS. The X-axis indicates time expressed as treatment cycle and days of dosing within each treatment cycle (C1D1: cycle 1, day 1; C1D4; cycle 1, day 4, etc). WK: week; Pre-PD FU: follow-up before progression; Post-PD FU: follow-up after progression. The black line shows the median % change for all patients.

CD$3^+$, CD$4^+$ and CD$8^+$ T-cells were increased in peripheral blood (both absolute counts/μl and percentage of lymphocytes) following DARZALEX™ (daratumumab) treatment. FIG. 2 shows the percent change of absolute counts of CD$3^+$ T-cells (CD$45^+$CD$3^+$) from baseline in peripheral blood over time for every patient. The black line in the Figure shows the median absolute counts$\times 10^6$ cells/μL for all patients. Only visits with more than 2 observations were included into the Figure. FIG. 3 shows the % change of absolute counts of CD$4^+$ T-cells (CD$45^+$CD$3^+$CD$4^+$) from baseline in peripheral blood over time for every patient. The black line in the Figure shows the median for all patients. Only visits with more than 2 observations were included into the Figure. FIG. 4 shows the % change of absolute counts of CD$8^+$ T-cells (CD$45^+$CD$3^+$CD$8^+$) from baseline in peripheral blood over time for every patient. The black line in the Figure shows the median for all patients. Only visits with more than 2 observations were included into the Figure. Linear mixed modeling on absolute counts in peripheral blood revealed on average total T-cell (CD$45^+$CD$3^+$) increase of $0.13 \times 10^6$ cells/μl on log scale for each 100 days (CI=0.1, 0.15) following DARZALEX™ (daratumumab) treatment. CD$8^+$ T-cells were found to significantly increase by $0.16 \times 10^6$ cells/μl on log scale for each 100 days (CI=0.13, 0.19). CD$4^+$ cells were found to have a moderate increase of $0.11 \times 10^6$ cells/μl on log scale for each 100 days (CI=0.09, 0.13).

For each of the T-cell subpopulations, responders showed a higher maximum percent change of absolute counts to baseline than non-responders (CD$3^+$ p=3.2993e-05; CD$4^+$ p=3.486e-05; CD$8^+$ p=2.7172e-05; regulatory T cell p=0.002). Table 2 shows the Wilcoxon signed-rank test results for the comparison of each T-cell subpopulation in peripheral blood between responders and non-responders for percent change of absolute counts to baseline.

TABLE 2

Percent change of absolute cell counts; peripheral blood

| Sample | N | Median | Mean (SD) | Range | P-value* |
|---|---|---|---|---|---|
| CD$45^+$CD$3^+$: R | 33 | 86.76 | 118.91 (104.07) | (−16.1; 398.71) | |
| CD$45^+$CD$3^+$: NR | 80 | 28.08 | 43.02 (69.55) | (−67.11; 286.67) | 3.30E−05 |
| CD$45^+$CD$3^+$CD$4^+$: R | 33 | 72.08 | 77.74 (60.99) | (−21.05; 233.21) | |
| CD$45^+$ CD$3^+$CD$4^+$: NR | 80 | 19.48 | 29.36 (59.58) | (−68; 298.89) | 3.49E−05 |
| CD$45^+$ CD$3^+$CD$8^+$: R | 33 | 106.6 | 180.81 (192.37) | (−7.07; 760.51) | |
| CD$45^+$ CD$3^+$CD$8^+$: NR | 80 | 32.24 | 63.96 (112.44) | (−66.22; 588.89) | 2.72E−05 |

N: number of samples per group
R: responder
NR: non-responder
*responder vs. non-responder
SD: standard deviation Similarly in bone marrow, total T-cells ($CD45^+CD3^+$ as a percentage of lymphocytes) and $CD8^+$ T-cells ($CD45^+CD3^+CD8^+$ as a percentage of lymphocytes) were found to significantly increase during DARZALEX™ (daratumumab) treatment, for both responders and non-responders ($CD3^+$ responders p=3.8147e-06, non-responders p=9.8225e-05; $CD8^+$ responders p=3.8147e-06, non-responders p=0.0003). There was no change in median $CD4^+$ T-cells in either clinical response group in bone marrow.

Figure 5:
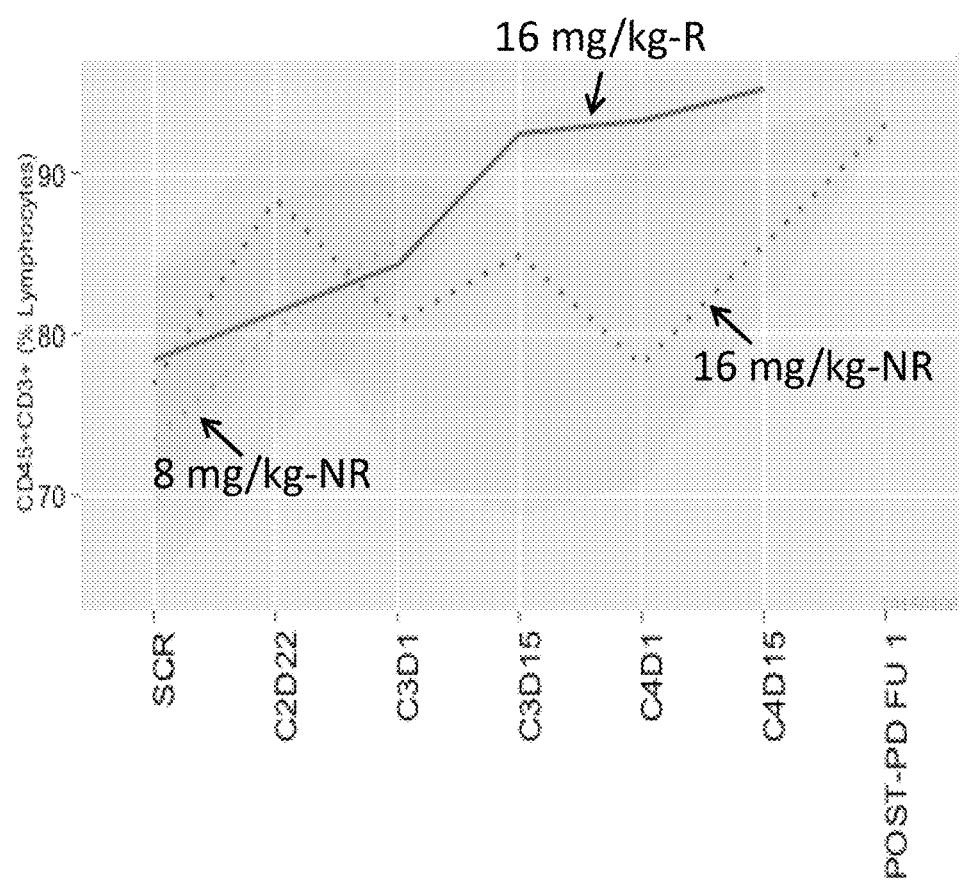
FIG. 5 shows that the number of $CD45^+CD3^+$ cells (measured as percentage of lymphocytes) in bone marrow aspirates was increased during DARZALEX™ (daratumumab) treatment over time at doses 8 mg/kg or 16 mg/kg. The graph includes both responders and non-responders as indicated. Study: SIRIUS. The X-axis indicates time expressed as treatment cycle and days of dosing within each treatment cycle (C2D22: cycle 2, day 22; etc). SCR: baseline; Post-PD FU1: follow-up after progression. The highlighted areas in gray shade indicate the 25-27% Interquartile Range (IQR) for the data points for each visit for the non-responders dosed at 8 mg/kg, the responders dosed at 16 mg/kg, or the non-responders dosed at 16 mg/kg, respectively. NR: no-responder; R: responder.
Figure 6:
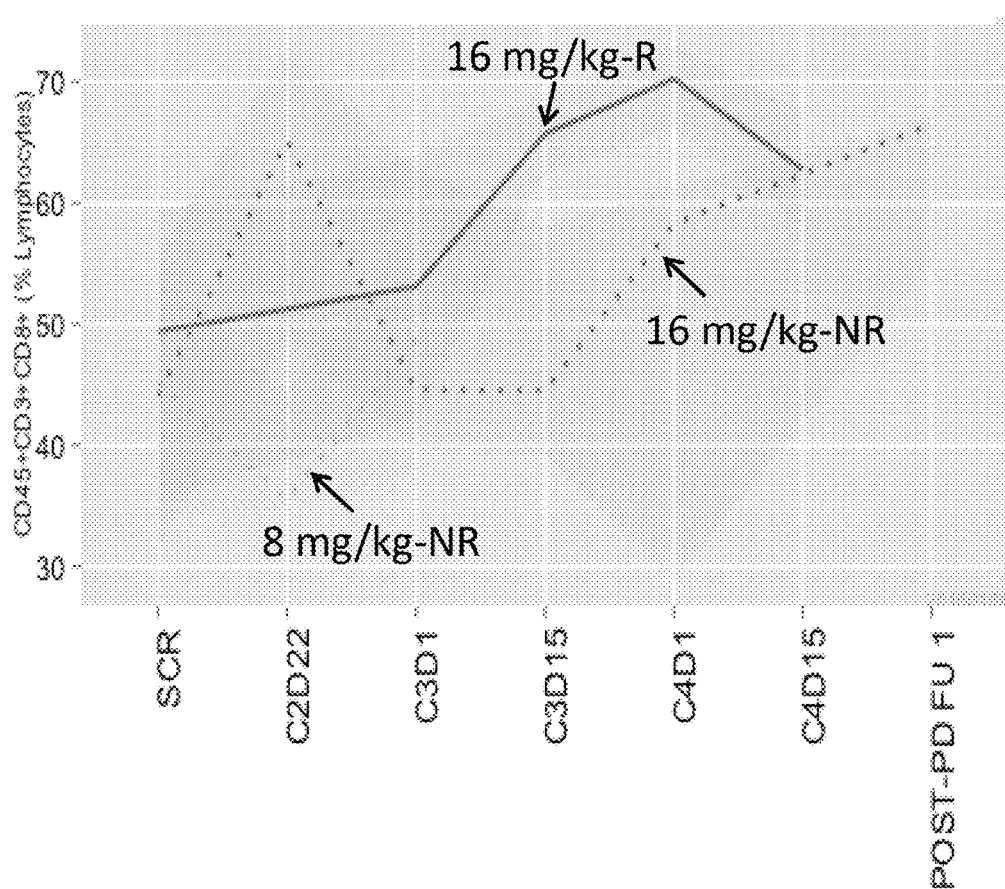
FIG. 6 shows that the number of $CD45^+CD3^+CD8^+$ cells (measured as percentage of lymphocytes) in bone marrow aspirates was increased during DARZALEX™ (daratumumab) treatment over time at doses 8 mg/kg or 16 mg/kg. The graph includes both responders and non-responders as indicated. Study: SIRIUS. The X-axis indicates time expressed as treatment cycle and days of dosing within each treatment cycle (C2D22: cycle 2, day 22; etc). SCR: baseline; Post-PD FU1: follow-up after progression. The highlighted areas in gray shade indicate the 25-27% Interquartile Range (IQR) for the data points for each visit for the non-responders dosed at 8 mg/kg, the responders dosed at 16 mg/kg, or the non-responders dosed at 16 mg/kg, respectively. NR: no-responder; R: responder.

Table 3 shows the Wilcoxon signed-rank test results for the various T cells as % lymphocytes in bone marrow. FIG. 5 shows the percentage (%) of $CD45^+CD3^+$ cells over time during DARZALEX™ (daratumumab) treatment (both responders and non-responders included in the graph). FIG. 6 shows the % $CD45^+CD3^+CD8^+$ cells over time during DARZALEX™ (daratumumab) treatment (both responders and non-responders included in the graph).

TABLE 3

| T cell populations (% lymphocytes) in bone marrow | | | | | |
|---|---|---|---|---|---|
| Sample | | NR: Baseline | NR: On treatment | R: Baseline | R: On treatment |
| $CD45^+CD3^+$/ Lymphocytes | N | 29 | 29 | 19 | 19 |
| | Median | 72.2 | 83.6 | 77.9 | 91.4 |
| | Mean (SD) | 68.57 (13.64) | 80.93 (11.57) | 71.82 (14.92) | 87.67 (9.49) |
| | Range | (36.3; 94.5) | (50.9; 97.4) | (42.2; 94.8) | (63.3; 97.2) |
| | P-value* | | 9.8225e-05 | | 3.8147e-06 |
| $CD45^+CD3^+CD4^+$/ Lymphocytes | N | 29 | 29 | 19 | 19 |
| | Median | 33.7 | 29.2 | 22.7 | 22.8 |
| | Mean (SD) | 31.24 (12.14) | 32.96 (12.57) | 24.18 (7.37) | 24.29 (9.58) |
| | Range | (6.3; 54.2) | (9.6; 60.9) | (8.1; 36.6) | (12.5; 45.4) |
| | P-value* | | 0.18351 | | 0.98432 |
| $CD45^+CD3^+CD8^+$/ Lymphocytes | N | 29 | 29 | 19 | 19 |
| | Median | 36.3 | 43.3 | 49.4 | 66.9 |
| | Mean (SD) | 37.39 (13.64) | 47.74 (18.14) | 46.91 (14.89) | 62.82 (12.79) |
| | Range | (15.9; 67.2) | (18.5; 81) | (24.5; 79.6) | (33.1; 83.3) |
| | P-value* | | 0.00026883 | | 3.8147e-06 |

N: number of samples per group
R: responder
NR: non-responder
*baseline vs. on treatment for responder or non-responder group
SD: standard deviation While both responders and non-responders demonstrated T-cell increases in the peripheral blood and bone marrow, responders had the largest percentage change from baseline. To distinguish whether responders or non-responders had different levels of $CD3^+$, $CD4^+$ and $CD8^+$ T-cells prior to DARZALEX™ (daratumumab) treatment, baseline measurements of each subgroup were compared in the peripheral blood.

There were no statistically significant differences between responders and non-responders in absolute T-cell counts at baseline in peripheral blood (Table 4) or in percentage of T cells from total lymphocytes in bone marrow (Table 5), Wilcoxon signed-rank test.

TABLE 4

| Absolute cell counts in peripheral blood prior to treatment at baseline | | | | | |
|---|---|---|---|---|---|
| Sample | N | Median | Mean (SD) | Range | P-value* |
| $CD45^+CD3^+$: R | 33 | 574 | 715.91 (472.54) | (186; 2096) | |
| $CD45^+CD3^+$: NR | 80 | 638 | 672.5 (426.36) | (85; 2407) | 0.81527 |
| $CD45^+CD3^+CD4^+$: R | 33 | 190 | 276.91 (207.39) | (77; 1085) | |
| $CD45^+CD3^+CD4^+$: NR | 80 | 214 | 251.61 (146.13) | (21; 766) | 0.94965 |
| $CD45^+CD3^+CD8^+$: R | 33 | 332 | 424.55 (324.49) | (93; 1238) | |
| $CD45^+CD3^+CD8^+$: NR | 80 | 318 | 398.14 (354.52) | (43; 2221) | 0.56555 |

N: number of samples per group
R: responder
NR: non-responder
*responder vs non-responder per cell type
SD: standard deviation

TABLE 5

T cells (% lymphocytes) in bone marrow prior to treatment

| Sample | N | Median | Mean (SD) | Range | P-value |
|---|---|---|---|---|---|
| CD45+CD3+: R | 23 | 78.4 | 73.66 (14.43) | (42.2; 94.8) | |
| CD45+CD3+: NR | 65 | 76.5 | 73.5 (13.93) | (36.3; 94.5) | 0.81232 |
| CD45+CD3+CD4+: R | 23 | 25 | 25.57 (8.32) | (8.1; 41.4) | |
| CD45+CD3+CD4+: NR | 65 | 25.3 | 27.53 (12.76) | (6.3; 55.2) | 0.76482 |
| CD45+CD3+CD8+: R | 23 | 50 | 47.7 (13.73) | (24.5; 79.6) | |
| CD45+CD3+CD8+: NR | 65 | 44.3 | 44.73 (15.49) | (15.9; 76.1) | 0.41678 |

Figure 7A:
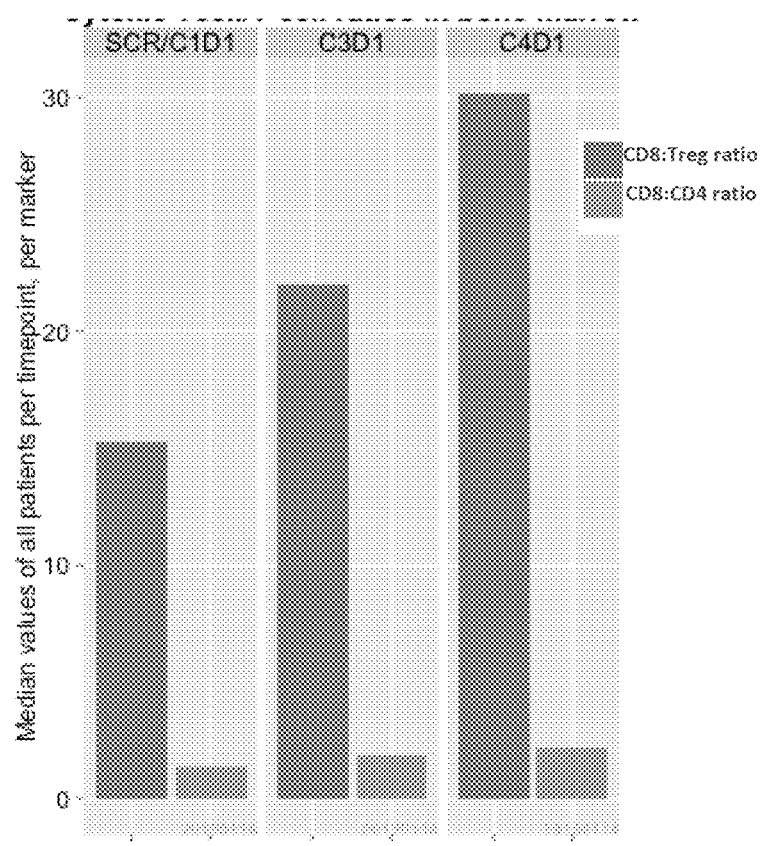
FIG. 7A shows that the ratio of CD8+/Treg and CD8+/$CD4^+$ cells in peripheral blood expressed as median values of all treated patients increased over time during DARZALEX™ (daratumumab) treatment. Time points: C1D1: cycle 1 day; C3D1: cycle 3 day 1; C4D1: cycle 4 day 1. Study: SIRIUS. SRC: baseline.
Figure 7B:
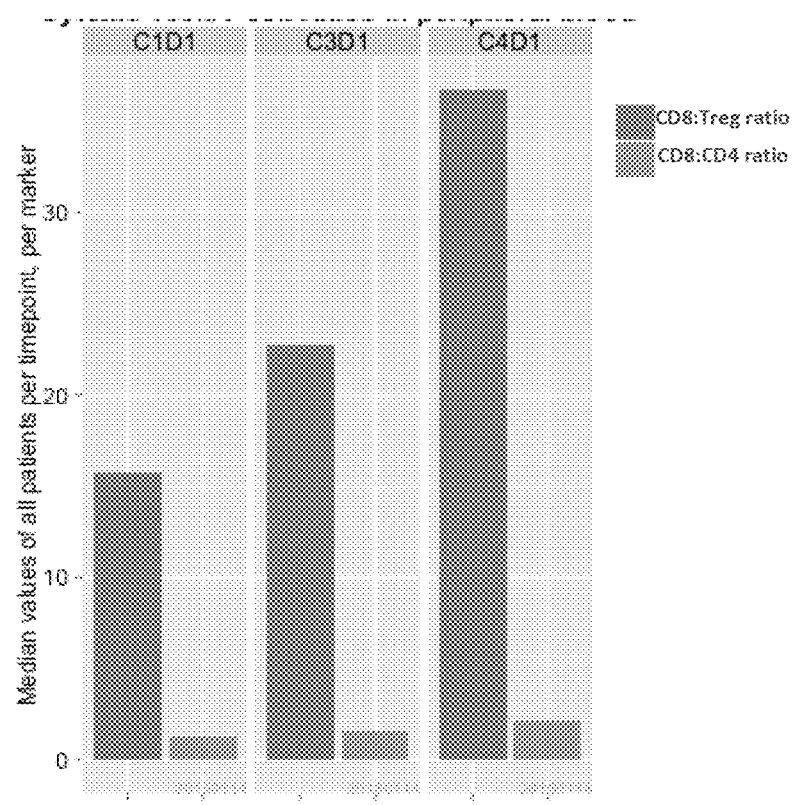
FIG. 7B shows that the ratio of CD8+/Treg cells in bone marrow aspirates expressed as median values of all treated patients increased over time during DARZALEX™ (daratumumab) treatment. Time points: C1D1: cycle 1 day; C3D1: cycle 3 day 1; C4D1: cycle 4 day 1. Study: SIRIUS.

N: number of samples per group
R: responder
NR: non-responder
*responder vs non-responder per cell type
SD: standard deviation T Regulatory Cells Treg cells were identified as the $CD3^+CD4^+CD25^+CD127^{dim}$ cell population in a sample. The ratio of $CD8^+$ T cells to Tregs was assessed in the peripheral blood and bone marrow in patients treated with DARZALEX™ (daratumumab) over time. The ratio increased in both the periphery and bone marrow. FIG. 7A shows the median values of the $CD8^+$/Treg and $CD8^+$/$CD4^+$ cell ratios of all patients per time point in peripheral blood. FIG. 7B shows the median values of the $CD8^+$/Treg and $CD8^+$/$CD4^+$ T-cell ratios of all patients per time point in bone marrow. The changes in the ratios of absolute counts of $CD8^+$ Tregs and $CD8^+$/$CD4^+$ were significant in peripheral blood over time of treatment (Table 6) and in bone marrow (Table 7), Wilcoxon signed-rank test.

In a combined data analyses of SIRIUS and GEN501 study (Example 6), median ratios of $CD8^+$/$CD4^+$ and $CD8^+$/Treg cells in peripheral blood were increased at week 8 ($p=5.1\times10^5$ for $CD8^+$/$CD4^+$ and $p=1.8\times10^{-7}$ for $CD8^+$/Treg) and at week 16 ($p=0.00017$ for $CD8^+$/$CD4^+$ and $p=4.1\times10^{-7}$ for $CD8^+$/Treg). Similarly, in bone marrow, median ratios of $CD8^+$/$CD4^+$ and $CD8^+$/Treg cells were increased on treatment (week 12±1 cycle) compared to baseline ($p=0.00016$ for $CD8^+$/$CD4^+$ and $p=2.8\times10^{-7}$ for $CD8^+$/Treg). No significant differences were observed between responders and nonresponders.

TABLE 6

T cell ratios in peripheral blood

| Sample | N | Median | Mean (SD) | Range | P-value* |
|---|---|---|---|---|---|
| CD8+/CD4+: Baseline | 66 | 119.75 | 191.78 (231.09) | (24.17; 1461.18) | |
| CD8+/CD4+: C3D1 | 66 | 204.86 | 222.96 (167.44) | (25.53; 867.58) | 0.00046409 |
| CD8+/CD4+: C4D1 | 66 | 210.05 | 215.15 (151.31) | (25.86; 798.83) | 0.00042154 |
| CD8+/Tregs: Baseline | 66 | 1258.33 | 2338.46 (3465.12) | (206.82; 18550) | |
| CD8+/Tregs: C3D1 | 66 | 2326.74 | 3361.87 (3661.61) | (155; 23066.67) | 5.25E−06 |
| CD8+/Tregs: C4D1 | 66 | 2763.16 | 3382.86 (3629.69) | (316.67; 22087.5) | 9.95E−08 |

*comparison to baseline;
N: number of samples per group;
SD: standard deviation

TABLE 7

T cell ratios in bone marrow

| Sample | N | Median | Mean (SD) | Range | P-value* |
|---|---|---|---|---|---|
| CD8+/CD4+(/Lymphocytes): Baseline | 31 | 163.18 | 184.4 (129.5) | (32.58; 674.58) | |
| CD8+/CD4+(/Lymphocytes): On treatment | 31 | 221.89 | 240.85 (155.57) | (30.38; 666.4) | 0.0038599 |
| CD8+/Tregs(/Lymphocytes): Baseline | 30 | 1219.58 | 1802.73 (1582.7) | (306.41; 7960) | |
| CD8+/Tregs(/Lymphocytes): On treatment | 30 | 2273.56 | 3905.72 (4232.73) | (451.22; 20825) | 3.15E−07 |

*comparison to baseline;
N: number of samples per group;
SD: standard deviation

Example 4. Study Design (GEN501)

Study GEN501 (NCT00572488) evaluated DARZALEX™ (daratumumab) as monotherapy in double-refractory MM patients. Sample isolation, processing and statistical analyses was as described in Example 1 and Example 2. The study has been described in Lokhorst et al., N Eng J Med 373:1207-19, 2005.

Briefly, Study GEN501 was the first-in-human clinical study of DARZALEX™ (daratumumab) in subjects with MM. It is a Phase 1/2, dose-escalation, safety study divided into 2 parts. Part 1 is an open-label, dose-escalation study; Part 2 is an open-label, single-arm study with multiple cohorts, based on the dose levels established in Part 1

In Part 1, 10 dose levels of DARZALEX™ (daratumumab) were evaluated: 0.005, 0.05, 0.10, 0.50, 1, 2, 4, 8, 16, and 24 mg/kg. The 2 lowest dose cohorts were allocated 1 (+3) subject(s) each, and a standard 3 (+3) subject allocation was applied to the remaining 8 dose cohorts. Part 2 was an open-label, single study including two dose levels, 8 mg/kg and 16 mg/kg. Part 1 included 32 subjects and Part 2 included 72 subjects.

Example 5. DARZALEX™ (Daratumumab) Treatment Induces T Cell Clonality in Patients Given the expansion of $CD8^+$ T-cells noted in both the periphery and the bone marrow in the MY2002 study, high throughput next-generation sequencing of the T-cell receptor (TCR) was performed using the Immunoseq™ assay to determine whether expanding $CD8^+$ T-cells were clonal in nature, indicative of an adaptive immune response. Total of 17 patient samples of subjects who were enrolled in the GEN501 study were evaluated (n=6 responders i.e., ≥ PR; n=1 non-responders i.e., MR, SD, PD).

Figure 8A:
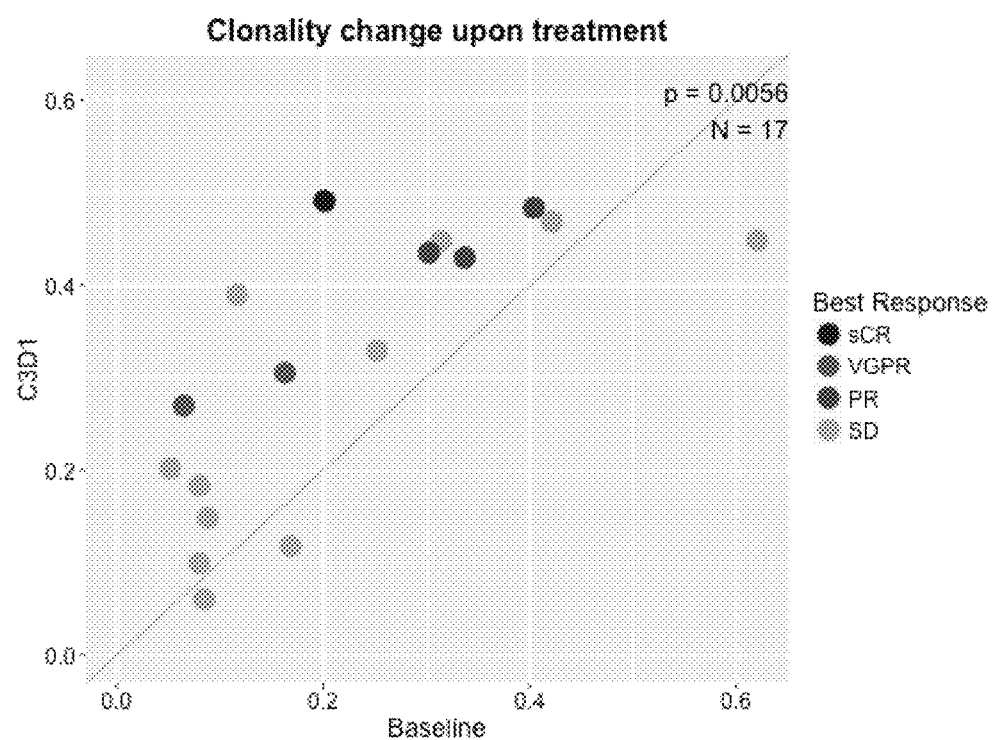
FIG. 8A shows that responders had increased $CD8^+$ T-cell clonality when compared to non-responders, as measured using % change in abundance (CIA) of particular clonal cells. Study: GEN501 17 patient subset.
Figure 8B:
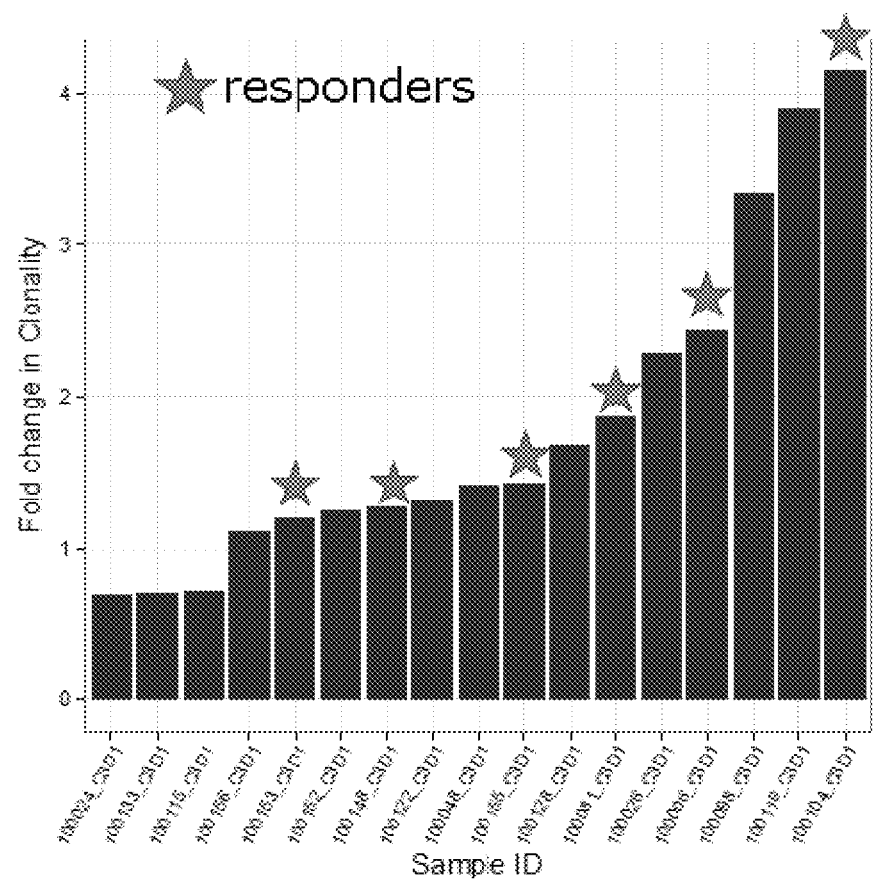
FIG. 8B shows the fold change in $CD8^+$ T-cell clonality in individual patients pre- vs. post DARZALEX™ (daratumumab) treatment. Responders are indicated with the star. Clonality was measured as fold change in abundance (CIA) of particular clonal cells. Study: GEN501 17 patient subset.

TCR sequencing revealed that DARZALEX™ (daratumumab) treatment significantly increased clonality across patients. FIG. 8A shows the correlation between T cell clonality pre- vs. post-DARZALEX™ (daratumumab) treatment (p=0.0056). FIG. 8B shows the fold change in clonality in individual patients. Responders are marked with the star. This data suggests that the T cell expansion noted with DARZALEX™ (daratumumab) treatment may be clonal in nature.

Figure 8C:
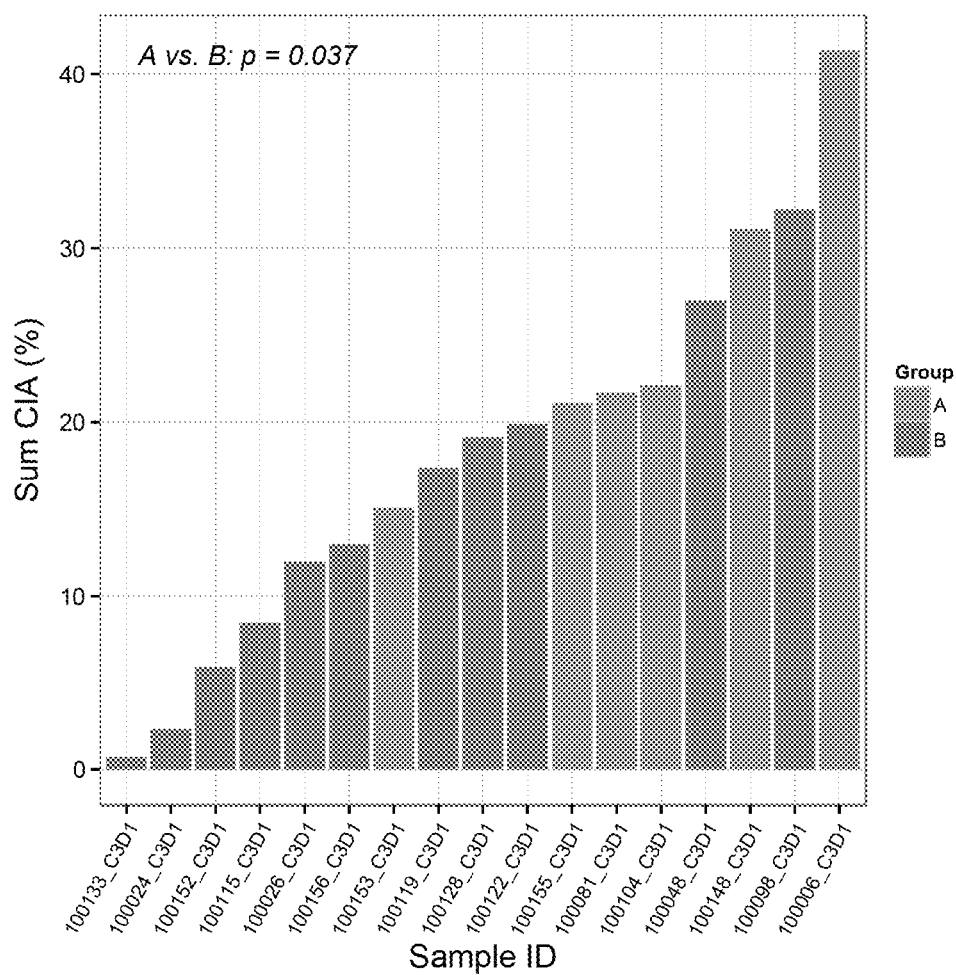
FIG. 8C shows that responders (Group A) had greater total expansion in the TCR repertoire, measured using CIA (change in abundance) when compared to non-responders (Group B). P=0.037. Study: GEN501 17 patient subset.
Figure 8D:
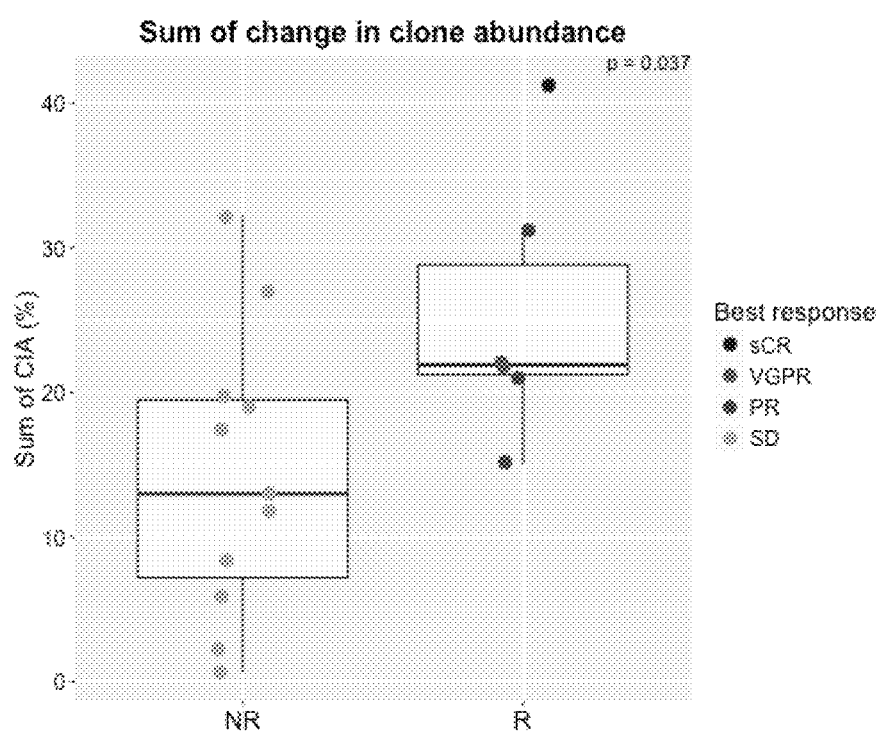
FIG. 8D shows the sum of absolute change in abundance (CIA) in responders and non-responders for each expanded T cell clone. P=0.035 between responders (Group A) and non-responders (Group B). Study: GEN501 17 patient subset.
Figure 8E:
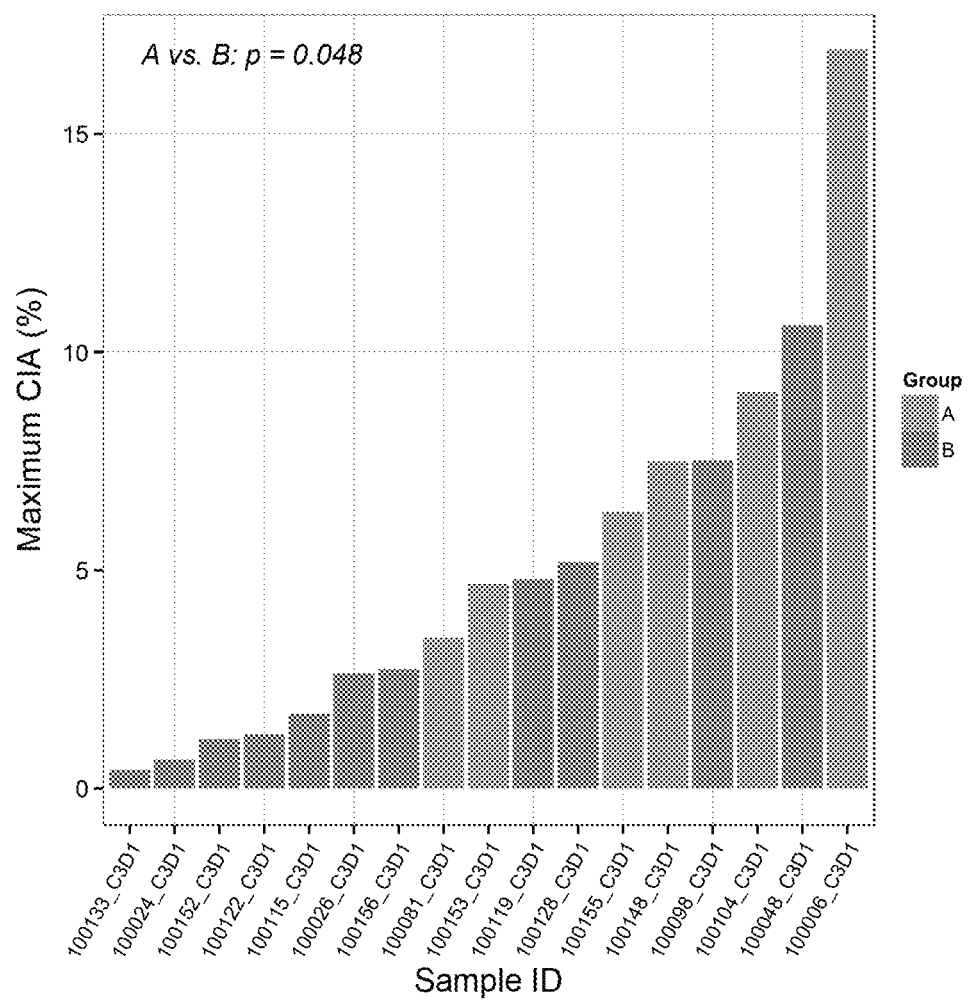
FIG. 8E shows the maximum CIA of a single T-cell clone in responders (Group A) and non-responders (Group B). Study: GEN501 17 patient subset.
Figure 8F:
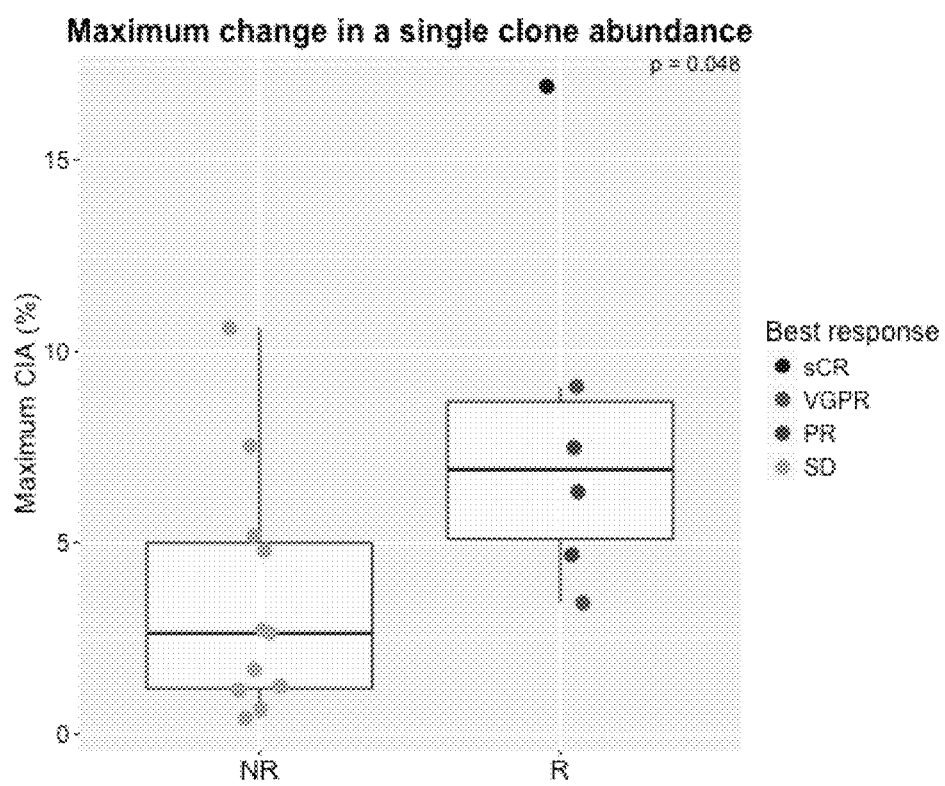
FIG. 8F shows that responders (Group A) had greater maximum expansion of a single clone, measured using maximum % CIA, when compared to non-responders (Group B). P=0.0477. Study: GEN501 17 patient subset.

Responders had a greater total expansion in the TCR repertoire (as measured by change in abundance; CIA) when compared to non-responders. FIG. 8C shows the % CIA for individual patients. Group A: responders, Group B: non-responders. Statistically significant difference was observed between responders and non-responders (p=0.037). FIG. 8D shows the sum of absolute change in abundance (CIA) in responders and non-responders for each expanded T cell clone. FIG. 8E shows the maximum % CIA for each individual patient. Group A: responders, Group B: non-responders. Statistically significant difference was observed between responders and non-responders (p=0.048). FIG. 8F shows the maximum CIA of a single T-cell clone in responders (Group A) and non-responders (Group B).

CIA was obtained by identifying significant differences in clonal abundance between two samples using Fisher's exact test (DeWitt et al. J. Virol. 2015) and summing the absolute change in abundance for each expanded clone.

Example 6. Immunomodulatory Effects of DARZALEX™ (Daratumumab) in Patients Enrolled in the GEN501 Study Various T and B cell populations were evaluated in responders and non-responders enrolled in the GEN501.

Lymphocytes

Similar to SIRIUS (MMY2002) study, lymphocytes were increased in both peripheral blood and bone marrow during DARZALEX™ (daratumumab) treatment. This increment was attributed to increased numbers of both $CD4^+$ and $CD8^+$ cells.

$CD8^+$ Central Memory Cells $CD8^+$ T-cell phenotype was studied in patients treated with DARZALEX™ (daratumumab) over time in a subset of 17 patients enrolled in the GEN 501 study. $CD8^+$ cells from patients were identified as naïve ($CD45RO-/CD62L^+$) ($T_N$) or central memory ($T_{CM}$) ($CD45RO^+/CD62L^{+high}$) cells using standard protocols.

Figure 9A:
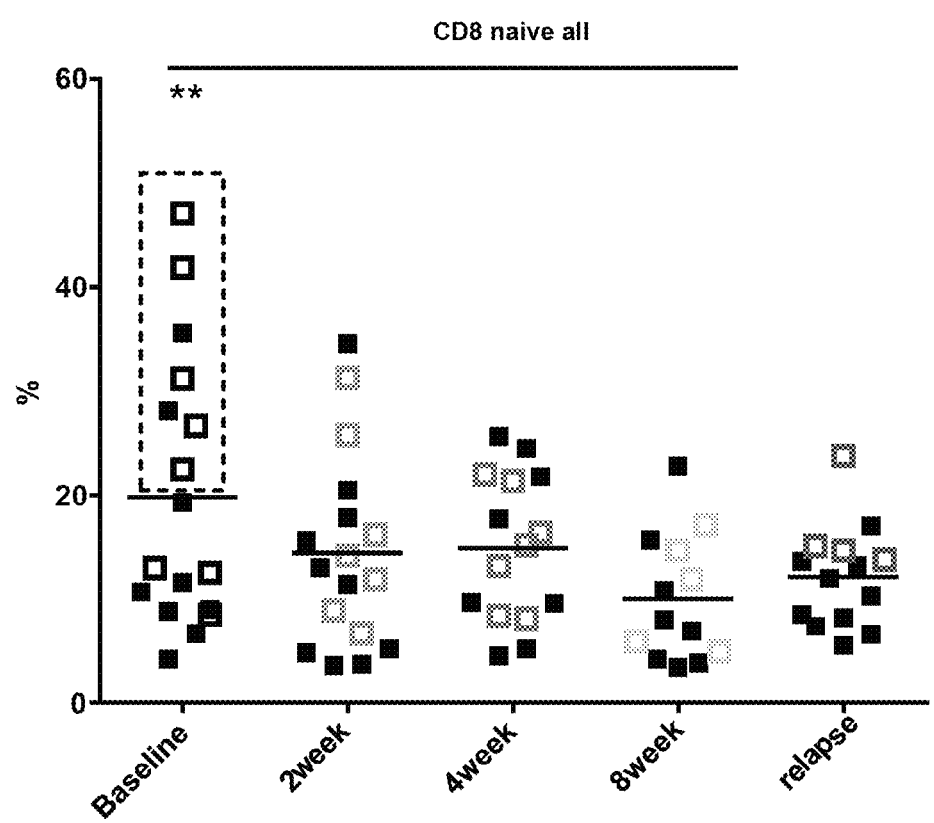
FIG. 9A shows the percentage (%) of $CD8^+$ naïve cells in peripheral blood in non-responders (NR, black squares) and in patients having at least minimal response (MR, white squares) to DARZALEX™ (daratumumab) at baseline, or at 2 weeks, 4 weeks or 8 weeks of treatment, or after relapse. Study: GEN501 17 patient subset. **p=$1.82 \times 10^{-4}$.
Figure 9B:
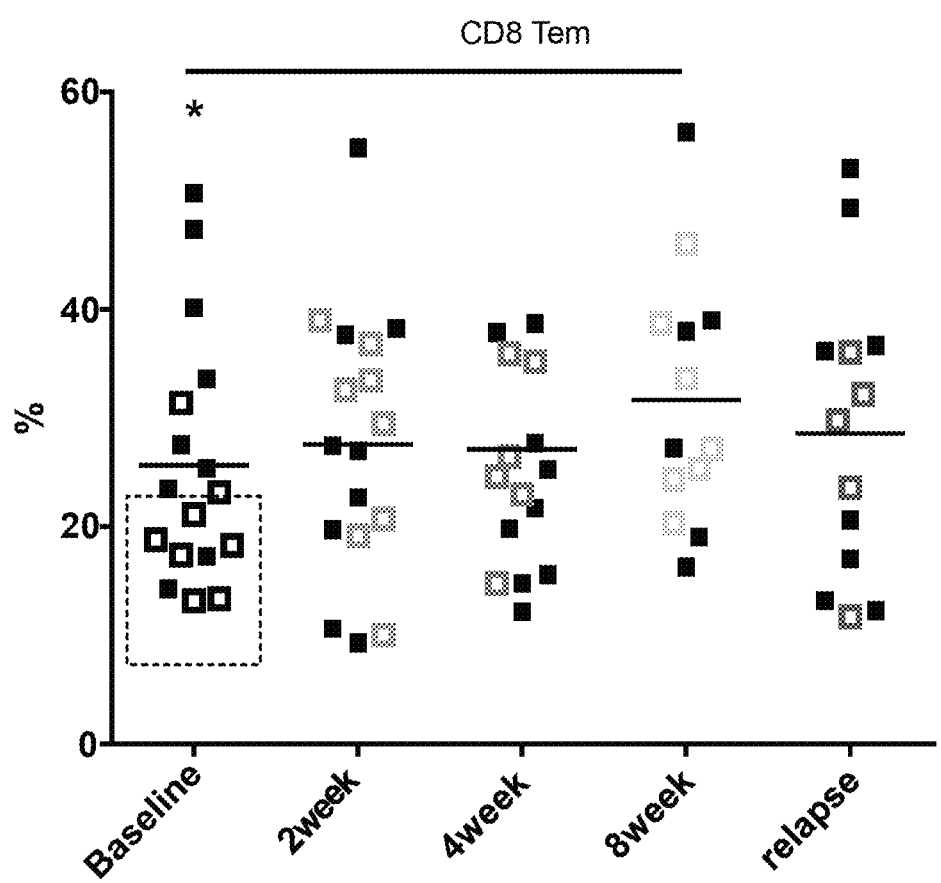
FIG. 9B shows the percentage of $CD8^+$ central memory cells (Tem) in peripheral blood in non-responders (NR, black squares) and in patients having at least minimal response (MR, white squares) to DARZALEX™ (daratumumab) at baseline, or at 2 weeks, 4 weeks or 8 weeks of treatment, or after relapse. Study: GEN501 17 patient subset. *p=$4.88 \times 10^{-2}$.
Figure 9C:
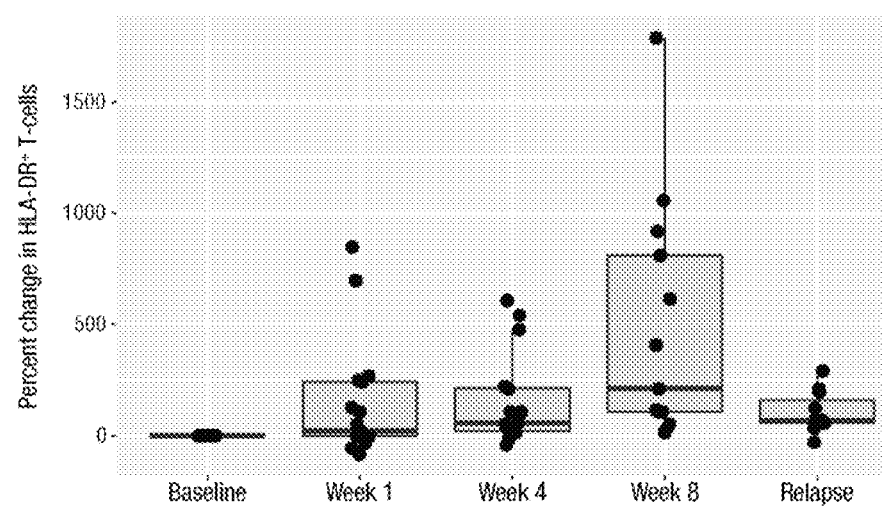
FIG. 9C shows the percentage increase of HLA Class I restricted $^{CD8+}$ T cells in peripheral blood at baseline, or at week 1, 4 or 8 of treatment, or after relapse. Study: GEN501 17 patient subset.
Figure 9D:
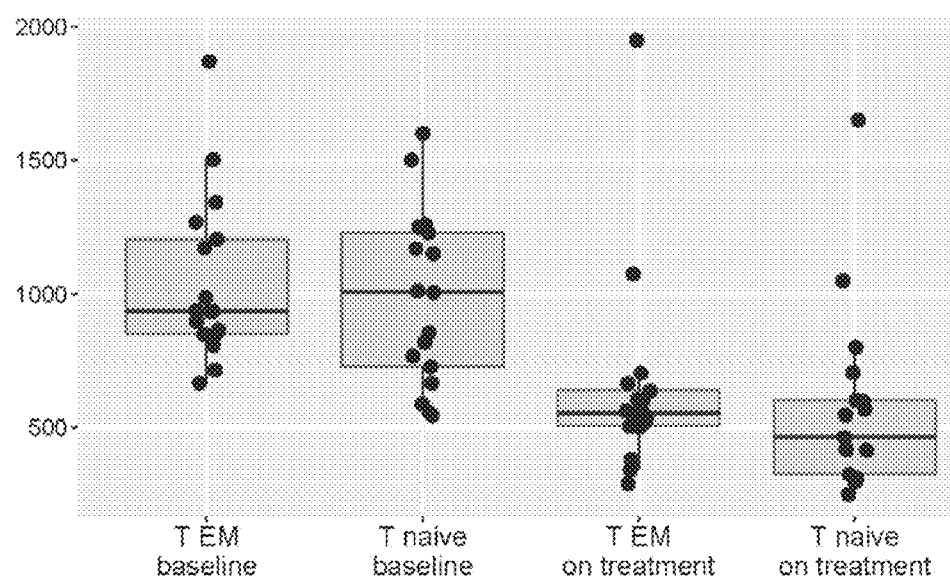
FIG. 9D shows that CD38 is expressed at low levels in $CD8^+$ naïve T cells and in $CD8^+$ central memory cells (Tem) in peripheral blood at baseline or on treatment. Study: GEN501 17 patient subset. MFI: Mean fluorescent intensity.

FIG. 9A shows the % of $CD8^+$ naïve cells (% of $CD8^+$ cells) and FIG. 9B shows the % of $CD8^+$ central memory cells. DARZALEX™ (daratumumab) treatment significantly decreased the quantity of naïve $CD8^+$ T cells (p=$1.82 \times 10^{-4}$ at Week 8) and increased the quantity of $CD8^+$ memory T cells (p=$4.88 \times 10^{-2}$ at Week 8). This would suggest a transition from naïve cytotoxic T cells to memory T cells which may be activated against a specific antigen. White squares indicate patients that achieved at least a minimal response (≥MR) and black squares indicate patients that had stable disease or progressive disease. A significantly greater decrease in $CD8^+$ naïve T cells was apparent in patients who responded to treatment (data not shown). FIG. 9C shows that DARZALEX™ (daratumumab) treatment increased the percentage in HLA Class I-restricted T cells, which partially drive the virus-specific and alloreactive T cell responses. FIG. 9D shows that the expanding effector memory T cells expressed low levels of CD38. It is important to note that these T cells display normal and even increased functional activity against viral peptides and alloantigens (see Example 8). From these functional results we concluded that there is an expansion of, or improved activity of, antigen-experienced T cells against viral and alloantigens during DARZALEX™ (daratumumab) treatment. These data suggest that, unlike regulatory cell subsets, effector T cells do not need CD38 expression to properly function and expand.

CD38-Positive Regulatory T-Cells

The observation of the robust expansion and increased activity of cytotoxic T-cells together with recent literature indicating that several immune-suppressive cell subsets express CD38 prompted examination of the effects of DARZALEX™ (daratumumab) on regulatory cell populations regulatory T-cells (Tregs), myeloid derived suppressor cells (MDSCs) and regulatory B-cells (Bregs).

Regulatory T-cells (Tregs) ($CD3^+CD4^+CD25^+CD127^{dim}$) were isolated using standard protocols. The frequency of the Tregs was analyzed using flow cytometery.

Figure 10A:
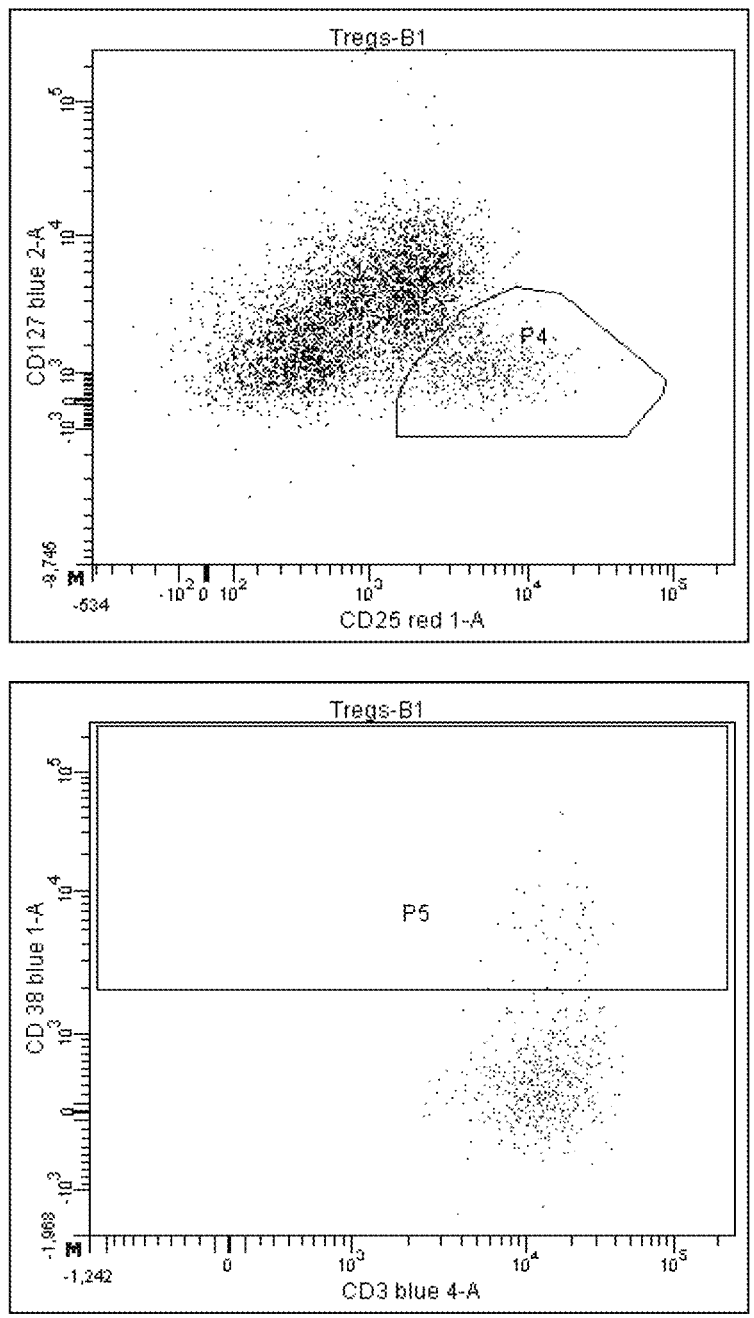
FIG. 10A shows a histogram of FACS analyses showing frequency of Tregs ($CD3^+CD3^+CD4^+CD25^+CD127^{dim}$ (top histogram, P4 cell population) and the frequency of $CD38^+$ Tregs within the Treg population (bottom histogram, P5 cell population) in multiple myeloma patients at baseline. Study: GEN501 17 patient subset.
Figure 10B:
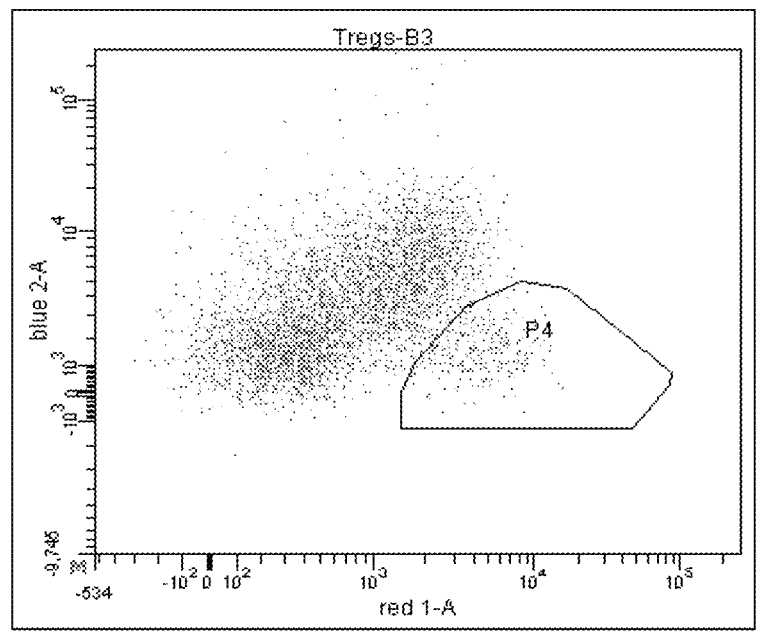
FIG. 10B shows a histogram of FACS analyses showing frequency of Tregs ($CD3^+CD3^+CD4^+CD25^+CD127^{dim}$ (top histogram, P4 cell population) and the frequency of $CD38^+$ Tregs within the Treg population (bottom histogram, P5 cell population) in multiple myeloma patients after DARZALEX™ (daratumumab) treatment. DARZALEX™ (daratumumab) treatment depleted $CD38^+$ Tregs. Study: GEN501 17 patient subset.
Figure 10B:
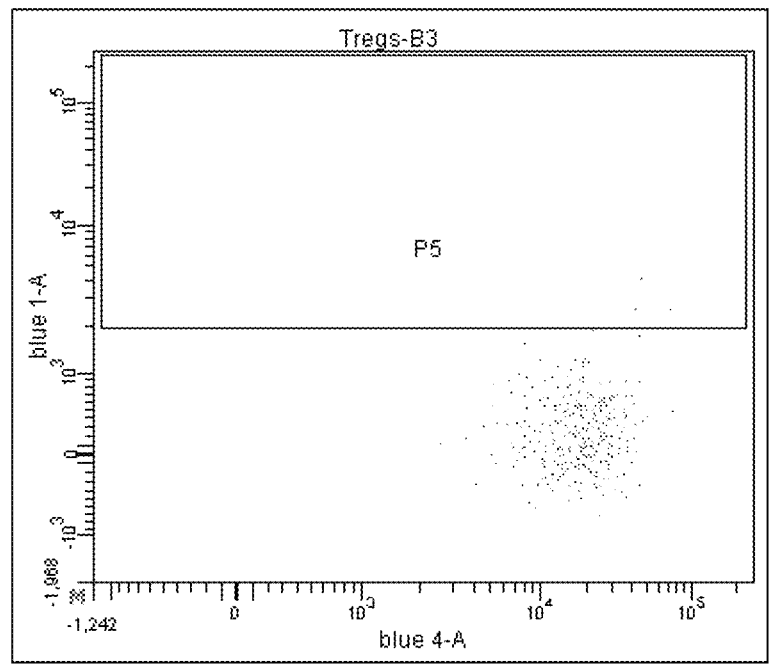
Figure 10C:
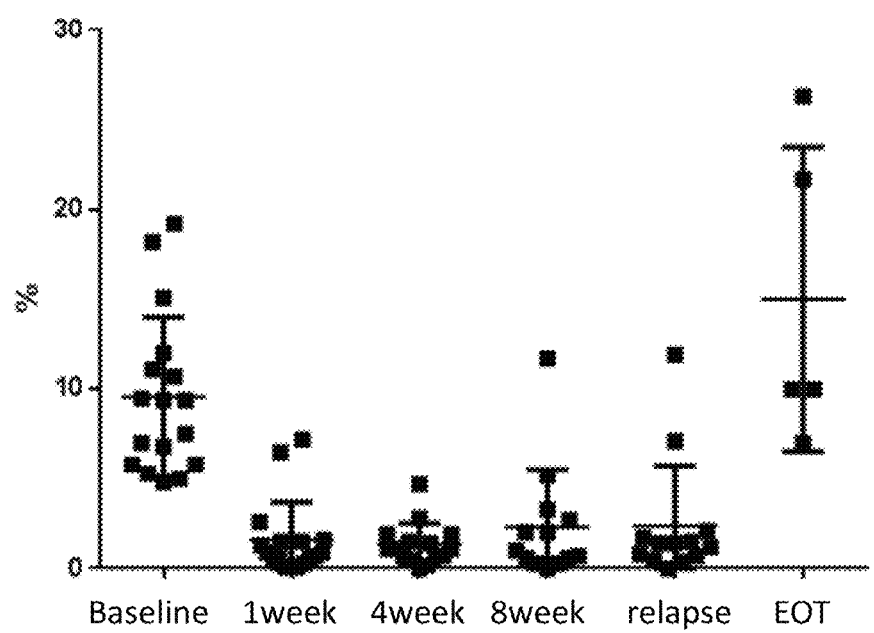
FIG. 10C shows that frequency of the $CD38^{high}$ $CD3^+$ $CD4^+CD25^+CD127^{dim}$ Tregs in patients treated with DARZALEX™ (daratumumab) at baseline, or at 1 week, 4 week, 8 weeks, after relapse or at end of treatment at 6 months (EOT). CD38$^{high}$ Treg frequency was reduced with DARZALEX™ (daratumumab) treatment and returned to baseline at EOT. Y-axis: % of CD38$^{high}$CD3$^+$CD4$^+$CD25$^+$ CD127$^{dim}$ Tregs from CD3$^+$ T-cells. Study: GEN501 17 patient subset.
Figure 10D:
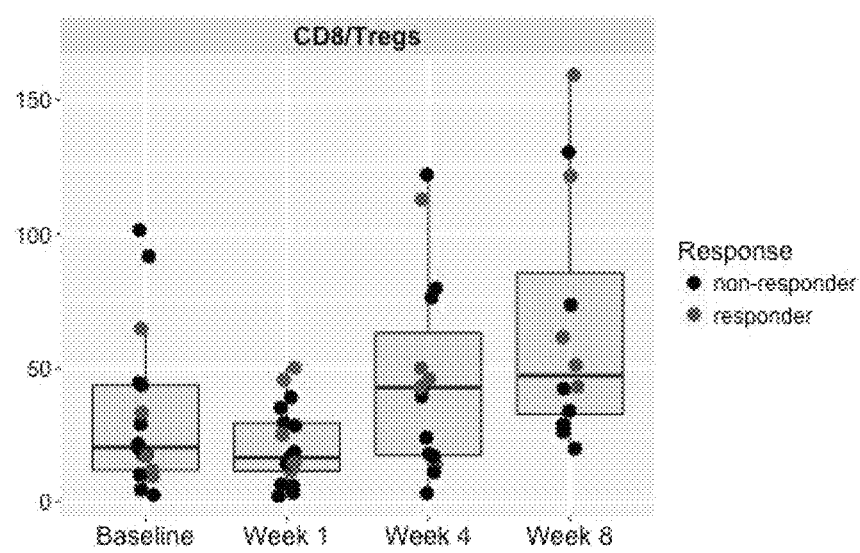
FIG. 10D shows the CD8+/Treg cell ratio in responders and non-responders at baseline, at 1 week, 4 weeks and 8 weeks of treatment. The CD8+/Treg cell ratio was significantly higher in responders vs. non-responders (p=0.00955) at Week 8 of treatment. Study: GEN501 17 patient subset.

A subpopulation of peripheral Tregs (10%±10%) expressed high levels of CD38 prior to Treg activation. FIG. 10A, top panel shows the frequency of the Tregs in the $CD3^+CD4^+$ cell population (P4 cell population) at baseline. FIG. 10A, bottom panel shows the subset of Tregs expressing high CD38 (P5 cell population). These $CD38^+$ Tregs were highly sensitive to DARZALEX™ (daratumumab) treatment and exhibited a significant and almost immediate decline following the first dose of DARZALEX™ (daratumumab) (n=17 patients; P=$8.88 \times 10^{-16}$ at Week 1 versus baseline). The frequency of Tregs after DARZALEX™ (daratumumab) treatment is shown in FIG. 10B, top panel (P4 cell population). FIG. 10B, bottom panel shows that the $CD38^{high}$Tregs (P5 cells) was the most significantly depleted Treg population after $1^{st}$ DARZALEX™ (daratumumab) infusion. These $CD38^+$ Tregs remained depleted throughout DARZALEX™ (daratumumab) treatment (p=8.88×10⁻¹⁶, 1.11×10⁻¹⁵, and 1.50×10⁻¹¹ at Weeks 1, 4, and 8, respectively, versus baseline. FIG. 10C shows the % of CD38$^{high}$ Tregs from total CD3⁺ cells at baseline, week 1, week 4, week 8, relapse, and 6 months after the end of treatment (EOT). The CD38$^{high}$ Tregs were recovered to the baseline at that time point. Changes in CD38⁺ Tregs were similar between patients who did and did not respond to treatment however, the CD8⁺ T-cell:Treg ratio was significantly higher at Week 8 in patients who showed a response to DARZALEX™ (daratumumab) (P=0.00955; FIG. 10D).

Figure 10E:
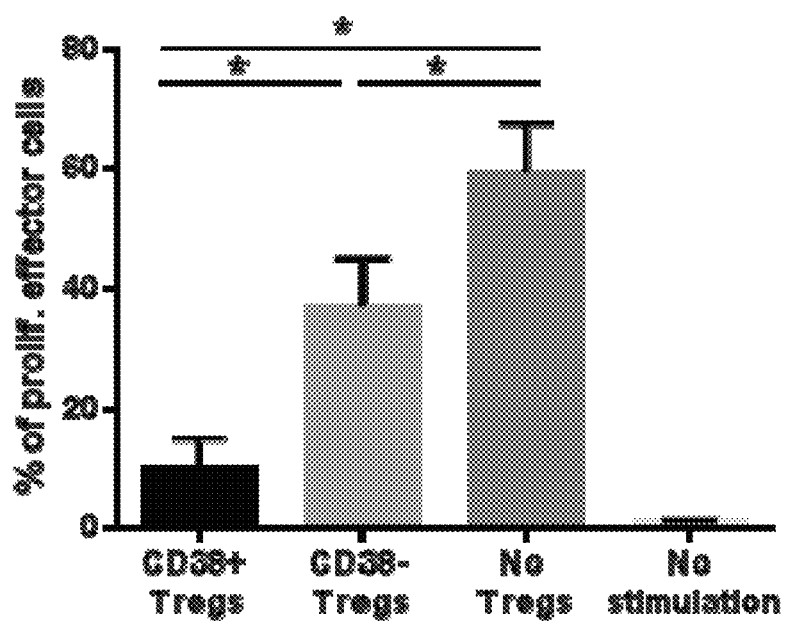
FIG. 10E shows that effector cell proliferation is inhibited more efficiently in the presence of CD38$^+$ Tregs when compared to the CD38$^-$ Tregs or negative controls. Error bars represent standard error. Asterisks denote significant changes. Samples were obtained from multiple healthy donors. Cell proliferation was assessed through the dilution of carboxyfluorescein succinimidyl ester (CFSE).

To assess the possible biological relevance of depletion of CD38⁺ Tregs with DARZALEX™ (daratumumab) treatment, the suppressive capacity of CD38⁺ Tregs versus CD38⁻ Tregs on autologous CD3⁺ T cells was assessed. In a series of experiments performed with sample from multiple healthy donors, CD38⁺ Tregs suppressed T-cell proliferation more robustly (9.9% cell proliferation observed) than CD38 Tregs (53.2% cell proliferation observed) or the negative control (74.9% cell proliferation observed) (FIG. 10E).

Figure 11:
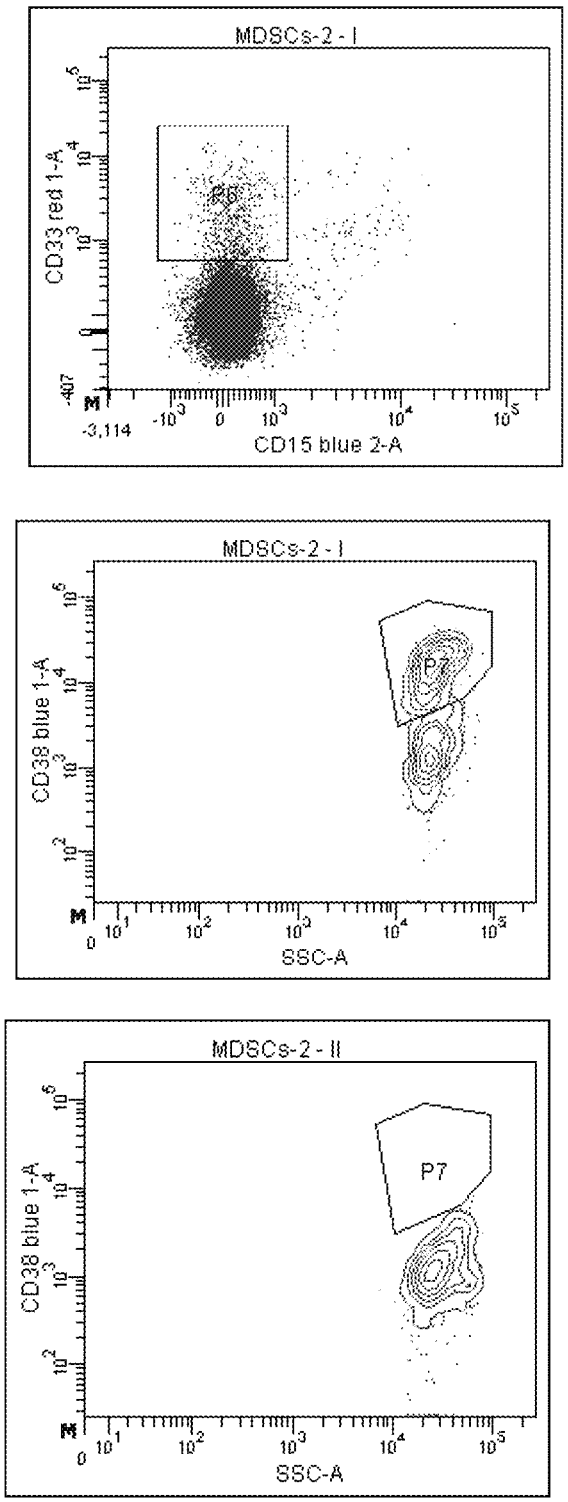
FIG. 11 shows that Myeloid-derived suppressor cells (MDSC) are present in multiple myeloma patients (top graph, boxed cells) and that about half of the cells expressed CD38 (middle graph, boxed cells). The CD38high MDSC population was depleted in patients treated with one infusion of DARZALEX™ (daratumumab) (bottom graph, boxed cells). Study: GEN501 17 patient subset.

Since MDSCs were not readily detectable in frozen PBMC samples, CD38⁺ granulocytic MDSCs (CD 11b⁺ CD14⁺HLA-DR⁻CD15⁺CD33⁺) were generated in vitro from PBMCs isolated from patients at baseline and from patients who had received one infusion of DARZALEX™ (daratumumab). FIG. 11 shows the flow cytometry histogram of identified MDSCs (FIG. 11, top histogram, boxed cell population). Approximately half of the MDSCs expressed CD38 (FIG. 11, middle graph; circled P7 cell population). The CD38$^{high}$ MDSCs were nearly depleted in patients treated with DARZALEX™ (daratumumab) (FIG. 11, bottom graph; circled P7 cell population).

Figure 12:
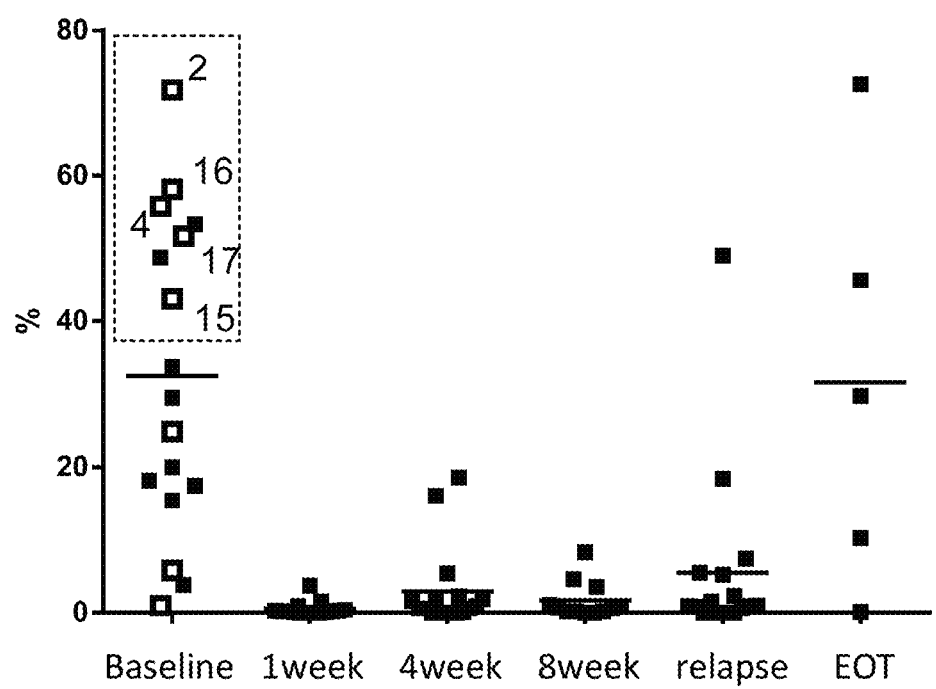
FIG. 12 shows that the number of CD38high MDSCs (CD11b$^+$HLADR$^-$CD14$^-$ CD33$^+$CD15$^+$) was reduced in patients after 1 week, 4 week or 8 week treatment with DARZALEX™ (daratumumab) when compared to the baseline, and returned to close to baseline after end of treatment (EOT). Relapsed patients still demonstrated reduced CD38high MDSCs. Black squares: non-responders; white squares: patients with at least Minimal Response to DARZALEX™ (daratumumab) treatment. The vertical lines indicate the median values in each group. Patients 2, 4, 15, 16 and 17 demonstrated high initial CD38high MDSCs population. Study: GEN501 17 patient subset.

The CD38$^{high}$ lineage nonspecific MDSCs were depleted with DARZALEX™ (daratumumab) treatment over time in both non-responders and patients who have at least Minimal Repose to treatment. FIG. 12 shows that the percentage of the CD38$^{high}$ MDSCs was reduced to nearly 0% in patients at 1 week, 4 weeks or 8 weeks of treatment. The CD38$^{high}$ lineage nonspecific MDSCs returned to baseline after the end of treatment.

Figure 13:
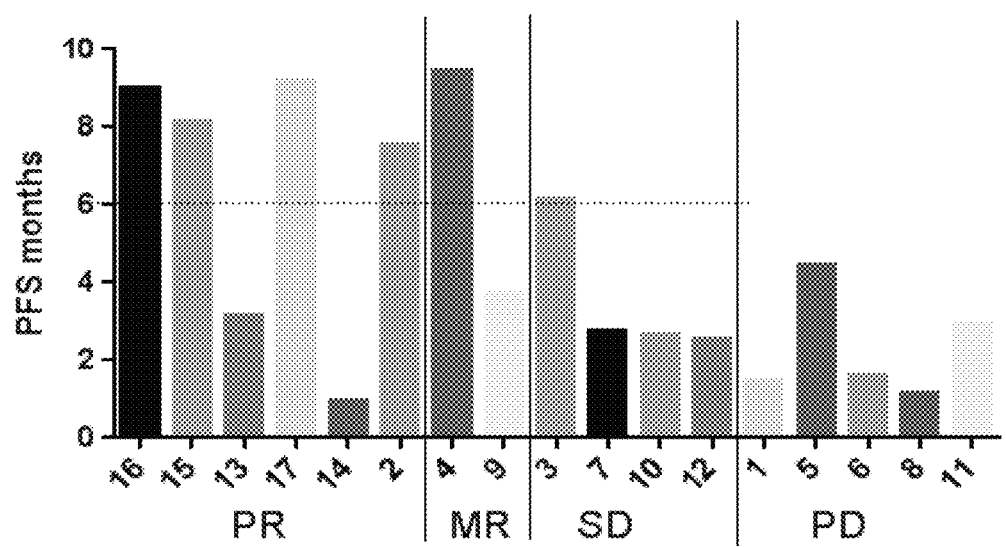
FIG. 13 shows that the patients with highest CD38high MDSCs (patients 2, 4, 15, 16 and 17) had the highest Progression-Free Survival (PFS). These patients had either partial Response (PR) or Minimal Response (MR) to DARZALEX™ (daratumumab) treatment. SD: Stable Disease; PD: Progressive Disease. X-axis shows the PFS for each individual numbered patient.

Patients with the largest CD38⁺ populations within lineage nonspecific MDSC's demonstrated the best and most durable responses to DARZALEX™ (daratumumab) treatment. FIG. 13 shows that the patients 2, 4, 15, 16 and 17 having the highest percentage of CD38$^{high}$ MDSC (as shown in FIG. 11) and classified as patients with PR or MR, had a Progression-Free Survival (PFS) of at least 8 months.

Figure 14:
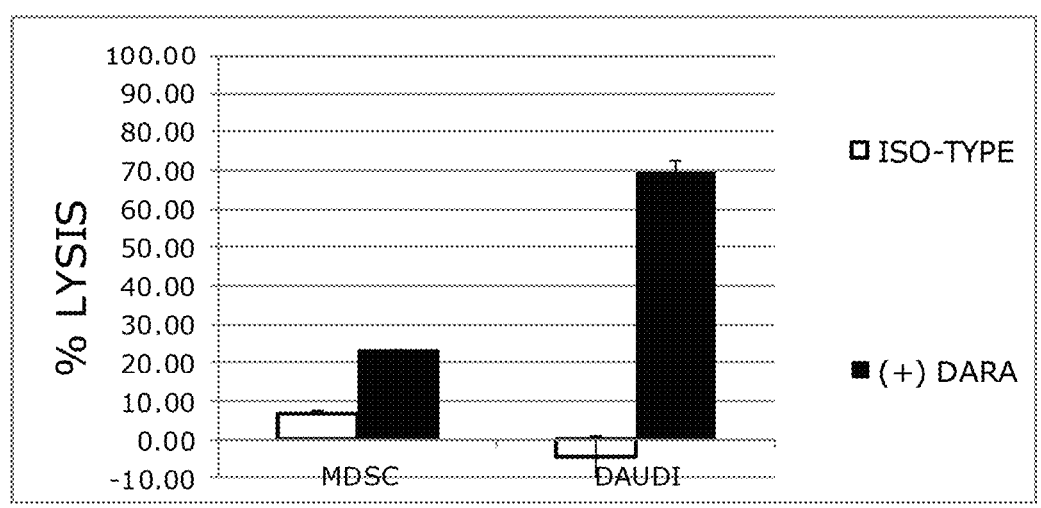
FIG. 14 shows that MDSC are sensitive to DARZALEX™ (daratumumab)-induced ADCC. Daudi cells were used as positive control for target cells in the assays. % cell lysis was measured.

The CD38$^{high}$ lineage nonspecific MDSCs were also sensitive to DARZALEX™ (daratumumab)-induced ADCC in vitro. ADCC assays were performed using CD38$^{high}$MDSCs from two donors and Daudi cells as control target cells with effector:target cell ratio of 50:1. FIG. 14 shows the results of the experiment from one donor. DARZALEX™ (daratumumab) induced lysis of MDSC cells.

Figure 15A:
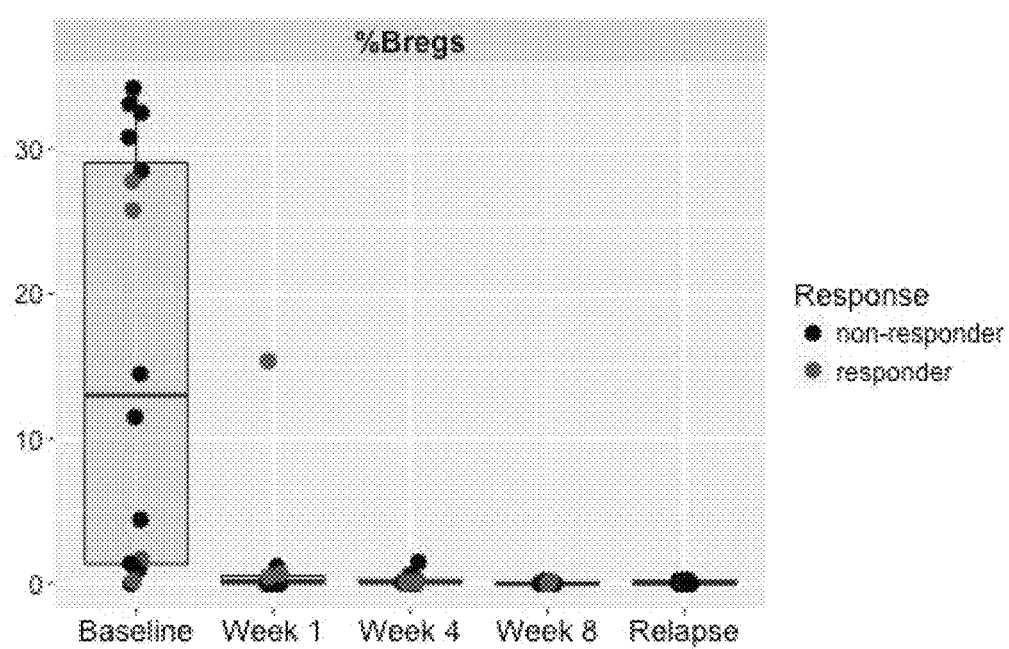
FIG. 15A shows that CD38$^+$ Bregs were depleted in patients treated with DARZALEX™ (daratumumab) at Week, Week 4 and Week 8 of treatment.
Figure 15B:
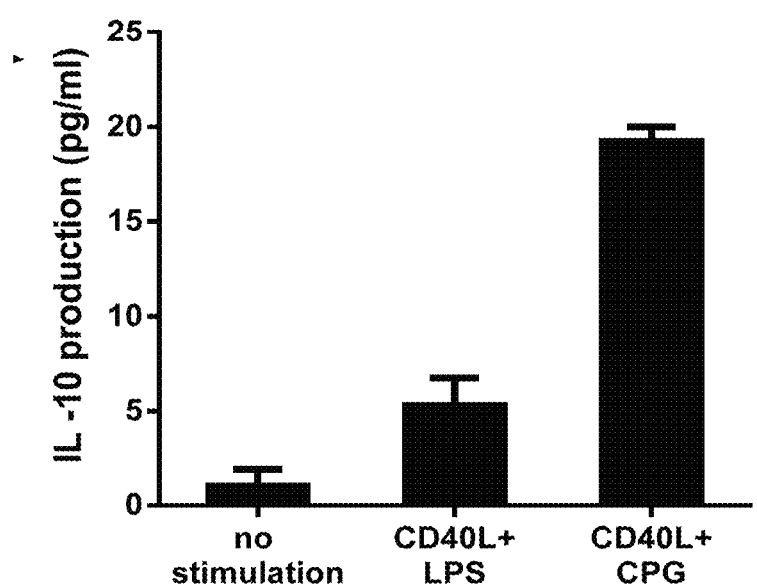
FIG. 15B shows that CD38$^+$ Bregs secrete IL-10 upon stimulation.

CD38⁺ Bregs were measured in DARZALEX™ (daratumumab)-treated patients (n=16) and, similar to CD38⁺ Tregs, were depleted following the first dose of DARZALEX™ (daratumumab) (p=0.0018 at Week 1 compared with baseline; paired Wilcoxon rank test) and remained low while patients were on treatment (FIG. 15A). The FACS sorted Bregs, when stimulated, produced IL-10 (FIG. 15B).

Collectively, these observations suggest that the depletion of immunosuppressive CD38⁺ MDSCs, Bregs, and Tregs is a significant contributory mechanism to DARZALEX™ (daratumumab)-induced changes in T-cell populations and clonality.

Example 7. CD38⁺ MDSC Cells are Present in Cancer Patients

Percentage of MDSC (Lin⁻CD14⁻HLADR$^{low/-}$) and their CD38 expression was studied in in the peripheral blood of patients with NSCLC or prostate cancer using flow cytometry.

The percentage of MDSCs was between about 10%-37% and between about 10%-27% of PBMCs in the analyzed samples from the NSCLC and prostate cancer patients, respectively. CD38 expression was identified in 80-100% of Lin⁻CD14⁺HLADR$^{-/low}$MDSCs from PBMCs from NSCLC patients and in 70-100% of MDSCs from PBMCs from prostate cancer patients.

Example 8. DARZALEX™ (Daratumumab) Enhances Antiviral T-Cell Responses

Figure 16A:
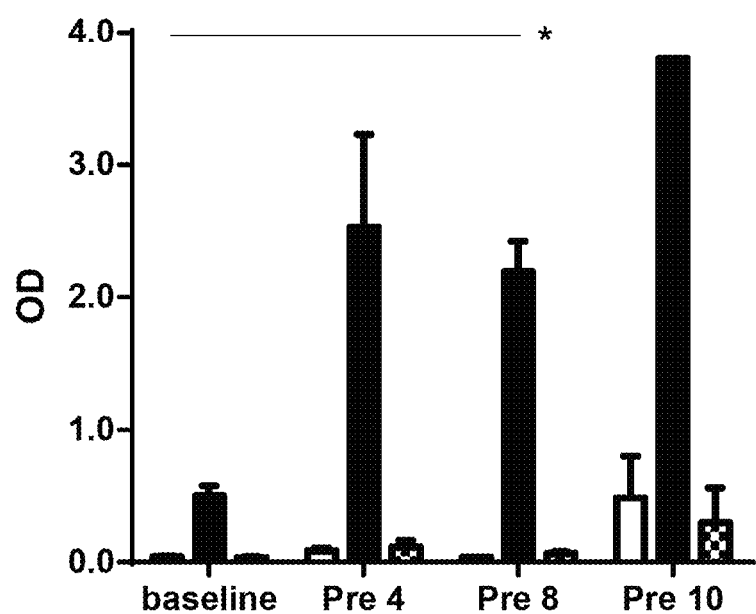
FIG. 16A shows the anti-viral response measured through CMV, EBV and influenza virus specific (CEF) IFN-γ production in PBMCs from DARZALEX™ (daratumumab) treated patient with VGPR at baseline and at indicated times during treatment. OD: optical density. White bar: negative control; black bar: CEF added; dashed bar: allogeneic PBMCs only. Asterix indicates a statistically significant change. Pre 4, 8, 10=Week 4, 8 or 10 of treatment.
Figure 16B:
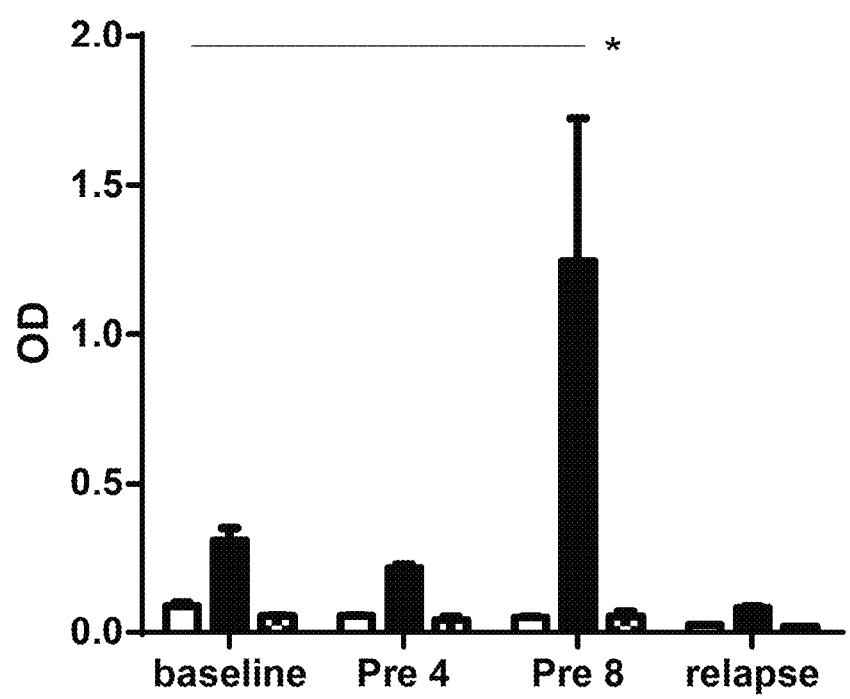
FIG. 16B shows the anti-viral response measured through CMV, EBV and influenza virus specific (CEF) IFN-γ production in PBMCs from DARZALEX™ (daratumumab) treated patient with CR at baseline and at indicated times during treatment. OD: optical density. White bar: negative control; black bar: CEF added; dashed bar: allogeneic PBMCs only. Asterix indicates a statistically significant change. Pre 4, 8, 10=Week 4, 8 or 10 of treatment.
Figure 16C:
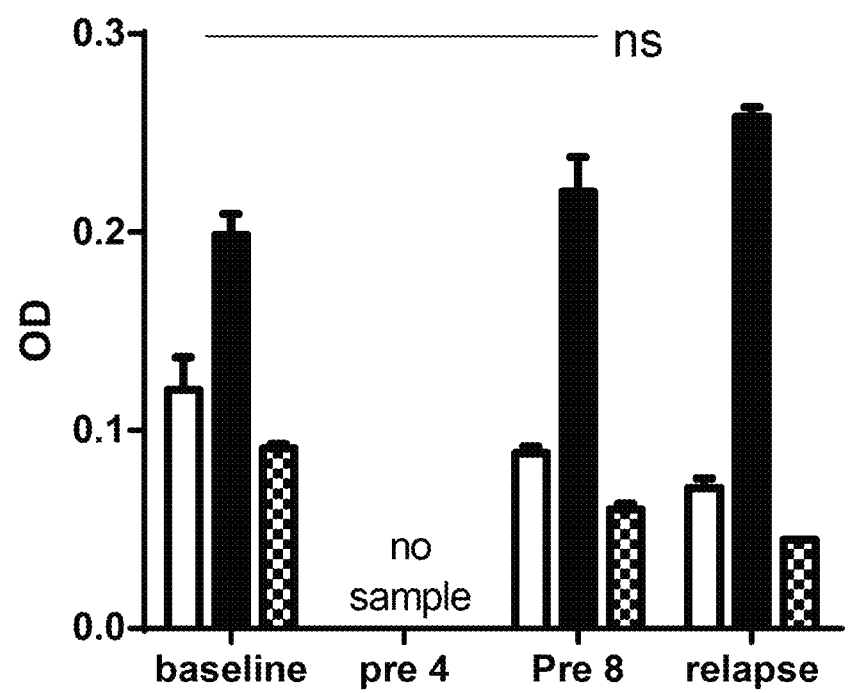
FIG. 16C shows the anti-viral response measured through CMV, EBV and influenza virus specific (CEF) IFN-γ production in PBMCs from DARZALEX™ (daratumumab) treated patient with PD at baseline and at indicated times during treatment. OD: optical density. White bar: negative control; black bar: CEF added; dashed bar: allogeneic PBMCs only. Ns: not significant. Pre 4, 8=Week 4 or 8 of treatment.
Figure 16D:
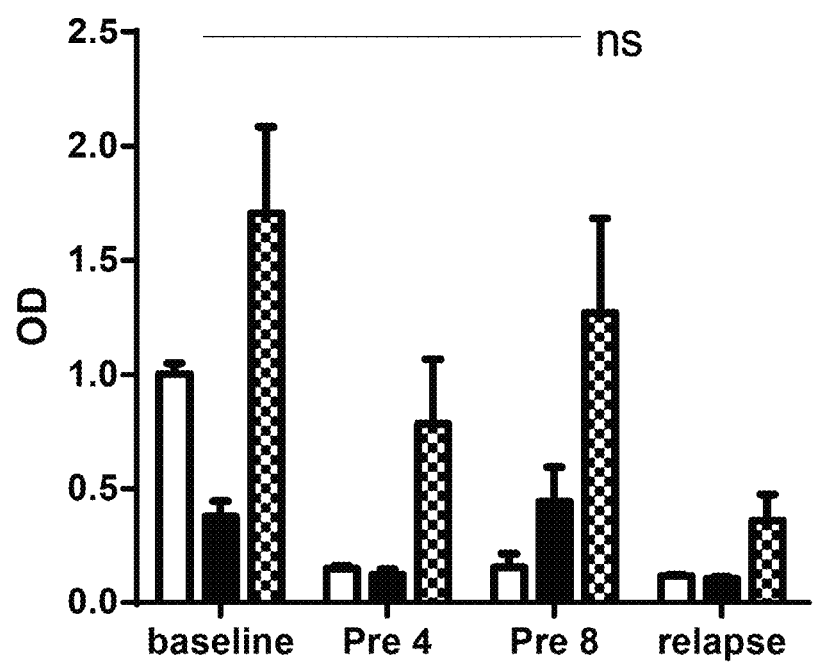
FIG. 16D shows the anti-viral response measured through CMV, EBV and influenza virus specific (CEF) IFN-γ production in PBMCs from DARZALEX™ (daratumumab) treated patient with MR at baseline and at indicated times during treatment. OD: optical density. White bar: negative control; black bar: CEF added; dashed bar: allogeneic PBMCs only. Ns: not significant. Pre 4, 8=Week 4 or 8 of treatment.
Figure 16F:
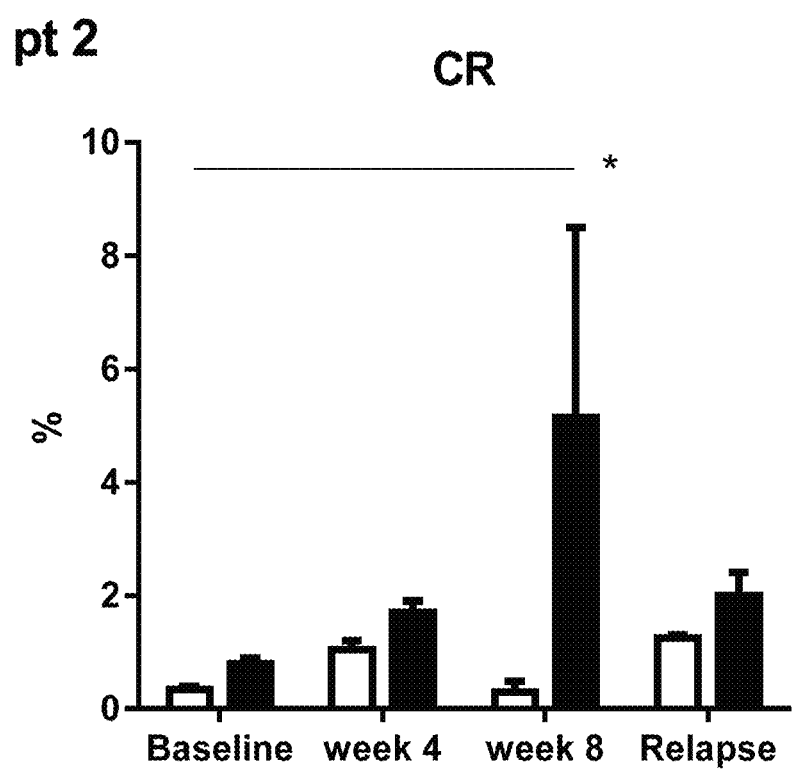
FIG. 16F shows the percentage (%) of proliferating virus-reactive T cells in PBMCs from DARZALEX™ (daratumumab) treated patient with CR at baseline and at indicated times during treatment. White bar: negative control; black bar: CEF added. Asterix indicates a statistically significant change. Pre 4, 8, 10=Week 4, 8 or 10 of treatment.

To further assess the effect of DARZALEX™ (daratumumab) on T-cell activation and functionality, IFN-γ production from peripheral T cells in response to viral and alloantigens was measured in DARZALEX™ (daratumumab)-treated patients (n=7) with a range of clinical outcomes. Patients with a PR or better demonstrated significant increases in IFN-γ secretion in response to viral and alloantigens following DARZALEX™ (daratumumab) treatment, compared with baseline, for at least one time point during treatment, suggesting that T cell function is not impaired by low CD38 expression (see Example 6, FIG. 9C). Similar to the TCR clonality data, this increase was more marked in patients who responded to DARZALEX™ (daratumumab) than those who did not. FIG. 16A shows the anti-viral response of one representative patient with VGPR. FIG. 16B shows the anti-viral response of one representative patient with CR. FIG. 16C shows the anti-viral response of one representative patient with PD. FIG. 16D shows the anti-viral response of one representative patient with MR. In the Figures, error bars represent standard error of the mean of duplicate cultures. Asterisk denotes statistically significant changes between the indicated comparisons. Best response per Independent Review Committee is shown. Consistent with these results, virus-reactive T-cells in patients with VGPR (FIG. 16E) or CR (FIG. 16F) demonstrated an increase in proliferative capacity during DARZALEX™ (daratumumab) treatment.

Example 9. Mechanism of Sensitivity of CD38 Expressing Immune Cell Subtypes to DARZALEX™ (Daratumumab)

Data from both GEN501 and SIRIUS studies indicated that some immune cells that express CD38 are depleted (NK cells, regulatory T-cells (Tregs), regulatory B-cells (Bregs), and myeloid derived suppressor cells (MDSCs)), while others that express CD38 increase in number (cytotoxic and helper T cells) with DARZALEX™ (daratumumab) therapy.

Figure 17A:
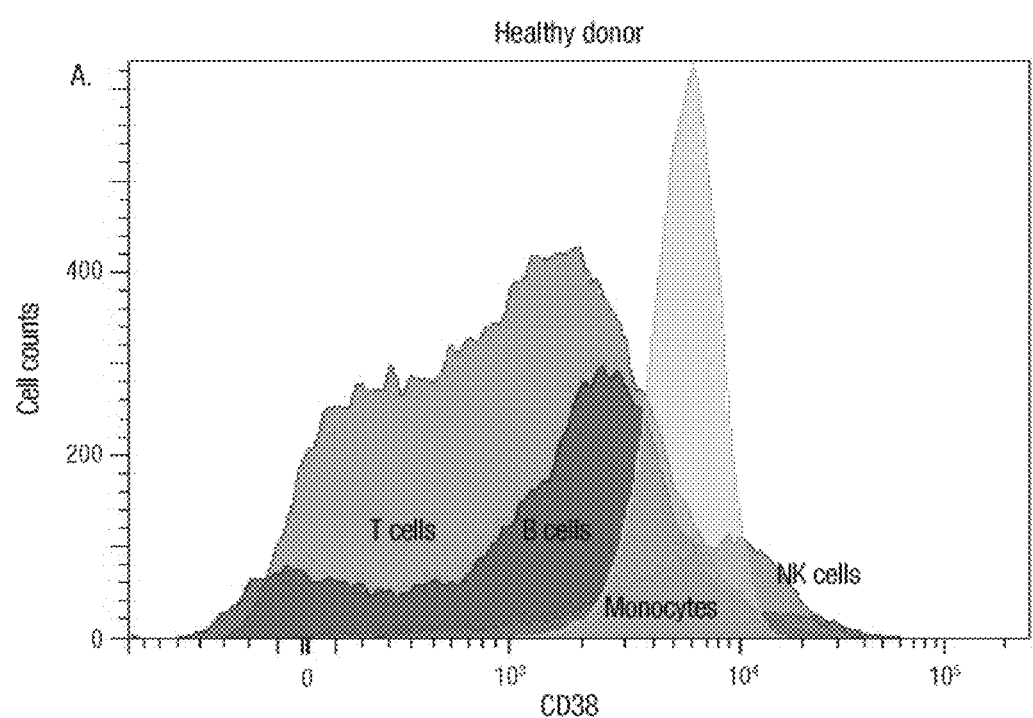
FIG. 17A shows a histogram of FACS analyses showing CD38 expression levels on natural killer cells (NK), monocytes, B cells and T cells from a healthy donor.
Figure 17B:
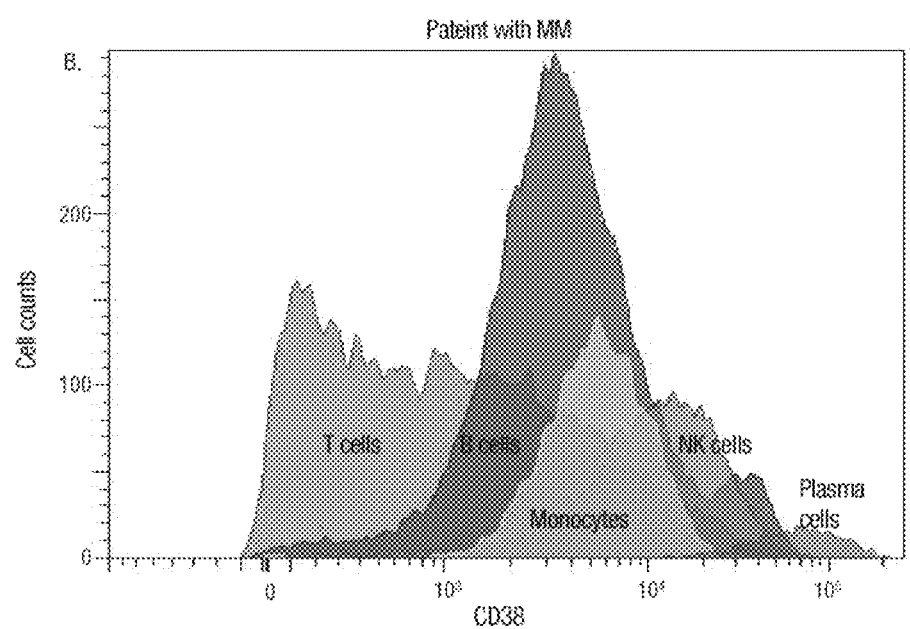
FIG. 17B shows a histogram of FACS analyses showing CD38 expression levels on plasma cells, natural killer cells (NK), monocytes, B cells and T cells from a multiple myeloma patient.
Figure 17C:
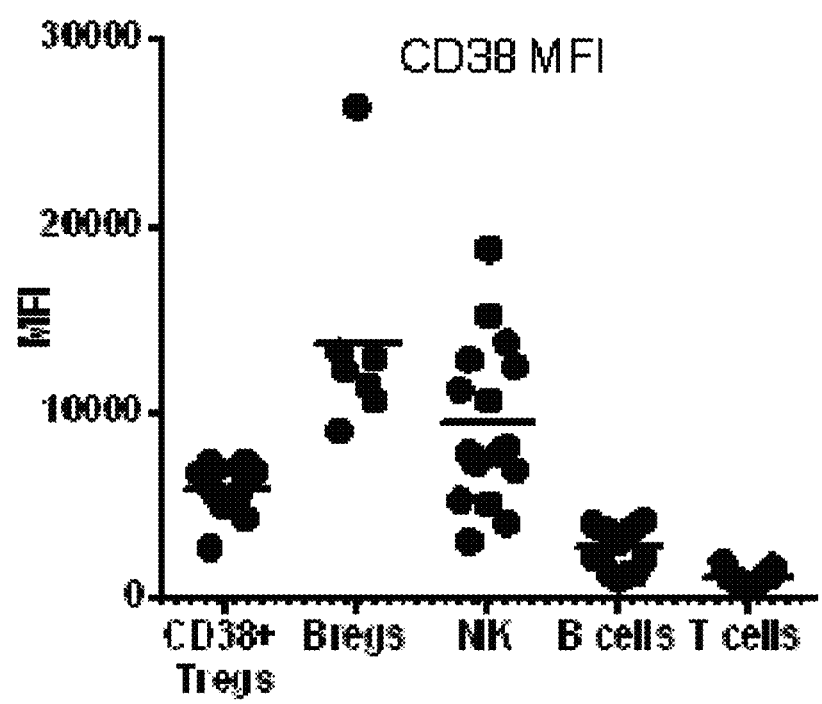
FIG. 17C shows a comparison of the mean fluorescent intensity (MFI) of CD38 in CD38+ Tregs, Bregs, NK, B cells and T cells from relapsed and refractory multiple myeloma patients. CD38 was expressed at lower level in B cells and T cells when compared to the CD38+ Tregs, Bregs and NK cells.

To address the mechanism of sensitivity, expression levels of CD38 were assessed in various subpopulations of immune cells in healthy donors and in multiple myeloma patients enrolled in either GEN501 or SIRIUS study. FIG. 17A shows a histogram of expression of CD38 in immune cells from a healthy donor, and FIG. 17B shows a histogram of expression of CD38 in immune cells from a multiple myeloma patient. In a healthy donor, CD38 expression was highest on NK cells, followed by monocytes, B and T cells. In a multiple myeloma patient, CD38 expression was highest on plasma cells, followed by a subset of B cells, NK cells, monocytes, B-cells and T-cells. FIG. 17C shows a comparison of the mean fluorescent intensity (MFI) of CD38 across NK cells, Tregs, Bregs, B- and T-cells cells from relapsed and refractory myeloma patients, demonstrating that after plasma cells, NK cells expressed the highest levels of CD38, followed by regulatory T-cells (Tregs) and regulatory B-cells (Bregs).

In addition to CD38 expression, other cell surface proteins such as complement inhibitory proteins (CIPs; CD46, CD55, CD59) may contribute to sensitivity or resistance to DARZALEX™ (daratumumab). In vitro evaluation of CIPs across immune cell subpopulations found that NK cells express very low levels of CD59 and CD55, while other T and B cell populations express much higher levels. This could also contribute to the variability of DARZALEX™ (daratumumab) sensitivity across immune cell subtypes (data not shown).

Discussion

This study describes previously unknown immunomodulatory effects of DARZALEX™ (daratumumab) through reduction of CD38$^+$ immune suppressive cellular populations and concomitant induction of helper and cytotoxic T-cell expansion, production of IFN-γ in response to viral peptides, and increased TCR clonality, indicating an improved adaptive immune response.

This study demonstrates that MDSCs and Bregs express CD38 and were susceptible to DARZALEX™ (daratumumab) treatment. These cells are known to be present in the tumor microenvironment and contribute to tumor growth, immune evasion, angiogenesis, metastasis, and production of suppressive cytokines. In addition to these CD38$^+$ suppressive cellular subsets, a novel subpopulation of regulatory T cells (CD4$^+$CD25$^+$CD 127$^{dim}$) was identified that also expressed high levels of CD38 and demonstrated superior autologous T-cell suppressive capacities. These cells were also sensitive to DARZALEX™ (daratumumab) and were significantly reduced in patients receiving treatment. DARZALEX™ (daratumumab)-mediated elimination of these CD38$^+$ immune-regulatory cells may reduce local immune suppression within the myeloma microenvironment and allow positive immune effector cells to expand and contribute to antitumor response.

Indeed, significant increases in broad T-cells populations, including both CD4$^+$ and CD8$^+$, were observed in both peripheral blood and within bone marrow (i.e., the tumor). Specific CD8$^+$ subpopulations were altered with DARZALEX™ (daratumumab) therapy, including significant decreases in naive T-cells and concomitant significant increases in effector memory CD8$^+$ T-cells, indicating a shift in effector T-cells towards an antigenic experienced phenotype that retained immunological memory and may be reactive against tumor antigens. Ratios of CD8$^+$:CD4$^+$ and CD8$^+$:Tregs also increased significantly with treatment, demonstrating a shift in positive versus negative immune regulators.

To evaluate whether expanded CD4$^+$ and CD8$^+$ T-cells were clonal in nature, the T-cell repertoire was examined in a subset of patients. T-cell clonality significantly increased with DARZALEX™ (daratumumab) treatment, even in patients who had a best response of SD or who progressed. Therefore, increased T-cell clonality cannot be due simply to reduction in tumor burden. However, the skew in T-cell clonality was greater in patients with a good clinical response, and was correlated with the increase in CD8$^+$ T-cells, suggesting the observed T-cell expansion with DARZALEX™ (daratumumab) treatment was antigen-driven. This is remarkable in this patient population, which was heavily pretreated (median of 5 prior lines of therapy) and not expected to be able to mount a strong antitumor immune response. In addition to increased TCR clonality, patients with a response to DARZALEX™ (daratumumab) demonstrated increased T-cell responses to preexisting viral- and alloantigens, suggesting the rescue of the immune system from an immunosuppressive state.

Treatment with DARZALEX™ (daratumumab) caused a reduction in immune suppressive MDSC and regulatory T- and B-cells. These reductions were concomitant with an expansion of CD4$^+$ T-helper cells and CD8$^+$ cytotoxic T-cells. T-cell clonality and functional anti-viral responses as measured by IFN-γ production also increased with DARZALEX™ (daratumumab) treatment. These observations indicate that T-cells continued to function properly, despite low CD38 expression, and suggest that increased T-cell response may be due to depletion of regulatory cells. Further, these changes in T-cell expansion, activity, and clonality were more pronounced in patients who responded to DARZALEX™ (daratumumab) compared with those who did not. Relapse from DARZALEX™ (daratumumab) therapy was associated with reversal of many of these changes. This suggests an additional, previously-uncharacterized mechanism of action of DARZALEX™ (daratumumab) through immunomodulation that may contribute to clinical responses and its efficacy.

Recently, antibodies that promote antitumor immune responses, rather than targeting the cancer directly, have demonstrated efficacy in a range of settings. Antibodies inhibiting CTLA-4 and PD-1 promote T-cell expansion and enhance T-cell activation, resulting in prolonged survival and delayed disease recurrence in patients with advanced solid tumors and hematologic malignancies such as Hodgkin lymphoma. By enhancing anticancer immunity, these immunomodulatory antibodies may not only induce clinical responses, but also prevent disease recurrence.

Example 10. Serum Proteomic Analysis of Multiple Myeloma Subjects Traded with Single-Agent DARZALEX™ (Daratumumab) in 54767414MMY2002 (SIRIUS) Part 2 Clinical Study Biomarker Sample Collection and Processing Peripheral blood samples were collected in standard serum separator tubes (2.5 mL to 5 mL) and serum aliquots were shipped frozen SomaLogic, Inc (Boulder, Colo.) for multianalyte serum protein profiling.

The serum protein profiling was performed at SomaLogic using a pre-validated SOMAscan assay that measures 1129 protein analytes by use of SOMAmer affinity based molecules. SOMAmer reagents are single stranded DNA-based protein affinity reagents. The assay uses small amounts of input sample (150 μL plasma) and converts the protein signal to a SOMAmer signal that is quantified by custom DNA microarray. Each SOMAmer contains 4 functional moieties:
1. A unique protein recognition sequence
2. Biotin for capture
3. Photocleavable linker
4. Fluorescent molecule for detection The unique protein recognition sequence uses DNA and incorporates chemically modified nucleotides that mimic amino acid side chains, expanding the diversity of standard aptamers and enhancing the specificity and affinity of protein-nucleic acid interactions (Gold et al., PLoS One 5:e15004, 2010). The aptamers are selected for by SELEX. SOMAmer reagents are selected using proteins in their native conformations. As such SOMAmer reagents require an intact, tertiary protein structures for binding. Unfolded or denatured presumably inactive proteins are not detected by SOMAmer reagents.

Master mixes of SOMAmer reagents are grouped for sample type and dilution. The reagents are pre-bound to streptavidin beads prior to sample incubation. Proteins in the samples are bound to the cognate SOMAmers during equilibrium, washed, incubated with NHS-biotin, washed and then the beads are exposed to UV light to cleave the photocleavable linker. The elution contains the SOMAmer reagents bound to their biotin labeled proteins. A streptavidin capture and subsequent washes removes the unbound SOMAmer reagents. In the final elution the SOMAmer molecules are released from their cognate proteins through denaturing conditions. The final eluate is hybridized to custom Agilent DNA microarrays and the fluorophore from the SOMAmer molecules it quantified by relative fluorescent units (RFU). The RFU is proportional to the amount of protein in the sample.

Samples from the MMY2002 study were tested in two primary batches. A first batch of 180 samples contained paired Cycle 1 Day 1 (C1D1, baseline) and C3D1 (Cycle 3 Day 1) serum samples from 90 subjects. The 180 samples were analyzed together on 3 separate SomaScan plates. The second batch of samples includes 50 C1D1 samples, including 35 repeated samples from batch 1.

Data Analyses

Input Datasets and Definitions

Treated subjects with an evaluable response were included in the data analysis. Consistently throughout the report, responders are defined as subjects with an overall best response (per IRC, for MMY2002) of sCR, VGPR, and PR, stable disease (SD) subjects as a subject with minimal response (MR) or SD, and non-responders are defined as subjects with an overall best response (per IRC, for MMY2002) of progressive disease (PD).

Somalogic Data Pre-Processing

Batch Alignment

Batches 1 and 2 of MMY2002 samples were tested on two different versions of the SOMAscan platform. Differences between the two versions were minor, and included three SOMAmer sequences that changed between the versions (CTSE: 3594-6_1->3594-6_5, FCN1: 3613-62_1->3613-62_5, BMPER: 3654-27_1->3654-27_4). These were removed from the analysis.

The measurements of the three batch 1 plates were aligned according to SomaLogic's standard inter-plate calibration workflow, by defining plate-wide calibration scaling factors for each SOMAmer by calculating the ratio of a Master-mix specific global reference value to the median of 7 in-plate control calibrator measurements. The plate-specific scaling factor for each SOMAmer reagent was applied to each sample on the plate equivalently.

Given the different SOMAscan platform versions of batch 1 and 2, systematic inter-batch variability correction was done with a modified implementation of SomaLogic's standard inter-plate calibration workflow, by leveraging the repeated measurement of 35 samples across batches. For each SOMAmer the ratio of the batch 1 post-calibration measurement divided by the batch 2 pre-calibration measurement was calculated for each of the 35 repeated samples (r$_{i,j}$). The median of these 35 ratios was used to define the revised SOMAmer-specific calibration scaling factor for the batch 2 samples ($\tilde{r}_i$). These calibration scaling factors were then implemented identically to the standard SOMAscan procedure.

$$r_{i,j} = \left( \frac{\text{Post-}Calib.\ Conc_{Batch\,1,i,j}}{\text{Pre-}Calib.\ Conc_{Batch\,2,i,j}} \right),$$

$$\vec{r}_i = (r_{i,1}, r_{i,2}, \ldots, r_{i,j}) \text{ for all repeated samples } j$$

$$\text{Calibration Scaling } Factor_i = \text{median}(\vec{r}_i) = \tilde{r}_i$$

Once the revised calibration scaling factors were calculated, the distributions of all the scaling factors for each batch of the analysis were plotted to assess the presence of outliers. 9 SOMAmers with extremely large or small calibrators (>0.25 and <3) were removed from the analyses due to poor reproducibility.

After batch alignment and SOMAmer filtering was complete for MMY2002, a log 2 transformation was applied to all protein concentration values of MMY2002 to bring the data more in line with a normal distribution and to improve the performance of parametric statistical tests.

Confounding Variable Correction

Estimation of the portion of dataset variance explained by meta-variables (like demographics, response class, and sample time point) and identification of potential confounding factors was performed by principal component analysis on the centered and scaled dataset. Simple linear models were fit to identify the highest ranked PC that was significantly associated with each of the variables of interest. The significance of these associations was determined using a Wald test and the fraction of the PC variability explained by the model was estimated by the R2 of the fit. For the MMY2002 data, site ID was found to be correlated with PC1 and explained the largest portion of dataset variability (≥7.37%, p-value=3.71×10−9). In order reduce the impact of sample acquisition site related effects within the data, ComBat28 was utilized to correct for site ID effects.

Repeated Sample Merging

The data of the 35 samples repeated between MMY2002 batches 1 and 2 was merged by calculating the mean for each protein.

Differential Protein Concentration Analysis

Responders Versus Non-Responders

Statistical comparison of protein concentration distributions in DARZALEX™ (daratumumab) responders versus non-responders was performed at both baseline and on treatment using two complementary methods (i) Wilcoxon rank-sum test (Hollander and Wolfe, Ninparametirc Statistical Methods. New York: John Wiley & Sons. 1973. 27-33 (one-sample), 68-75 (two-sample) on each individual SOMAmer and (ii) Limma analysis (Ritchie, M. E., et al., Nucleic Acids Res. 2015; 20:43(7):e47) on all SOMAmers simultaneously. All p-values were adjusted using the Benjamini-Hochberg (BH) method for multiple hypothesis correction (Benjamini and Hochberg, (1995) *J. R. Statist. Soc.* B.57: 289-300; R: A Language and Environment for Statistical Computing, R Development Core Team, R Foundation for Statistical Computing, Vienna, Austria. 2011; ISBN 3-900051-07-0). The null hypothesis of no differential expression was rejected when the adjusted p-value <0.05.

On Treatment Versus Baseline

Baseline versus on treatment protein levels were compared using three alternative statistical methods: (i) two-way repeated-measures ANOVA6 (ii) the Wilcoxon signed-rank test and (iii) the Friedman test (Johnson et al., (2007) *Biostatistics* 8(1):118-127). All p-values were adjusted to control FDR using the BH method for multiple hypothesis correction (Benjamini and Hochberg, J. R. Statist. Soc. B.57:289-300, 1995). In addition to the treatment significance, the two-way repeated-measures ANOVA (Chambers et al., Analysis of variance; designed experiments: Chapter 5. Statistical Models in S, Editors J. M Chambers and T. J Hastie. Wadsworth & Brookes/Cole. 1992) was also applied to determine if significant time-point:response-class interaction occurred for each SOMAmer. A modified Wilcoxon rank-sum test was applied as a post-hoc test to specifically determine if responders and non-responders showed different treatment effects, by calculating the difference between every subject's on treatment and baseline protein concentration values and performing a Wilcoxon rank-sum test. Significance values were adjusted using the BH method and the null hypothesis was rejected when the adjusted p-value <0.05.

Classifier Training

Baseline protein level MMY2002 data was used to build a response prediction classifier. A nested-loop stratified 10-fold cross-validation approach repeated 30 times, using 4 different machine learners: Support Vector Machines (SVM), Random Forests (RF), Naïve Bayes (NB), and j48 decision trees. For each learner, the training procedure began with creating 10 balanced folds of the dataset (outer loop). One of these folds was held out as a test cohort while the remaining 9 were passed to an inner loop as the training cohort. Within the inner loop, the training cohort was once again split into 10 balanced folds, creating inner-training and inner-test sets. Learners were trained on each of these inner-training sets and this process was repeated 30 times for each cohort within the outer loop. The accuracy of each inner loop learner at predicting the inner-test sets was used to select features and optimize model parameters. Once the 30× inner looping was complete for each training cohort, the performance of the outer loop (using the optimized parameters and features) was assessed on each corresponding test cohort. The entire outer looping procedure was then repeated 30 times, producing 30 response predictions for every sample within the dataset. The AUC, Sensitivity, and Specificity statistics obtained from this looping approach were an approximation of how well the final model, trained on the full original dataset, will perform on new test cases.

Results from MMY2002 Study

Figure 18:
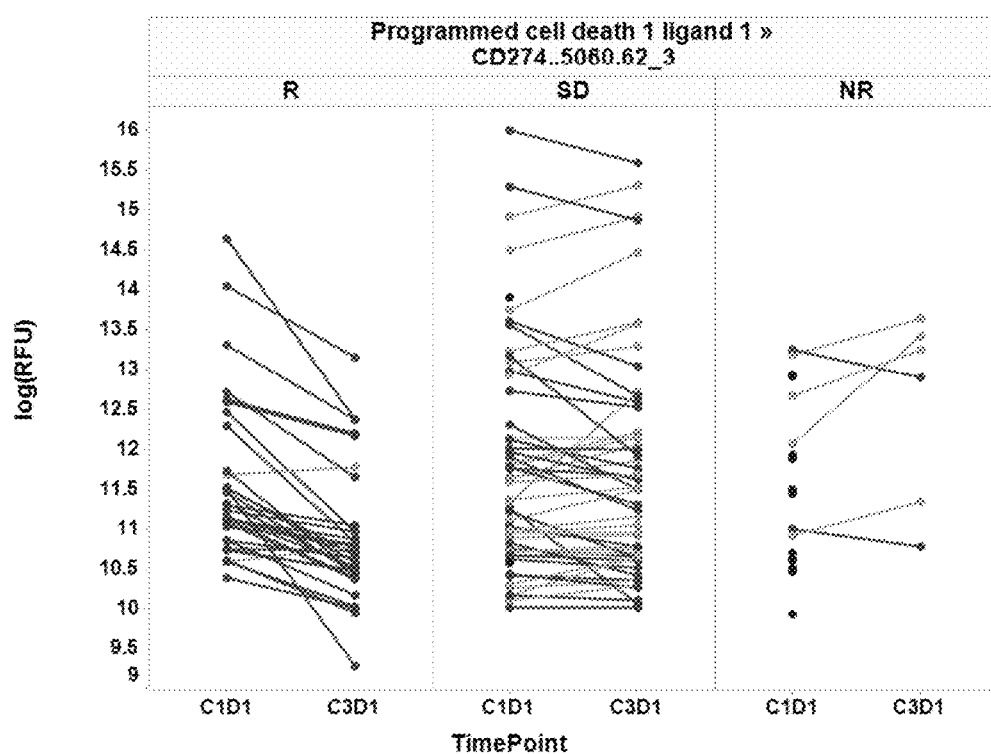
FIG. 18 shows that PD-L1 protein is downregulated in PBMC samples from responders (R) and upregulated in non-responders (NR) over time. SD: stable disease. C1D1: cycle 1 day 1; C3D1, cycle 3, day 1. Y axis shows the log 2 protein concentration values.

Various comparisons were conducted including treatment induced response dependent changes in protein expression. One of the proteins that showed decreased expression in responders over time was PD-L1, whereas PD-L1 protein expression increased in non-responders over time. The engagement of PD-L1 on T cells leads to reduced T cell function and increased Treg development. FIG. 18 shows protein expression profile of PD-L1 in responders, non-responders and in patients with stable disease at cycle 1 and cycle 3.

PD-L1 engagement with its receptor PD-1 suppresses anti-tumor responses and drives T cell anergy and exhaustion. While not wishing to be bound by any particular theory, downregulation of PD-L1 upon anti-CD38 treatment may also result in improved potentiation of anti-tumor immune responses in solid tumors.

Example 11

Daratumumab in Combination with Lenalidomide Plus Dexamethasone Induces Clonality Increase and T-Cell Expansion: Results from a Phase 3 Randomized Study (POLLUX)

To further explore the ability of daratumumab to promote adaptive T-cell responses, T-cell repertoires (TCR) were profiled to evaluate T-cell clonality, expansion, and diversity from samples collected in POLLUX (MMY3003), a phase 3, randomized, open-label, multicenter study for patients with relapsed/refractory MM, in which daratumumab was tested in combination with lenalidomide plus dexamethasone versus lenalidomide plus dexamethasone alone (DRd vs. Rd; Dimopoulos M A et al, N Engl J Med. 2016 Oct. 6; 375(14):1319-1331). ClinicalTrial number NCT02076009.

POLLUX Trial Treatments

Patients were randomly assigned in a 1:1 ratio to receive daratumumab, lenalinomide and dexamehtasone (DRd) or lenalinomide and dexamethasone (Rd). Randomization was stratified by International Staging System (ISS), number of prior treatment programs (1 vs. 2 or 3 vs. >3), and prior lenalinomide treatment ("no" vs. "yes").

Daratumumab was administered as an IV infusion at a dose of 16 mg/kg weekly (on days 1, 8, 15, and 22) for 8 weeks during cycles 1 and 2, every 2 weeks (on days 1 and 15) for 16 weeks (cycles 3 through 6), and every 4 weeks thereafter. Both groups received lenalidomide at a dose of 25 mg orally on days 1 to 21 of each cycle if the creatinine clearance was more than 60 ml per minute (or a dose of 10 mg daily if the creatinine clearance was 30 to 60 ml per minute) and dexamethasone at a dose of 40 mg weekly. For the daratumumab group, the dose of dexamethasone was split: dexamethasone was administered at a dose of 20 mg before infusion as prophylaxis for infusion-related reactions and 20 mg was administered the next day.

Efficacy

At a median follow-up of 13.5 months, a total of 169 events of disease progression or death (in 53 patients [18.5%] in the daratumumab group vs. 116 [41.0%] in the control group) were reported. The hazard ratio for disease progression or death in the daratumumab group versus the control group was 0.37 (95% confidence interval [CI], 0.27 to 0.52; P<0.001 by stratified log-rank test). The Kaplan-Meier rate of progression-free survival at 12 months was 83.2% (95% CI, 78.3 to 87.2) in the daratumumab group and 60.1% (95% CI, 54.0 to 65.7) in the control group. The median progression-free survival was not reached (95% CI, could not be estimated) in the daratumumab group, as compared with 18.4 months (95% CI, 13.9 to could not be estimated) in the control group. Similarly, in the time-toevent analysis of disease progression, a total of 148 events (in 44 patients [15.4%] in the daratumumab group vs. 104 [36.7%] in the control group) were observed (hazard ratio, 0.34; 95% CI, 0.23 to 0.48; P<0.001). The rate of progression-free survival at 12 months was 85.7% (95% CI, 80.9 to 89.4) in the daratumumab group, as compared with 63.2% (95% CI, 57.1 to 68.8) in the control group.

Methods

T-cell receptor beta (TCRβ) sequencing for repertoire profiling was conducted on whole blood samples collected at baseline and eight weeks after daratumumab treatment (cycle 3 [C3]) from subjects on both arms using the ImmunoSEQ assay (Adaptive Biotechnologies. Seattle, Wash., USA). 133 subjects in DRd and 124 subjects in Rd treatment groups were included in this analysis and represented a balanced subgroup of the POLLUX clinical trial subjects. T-cell metric changes were compared between arms with ANOVA, including the treatment arm and visit interaction term. Within treatment-arm changes were evaluated with a Wilcoxon signed-rank test comparing baseline to on-treatment values per patient.

Results

Consistent with the randomized treatment groups, no baseline differences were observed in T-cell repertoire metrics between the treatment arms, including T-cell clonality, diversity (or richness), and T-cell fraction. Similar to prior findings from daratumumab monotherapy studies, significantly larger increase of TCRβ clonality was observed in the DRd arm (median of 0.166 at baseline to 0.263 at C3). Interestingly, there was no increase in TCRβ clonality in the Rd arm (median of 0.175 at baseline to 0.175 at C3). The change in TCRβ clonality between C1 (baseline) and C3 was significantly different between DRd and Rd (p=3.26E-10), demonstrating that the addition of daratumumab to Rd induces a specific clonal expansion of T cells. Estimated richness (diversity), on the other hand, slightly decreased with DRd treatment but not with Rd treatment (median of 503,951 at baseline to 427,096 at C3 [p=1.01E-04] vs 572,182 to 532,806 [p=3.58-01]). Among patients in both treatment groups, a bigger increase in T-cell fraction was observed in DRd vs Rd (median of 0.231 at baseline to 0.278 at C3 [p=2.62E-3] vs 0.228 to 0.249 [p=1.91E-01]). Although there were no significant differences in baseline characteristics in T-cell clonality, richness, and T-cell fraction, quartile analysis demonstrated that high baseline TCR richness predicted for better PFS with DRd but not for Rd.

Conclusion

Daratumumab in combination with lenalidomide plus dexamethasone specifically induced robust increases in T-cell clonality, which was not observed within the control lenalidomide plus dexamethasone arm. Interestingly, baseline TCR richness was associated with improved PFS in DRd subjects. This observation is similar to results with immune checkpoint inhibitors (Postow M A et al, J Immunother Cancer 2015; 3:23), and together with the significant increase in T-cell clonality, provides further evidence for the immunomodulatory activity of daratumumab, even in combination therapy. These data support daratumumab's immune-modulatory MOA and provide additional insights into daratumumab's effect on the TCR in combination with standard of care treatment.

Example 12. High-Parameter Mass Cytometry (CyTOF) Evaluation of Relapsed/Refractory Multiple Myeloma (MM) Patients Treated with Daratumumab Supports Immune Modulation as a Novel Mechanism of Action Next-generation mass cytometry (CyTOF), which allows high parameter evaluation of the immune system, was used to assess the effects of daratumumab alone or in combination on a more comprehensive profile of immune cell subpopulations.

Methods

Relapsed/refractory MM patient samples from a subset of single agent studies; SIRIUS (32 patients; whole blood [WB] only) and GEN501 (5 patients; WB and bone marrow [BM]) along with GEN503, a study of daratumumab plus lenalidomide and dexamethasone (9 pts; WB and BM) were analyzed. Fluorochrome or metal-conjugated antibody panel stained samples were evaluated by flow cytometry or cytometry by time-of-flight (CyTOF®) platforms, respectively. FACS analyses were performed and analyzed by FACS Canto II flow cytometers and FACSDiva software. For CyTOF analysis, events were clustered by phenotype by a spanning tree progression of density normalized events (SPADE) algorithm, and each cluster was associated with an immune population via Cytobank® software. Differential analysis of population fractions and marker intensity, over time and between response groups, derived raw P values from t-tests and single cell level bootstrap adjusted P values corrected for multiple dependent hypothesis testing. Results were visualized using SPADE trees and Radviz projections, a new method that allows for the comparison of populations and conditions while preserving the relation to original dimensions.

Results

Flow cytometry and high-dimensional CyTOF analyses confirmed previous findings including higher CD38 expression on plasma cells compared with other immune populations of natural killer (NK), monocytes, B and T cells, and depletion of both plasma cells and NK cells upon daratumumab treatment. Interestingly, while NK cells were significantly reduced with DARA treatment, remaining active NK cells (CD $16^+$CD$56^{dim}$) demonstrated increased expression of activation markers CD69, CD25 and CD137 while also decreasing granzyme B and increasing naive marker CD27. Though functionality tests weren't performed, the ability to evaluate several markers simultaneously suggests these cells possess limited cytotoxicity. Additionally, these studies indicated depletion of CD38 positive immune suppressive subsets of Tregs and Bregs. CD38$^+$ basophil reductions occurred independent of response and may provide insight to short-lived infusion related reactions. Several observations within the T-cell compartment were indicative of a DARA-mediated adaptive response in both WB and BM samples. T cells displayed increases in total numbers and shifted towards higher CD8:CD4 and effector:naïve ratios after 2 months of DARA treatment. Responders had higher expression levels of several activation markers including CD69 and HLA-DR along with increased production of cytolytic enzyme granzyme B in CD8$^+$ T cells following DARA treatment. Interestingly, in the GEN503 sample set, patients who achieved a complete response presented with a distinct BM CD4 T-cell phenotype of high granzyme B positivity versus those that achieved a partial response or very good partial response. This observation suggests patients with an active immune phenotype may achieve deeper responses to daratumumab in combination with standard of care agents lenalidomide and dexamethasone.

CONCLUSION

CyTOF analysis of patient samples from both single agent and combination daratumumab studies agree with flow cytometry and support the pharmacodynamics and immune modulatory mechanism of action of daratumumab while providing additional insight into changes in T-cell subtypes and activation status.

We claim:

1. A method of treating a patient having a solid tumor, comprising administering to the patient in need thereof a therapeutically effective amount of an antibody that specifically binds CD38 for a time sufficient to treat the solid tumor, wherein the solid tumor lacks detectable CD38 expression, and wherein the antibody comprises a heavy chain complementarity determining region (HCDR) 1, a HCDR2, a HCDR3 amino acid sequences of SEQ ID NOs: 6, 7 and 8, respectively, and a light chain complementarity determining region (LCDR) 1, a LCDR2 and a LCDR3 amino acid sequences of SEQ ID NOs: 9, 10 and 11, respectively.

2. The method of claim 1, wherein the solid tumor is a melanoma, a lung cancer, a squamous non-small cell lung cancer (NSCLC), a non-squamous NSCLC, a colorectal cancer, a prostate cancer, a castration-resistant prostate cancer, a stomach cancer, an ovarian cancer, a gastric cancer, a liver cancer, a pancreatic cancer, a thyroid cancer, a squamous cell carcinoma of the head and neck, a carcinoma of the esophagus or gastrointestinal tract, a breast cancer, a fallopian tube cancer, a brain cancer, an urethral cancer, a genitourinary cancer, a cervical cancer or a metastatic lesion of the cancer.

3. The method of claim 1, wherein the antibody that specifically binds CD38 comprises a heavy chain variable region (VH) amino acid sequence of SEQ ID NO: 4 and a light chain variable region (VL) amino acid sequence of SEQ ID NO: 5.

4. The method of claim 1, wherein the antibody that specifically binds CD38 is administered in combination with a second therapeutic agent.

5. The method of claim 4, wherein the second therapeutic agent is
 a) a chemotherapeutic agent, a targeted anti-cancer therapy, a standard of care drug for treatment of solid tumor, or an immune checkpoint inhibitor;
 b) an anti-PD-1 antibody;
 c) an anti-PD-1 antibody comprising
  i) the heavy chain variable region (VH) of SEQ ID NO: 22 and the light chain variable region (VL) of SEQ ID NO: 23;
  ii) the VH of SEQ ID NO: 24 and the VL of SEQ ID NO: 25;
  iii) the VH of SEQ ID NO: 32 and the VL of SEQ ID NO: 33; or
  iv) the VH of SEQ ID NO: 34 and the VL of SEQ ID NO:35;
 d) an anti-PD-L1 antibody;
 e) an anti-PD-L1 antibody comprising
  i) the VH of SEQ ID NO: 26 and the VL of SEQ ID NO: 27;
  ii) the VH of SEQ ID NO: 28 and the VL of SEQ ID NO: 29; or
  iii) the VH of SEQ ID NO: 30 and the VL of SEQ ID NO: 31;
 f) an anti-PD-L2 antibody;
 g) an anti-LAG3 antibody;
 h) an anti-TIM-3 antibody;
 i) an anti-TIM-3 antibody comprising
  i) the VH of SEQ ID NO: 36 and the VL of SEQ ID NO: 37; or
  ii) the VH of SEQ ID NO: 38 and the VL of SEQ ID NO: 39;
 j) an anti-CTLA-4 antibody;
 k) radiation therapy; or
 l) surgery.

6. The method of claim 4, wherein the antibody that specifically binds CD38 and the second therapeutic agent are administered simultaneously.

7. The method of claim 1, wherein the antibody that specifically binds CD38 is administered subcutaneously in a pharmaceutical composition comprising the antibody that specifically binds CD38 and a hyaluronidase.

8. The method of claim 1, wherein the antibody that specifically binds CD38 is administered intravenously in a pharmaceutical composition.

9. The method of claim 4, wherein the antibody that specifically binds CD38 and the second therapeutic agent are administered sequentially or separately.

10. The method of claim 1, wherein the antibody that specifically binds CD38 elicits an immune response in the patient that is an effector T cell (Teff) response mediated by $CD8^+$ T cells.

11. The method of claim 1, wherein the antibody that specifically binds CD38 increases the number of $CD8^+$ T cells, increases $CD8^+$ T cell proliferation, increases T cell clonal expansion, increases $CD8^+$ memory cell formation, increases antigen-dependent antibody production, increases cytokine production, increases chemokine production or increases interleukin production.

12. The method of claim 1, wherein the antibody that specifically binds CD38
 a) inhibits function of a regulatory T cell (Treg);
 b) inhibits function of a $CD3^+CD4^+CD25^+CD127^{dim}$ Treg;
 c) inhibits function of a $CD38^+$ Treg; or
 d) kills the Treg by antibody-dependent cell cytotoxicity (ADCC).

13. The method of claim 1, wherein the antibody that specifically binds CD38
 a) inhibits function of a myeloid-derived suppressor cell (MDSC);
 b) inhibits function of a $CD11b^+HLADR^-CD14^-CD33^+CD15^+$ MDSC;
 c) inhibits function of a $CD38^+$ MDSC; or
 d) kills the MDSC by ADCC.

14. The method of claim 1, wherein the antibody that specifically binds CD38
 a) inhibits function of a regulatory B cell (Breg);
 b) inhibits function of a $CD19^+CD24^+CD38^+$ Breg; or
 c) kills the Breg by ADCC.

15. A method of suppressing activity of an immune suppressor cell in a patient having a solid tumor that lacks detectable CD38 expression, comprising administering to the patient a therapeutically effective amount of an antibody that specifically binds CD38, wherein the antibody comprises a heavy chain complementarity determining region (HCDR) 1, a HCDR2, a HCDR3 amino acid sequences of SEQ ID NOs: 6, 7 and 8, respectively, and a light chain complementarity determining region (LCDR) 1, a LCDR2 and a LCDR3 amino acid sequences of SEQ ID NOs: 9, 10 and 11, respectively.

16. The method of claim 15, wherein
 a) the immune suppressor cell is a regulatory T cell (Treg);
 b) the immune suppressor cell is a $CD3^+CD4^+CD25^+CD127^{dim}$ Treg;
 c) the immune suppressor cell is a myeloid-derived suppressor cell (MDSC);
 d) the immune suppressor cell is a $CD11b^+HLADR^-CD14^-CD33^+CD15^+$ MDSC;
 e) the immune suppressor cell is a regulatory B cell (Breg); or
 f) the immune suppressor cell is a $CD19^+CD24^+CD38^+$ Breg.

17. The method of claim 16, wherein the antibody that specifically binds CD38 comprises a heavy chain variable region (VH) amino acid sequence of SEQ ID NO: 4 and a light chain variable region (VL) amino acid sequence of SEQ ID NO: 5.

18. A method of enhancing an immune response in a patient having a solid tumor that lacks detectable CD38 expression, comprising administering to the patient an antibody that specifically binds CD38, wherein the antibody comprises a heavy chain complementarity determining region (HCDR) 1, a HCDR2, a HCDR3 amino acid sequences of SEQ ID NOs: 6, 7 and 8, respectively, and a light chain complementarity determining region (LCDR) 1, a LCDR2 and a LCDR3 amino acid sequences of SEQ ID NOs: 9, 10 and 11, respectively.

19. The method of claim 18, wherein the antibody that specifically binds CD38 comprises a heavy chain variable region (VH) amino acid sequence of SEQ ID NO: 4 and a light chain variable region (VL) amino acid sequence of SEQ ID NO: 5.

* * * * *

SEQUENCE LISTING

<160> NUMBER OF SEQ ID NOS: 40

<210> SEQ ID NO 1
<211> LENGTH: 300
<212> TYPE: PRT

<213> ORGANISM: Homo sapiens

<400> SEQUENCE: 1

```
Met Ala Asn Cys Glu Phe Ser Pro Val Ser Gly Asp Lys Pro Cys Cys
1               5                   10                  15
Arg Leu Ser Arg Arg Ala Gln Leu Cys Leu Gly Val Ser Ile Leu Val
            20                  25                  30
Leu Ile Leu Val Val Val Leu Ala Val Val Pro Arg Trp Arg Gln
        35                  40                  45
Gln Trp Ser Gly Pro Gly Thr Thr Lys Arg Phe Pro Glu Thr Val Leu
    50                  55                  60
Ala Arg Cys Val Lys Tyr Thr Glu Ile His Pro Glu Met Arg His Val
65                  70                  75                  80
Asp Cys Gln Ser Val Trp Asp Ala Phe Lys Gly Ala Phe Ile Ser Lys
                85                  90                  95
His Pro Cys Asn Ile Thr Glu Glu Asp Tyr Gln Pro Leu Met Lys Leu
            100                 105                 110
Gly Thr Gln Thr Val Pro Cys Asn Lys Ile Leu Leu Trp Ser Arg Ile
        115                 120                 125
Lys Asp Leu Ala His Gln Phe Thr Gln Val Gln Arg Asp Met Phe Thr
130                 135                 140
Leu Glu Asp Thr Leu Leu Gly Tyr Leu Ala Asp Asp Leu Thr Trp Cys
145                 150                 155                 160
Gly Glu Phe Asn Thr Ser Lys Ile Asn Tyr Gln Ser Cys Pro Asp Trp
                165                 170                 175
Arg Lys Asp Cys Ser Asn Asn Pro Val Ser Val Phe Trp Lys Thr Val
            180                 185                 190
Ser Arg Arg Phe Ala Glu Ala Ala Cys Asp Val Val His Val Met Leu
        195                 200                 205
Asn Gly Ser Arg Ser Lys Ile Phe Asp Lys Asn Ser Thr Phe Gly Ser
210                 215                 220
Val Glu Val His Asn Leu Gln Pro Glu Lys Val Gln Thr Leu Glu Ala
225                 230                 235                 240
Trp Val Ile His Gly Gly Arg Glu Asp Ser Arg Asp Leu Cys Gln Asp
                245                 250                 255
Pro Thr Ile Lys Glu Leu Glu Ser Ile Ile Ser Lys Arg Asn Ile Gln
            260                 265                 270
Phe Ser Cys Lys Asn Ile Tyr Arg Pro Asp Lys Phe Leu Gln Cys Val
        275                 280                 285
Lys Asn Pro Glu Asp Ser Ser Cys Thr Ser Glu Ile
        290                 295                 300
```

<210> SEQ ID NO 2
<211> LENGTH: 14
<212> TYPE: PRT
<213> ORGANISM: Homo sapiens

<400> SEQUENCE: 2

```
Ser Lys Arg Asn Ile Gln Phe Ser Cys Lys Asn Ile Tyr Arg
1               5                   10
```

<210> SEQ ID NO 3
<211> LENGTH: 14
<212> TYPE: PRT
<213> ORGANISM: Homo sapiens

<400> SEQUENCE: 3

Glu Lys Val Gln Thr Leu Glu Ala Trp Val Ile His Gly Gly
1               5                   10

<210> SEQ ID NO 4
<211> LENGTH: 122
<212> TYPE: PRT
<213> ORGANISM: Artificial Sequence
<220> FEATURE:
<223> OTHER INFORMATION: VH of anti-CD38 antibody

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: VL of anti-CD38 antibody

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: HCDR1 of anti-CD38 antibody

<400> SEQUENCE: 6

```
Ser Phe Ala Met Ser
1               5

<210> SEQ ID NO 7
<211> LENGTH: 17
<212> TYPE: PRT
<213> ORGANISM: Artificial Sequence
<220> FEATURE:
<223> OTHER INFORMATION: HCDR2 of anti-CD38 antibody

<400> SEQUENCE: 7

Ala Ile Ser Gly Ser Gly Gly Thr Tyr Tyr Ala Asp Ser Val Lys
1               5                   10                  15

Gly

<210> SEQ ID NO 8
<211> LENGTH: 13
<212> TYPE: PRT
<213> ORGANISM: Artificial Sequence
<220> FEATURE:
<223> OTHER INFORMATION: HCDR3 of anti-CD38 antibody

<400> SEQUENCE: 8

Asp Lys Ile Leu Trp Phe Gly Glu Pro Val Phe Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: LCDR1 of anti-CD38 antibody

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: LCDR2 of anti-D38 antibody

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: LCDR3 of anti-CD38 antibody

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
<223> OTHER INFORMATION: Heavy chain of anti-CD38 antibody

<400> SEQUENCE: 12
```

-continued

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 13
<211> LENGTH: 214
<212> TYPE: PRT
<213> ORGANISM: Artificial Sequence
<220> FEATURE:
<223> OTHER INFORMATION: Light chain of anti-CD38 antibody

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 122
<212> TYPE: PRT
<213> ORGANISM: Artificial Sequence
<220> FEATURE:
<223> OTHER INFORMATION: VH of anti-CD38 antibody 003

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45
```

-continued

Gly Arg Val Ile Pro Phe Leu Gly Ile Ala Asn Ser Ala Gln Lys Phe
            50                  55                  60

Gln Gly Arg Val Thr Ile Thr Ala Asp Lys Ser Thr Ser Thr Ala Tyr
 65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser
            115                 120

<210> SEQ ID NO 15
<211> LENGTH: 107
<212> TYPE: PRT
<213> ORGANISM: Artificial Sequence
<220> FEATURE:
<223> OTHER INFORMATION: VL of anti-CD38 antibody 003

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Leu Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: VH of anti-CD38 antibody 024

<400> SEQUENCE: 16

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
    50                  55                  60

Gln Gly Gln Val Thr Phe Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser

<210> SEQ ID NO 17
<211> LENGTH: 107
<212> TYPE: PRT
<213> ORGANISM: Artificial Sequence
<220> FEATURE:
<223> OTHER INFORMATION: VL of anti-CD38 antibody 024

<400> SEQUENCE: 17

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Gly Leu Leu Ile
        35                  40                  45
Tyr Asp Ala Ser Asn Arg Ala Ser Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Leu
                85                  90                  95
Thr Phe Gly Gly Gly Thr Lys Val Glu Ile Lys
            100                 105
```

<210> SEQ ID NO 18
<211> LENGTH: 120
<212> TYPE: PRT
<213> ORGANISM: Artificial Sequence
<220> FEATURE:
<223> OTHER INFORMATION: VH of anti-CD38 antibody MOR202

<400> SEQUENCE: 18

```
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Tyr Met Asn Trp Val Arg Gln Ala Pro Gly Lys Gly Leu Glu Trp Val
        35                  40                  45
Ser Gly Ile Ser Gly Asp Pro Ser Asn Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Leu Pro Leu Val Tyr Thr Gly Phe Ala Tyr Trp Gly Gln
            100                 105                 110
Gly Thr Leu Val Thr Val Ser Ser
        115                 120
```

<210> SEQ ID NO 19
<211> LENGTH: 109
<212> TYPE: PRT
<213> ORGANISM: Artificial Sequence
<220> FEATURE:
<223> OTHER INFORMATION: VL of anti-CD38 antibody MOR202

<400> SEQUENCE: 19

```
Asp Ile Glu Leu Thr Gln Pro Pro Ser Val Ser Val Ala Pro Gly Gln
1               5                   10                  15
```

```
Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
            35                  40                  45

Gly Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105
```

<210> SEQ ID NO 20
<211> LENGTH: 120
<212> TYPE: PRT
<213> ORGANISM: Artificial Sequence
<220> FEATURE:
<223> OTHER INFORMATION: VH of anti-CD38 mAb isatuximab

<400> SEQUENCE: 20

```
Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
            115                 120
```

<210> SEQ ID NO 21
<211> LENGTH: 107
<212> TYPE: PRT
<213> ORGANISM: Artificial Sequence
<220> FEATURE:
<223> OTHER INFORMATION: VL of anti-CD38 mAb isatuximab

<400> SEQUENCE: 21

```
Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
            50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
```

```
                 85                  90                  95

Thr Phe Gly Gly Gly Thr Lys Leu Glu Ile Lys
            100                 105

<210> SEQ ID NO 22
<211> LENGTH: 120
<212> TYPE: PRT
<213> ORGANISM: Artificial Sequence
<220> FEATURE:
<223> OTHER INFORMATION: VH of anti-PD-1 mAb Keytruda

<400> SEQUENCE: 22

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 23
<211> LENGTH: 111
<212> TYPE: PRT
<213> ORGANISM: Artificial Sequence
<220> FEATURE:
<223> OTHER INFORMATION: VL of anti-PD-1 mAb Keytruda

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 24
<211> LENGTH: 113
<212> TYPE: PRT
<213> ORGANISM: Artificial Sequence
<220> FEATURE:
<223> OTHER INFORMATION: VH of anti-PD-1 mAb Opdivo

<400> SEQUENCE: 24
```

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 25
<211> LENGTH: 107
<212> TYPE: PRT
<213> ORGANISM: Artificial Sequence
<220> FEATURE:
<223> OTHER INFORMATION: VL of anti-PD-1 mAb Opdivo

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 26
<211> LENGTH: 121
<212> TYPE: PRT
<213> ORGANISM: Artificial Sequence
<220> FEATURE:
<223> OTHER INFORMATION: VH of anti-PD-L1 mAb durvalumab

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

-continued

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 27
<211> LENGTH: 108
<212> TYPE: PRT
<213> ORGANISM: Artificial Sequence
<220> FEATURE:
<223> OTHER INFORMATION: VL of anti-PD-L1 mAb durvalumab

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 28
<211> LENGTH: 118
<212> TYPE: PRT
<213> ORGANISM: Artificial Sequence
<220> FEATURE:
<223> OTHER INFORMATION: VH of anti-PD-L1 mAb atezolizumab

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 29
<211> LENGTH: 107
<212> TYPE: PRT

<213> ORGANISM: Artificial Sequence
<220> FEATURE:
<223> OTHER INFORMATION: VL of anti-PD-L1 mAb atezolizumab

<400> SEQUENCE: 29

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 30
<211> LENGTH: 120
<212> TYPE: PRT
<213> ORGANISM: Artificial Sequence
<220> FEATURE:
<223> OTHER INFORMATION: VH of anti-PD-L1 mAb avelumab

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

<210> SEQ ID NO 31
<211> LENGTH: 110
<212> TYPE: PRT
<213> ORGANISM: Artificial Sequence
<220> FEATURE:
<223> OTHER INFORMATION: VL of anti-PD-L1 mAb avelumab

<400> SEQUENCE: 31

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

```
Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Val Phe Gly Thr Gly Thr Lys Val Thr Val Leu
            100                 105                 110

<210> SEQ ID NO 32
<211> LENGTH: 123
<212> TYPE: PRT
<213> ORGANISM: Artificial Sequence
<220> FEATURE:
<223> OTHER INFORMATION: VH of anti-PD-1 mAb

<400> SEQUENCE: 32

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Asp Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser
        115                 120

<210> SEQ ID NO 33
<211> LENGTH: 107
<212> TYPE: PRT
<213> ORGANISM: Artificial Sequence
<220> FEATURE:
<223> OTHER INFORMATION: VL of anti-PD-1 mAb

<400> SEQUENCE: 33

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Tyr Trp Pro Leu
                 85                  90                  95

Thr Phe Gly Gln Gly Thr Lys Val Glu Ile Lys
            100                 105
```

```
<210> SEQ ID NO 34
<211> LENGTH: 117
<212> TYPE: PRT
<213> ORGANISM: Artificial Sequence
<220> FEATURE:
<223> OTHER INFORMATION: VH of anti-PD-1 mAb

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Asp Met Ser Trp Val Arg Gln Ala Pro Gly Lys Gly Leu Glu Ser Val
        35                  40                  45

Ala Tyr Ile Ser Gly Gly Ala Asn Thr Tyr Tyr Leu Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Leu Ser Tyr Phe Asp Val Trp Gly Gln Gly Thr Leu
            100                 105                 110

Val Thr Val Ser Ser
        115

<210> SEQ ID NO 35
<211> LENGTH: 107
<212> TYPE: PRT
<213> ORGANISM: Artificial Sequence
<220> FEATURE:
<223> OTHER INFORMATION: VH of anti-PD-1 mAb

<400> SEQUENCE: 35

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ser Asp Tyr
            20                  25                  30

Leu His Trp Tyr Gln Gln Lys Pro Gly Gln Ala Pro Arg Leu Leu Ile
        35                  40                  45

Lys Ser Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Asn Gly His Ser Phe Pro Tyr
                85                  90                  95

Thr Phe Gly Gln Gly Thr Lys Leu Glu Ile Lys
            100                 105

<210> SEQ ID NO 36
<211> LENGTH: 117
<212> TYPE: PRT
<213> ORGANISM: Artificial Sequence
<220> FEATURE:
<223> OTHER INFORMATION: VH of anti-TIM-3 mAb

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Pro Tyr Ala Pro Leu Asp Tyr Trp Gly Gln Gly Thr Leu
                100                 105                 110

Val Thr Val Ser Ser
            115

<210> SEQ ID NO 37
<211> LENGTH: 107
<212> TYPE: PRT
<213> ORGANISM: Artificial Sequence
<220> FEATURE:
<223> OTHER INFORMATION: VL of anti-TIM-3 mAb

<400> SEQUENCE: 37

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Asp Tyr
                 20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Gly Gly His Ala Pro Ile
                 85                  90                  95

Thr Phe Gly Gln Gly Thr Lys Val Glu Ile Lys
            100                 105

<210> SEQ ID NO 38
<211> LENGTH: 124
<212> TYPE: PRT
<213> ORGANISM: Artificial Sequence
<220> FEATURE:
<223> OTHER INFORMATION: VH of anti-TIM-3 mAb

<400> SEQUENCE: 38

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30

Trp Met Gln Trp Val Arg Gln Met Pro Gly Lys Gly Leu Glu Trp Met
            35                  40                  45

Gly Ala Ile Tyr Pro Gly Asp Gly Asp Ile Arg Tyr Thr Gln Asn Phe
 50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Glu Lys Ser Thr Thr Val Val Gln Arg Asn Tyr Phe Asp

Tyr Trp Gly Gln Gly Thr Thr Val Thr Val Ser Ser
                115                 120

<210> SEQ ID NO 39
<211> LENGTH: 106
<212> TYPE: PRT
<213> ORGANISM: Artificial Sequence
<220> FEATURE:
<223> OTHER INFORMATION: VL of anti-TIM-3 mAb

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Asn Val Gly Thr Phe
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Tyr Ser Tyr Pro Thr
                85                  90                  95

Phe Gly Gln Gly Thr Lys Leu Glu Ile Lys
            100                 105

<210> SEQ ID NO 40
<211> LENGTH: 509
<212> TYPE: PRT
<213> ORGANISM: Artificial Sequence
<220> FEATURE:
<223> OTHER INFORMATION: Recombinant hyaluronidase

<400> SEQUENCE: 40

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

-continued

```
Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
        210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
        290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
        370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
            435                 440                 445

Val Lys Asp Thr Asp Ala Val Asp Val Cys Ile Ala Asp Gly Val Cys
        450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
            500                 505
```